United States Patent
Guo et al.

(10) Patent No.: US 12,173,016 B2
(45) Date of Patent: Dec. 24, 2024

(54) STRONGLY-POLARIZED MOLECULE, AND SINGLE MOLECULE FIELD EFFECT TRANSISTOR PREPARED THEREFROM

(71) Applicant: Peking University, Beijing (CN)

(72) Inventors: Xuefeng Guo, Beijing (CN); Na Xin, Beijing (CN); Weining Zhang, Beijing (CN); Linan Meng, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 1115 days.

(21) Appl. No.: 17/042,800

(22) PCT Filed: Mar. 29, 2019

(86) PCT No.: PCT/CN2019/080347
§ 371 (c)(1),
(2) Date: Sep. 28, 2020

(87) PCT Pub. No.: WO2019/192395
PCT Pub. Date: Oct. 10, 2019

(65) Prior Publication Data
US 2021/0024560 A1 Jan. 28, 2021

(30) Foreign Application Priority Data

Apr. 2, 2018 (CN) .................... 201810283361.X

(51) Int. Cl.
| | | |
|---|---|---|
| *C07F 15/00* | (2006.01) | |
| *C07C 211/30* | (2006.01) | |
| *C07C 211/31* | (2006.01) | |
| *C07D 487/04* | (2006.01) | |
| *C07F 3/06* | (2006.01) | |
| *C07F 15/02* | (2006.01) | |
| *C07F 15/03* | (2006.01) | |
| *H10K 10/00* | (2023.01) | |
| *H10K 10/46* | (2023.01) | |
| *H10K 85/30* | (2023.01) | |
| *H10K 85/60* | (2023.01) | |

(52) U.S. Cl.
CPC ........ *C07F 15/0053* (2013.01); *C07C 211/30* (2013.01); *C07C 211/31* (2013.01); *C07D 487/04* (2013.01); *C07F 3/06* (2013.01); *C07F 15/0046* (2013.01); *C07F 15/025* (2013.01); *C07F 15/03* (2013.01); *H10K 10/701* (2023.02); *H10K 85/331* (2023.02); *H10K 85/344* (2023.02); *H10K 85/381* (2023.02); *H10K 85/624* (2023.02); *H10K 85/655* (2023.02); *H10K 85/6572* (2023.02); *H10K 10/46* (2023.02)

(58) Field of Classification Search
CPC .................... C07F 15/0053; H01K 85/624
See application file for complete search history.

(56) References Cited

U.S. PATENT DOCUMENTS

2015/0083988 A1  3/2015  Tanaka et al.

FOREIGN PATENT DOCUMENTS

| CN | 102456702 A | 5/2012 |
| CN | 104177366 A | 12/2014 |
| CN | 104744268 A | 7/2015 |
| CN | 105829454 A | 8/2016 |
| CN | 107011317 A | 8/2017 |
| JP | 2015065220 A | 4/2015 |

(Continued)

OTHER PUBLICATIONS

China Patent Office, First Office Action corresponding to CN application No. 202011405289.7, Aug. 11, 2021, 7 pages.
Japan Patent Office, First Office Action corresponding to JP application No. 2020-550619, Nov. 24, 2021, 4 pages.
Lin et al., "Chemical Modification of Graphene and Its Applications," Acta Chimica Sinica, 2014, 72:277-288.
E. Heyer, et al., "Panchromataic Push-Pull Dyes of Elongated Form from Triphenyl-amine, Diketopyrrolopyrrole, and Tetracyanobutadiene Modules," Synlett 2015, 26, 2109-2116.
European Patent Office, "Supplementary European Search Report," May 14, 2021, 17 pages.

(Continued)

*Primary Examiner* — Kamal A Saeed
(74) *Attorney, Agent, or Firm* — Umberg Zipser LLP

(57) ABSTRACT

The application relates to a strongly-polarized molecule of the following general formula: wherein A denotes a group having a polarizability greater than 2 C·m²/V; $R_1$ and $R_2$ are respectively hydrogen, halogen, a hydroxyl group, an amino group, a cyano group, a nitro group, a carboxyl group, a $C_{1-12}$ alkyl group, a $C_{1-12}$ alkoxy group, a halogenated $C_{1-12}$ alkyl group, a halogenated $C_{1-12}$ alkoxy group, a hydroxyl $C_{1-12}$ alkyl group, a hydroxyl $C_{1-12}$ alkoxy group, or a $C_{1-12}$ alkyl amino group; $x_1$ and $x_2$ denote 0 or an integer no less than 1, respectively; and $y_1$ and $y_2$ denote 0 or an integer no less than 1, respectively. The application further relates to a strongly-polarized molecule-graphene molecule heterojunction, and a single molecule field effect transistor comprising a substrate, a gate, a dielectric layer and the strongly-polarized molecule-graphene molecule heterojunction; and the dielectric layer is located between the gate and the strongly-polarized molecule-graphene molecule heterojunction. The single molecule field effect transistor provided by the application can realize highly-efficient gate modulation.

(FIG. 1)

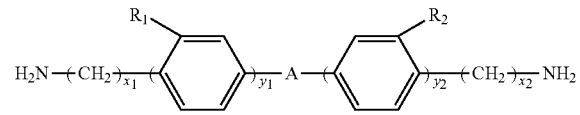

19 Claims, 2 Drawing Sheets

(56) References Cited

FOREIGN PATENT DOCUMENTS

| | | |
|---|---|---|
| JP | 2019524641 A | 9/2019 |
| KR | 20140007059 A | 1/2014 |
| KR | 20150122308 A | 11/2015 |
| KR | 101703118 B1 | 2/2017 |

OTHER PUBLICATIONS

J. Lee et al., "Toward the Realization of A Practical Diketopyrrolopyrrole-Based Small Molecule for Improved Efficiency in Ternary BHJ Solar Cells," Macromol. Rapid Commun. 2012, 33, 140-145.

J. Podlesny et al., "Structure-property relationships and third-order nonlinearities in diketopyrrolopyrrole based D-TT-A-TT-D molecules," Beilstein J. Org. Chem. 2017, 13, 2374-2384.

Li et al, "A Review on the Origin of Synthetic Metal Radical: Singlet Open-Shell Radical Ground State?," J. Phys. Chem. C, 2017, 121, 8579-8588.

S.S. Bagde et al., "Diketopyrrolopyrrole-based narrow band gap donors for efficient solution-processed organic solar cells," Chemical Physics Letters, 630 (2015) 37-43.

Korean Patent Office, Notice of Allowance, Korean Application No. KR 10-2020-7031057, Issued Dec. 29, 2022, 8 pages.

Diez-Perez et al., "Ambipolar Transport in an Electrochemically Gated Single-Molecule Field-Effect Transistor," ACS Nano, 2012; 6(8):7044-7052.

Marques-Gonzalez, et al., "Combined Spectroscopic and Quantum Chemical Study of [trans-Ru(C=CC6H4R1-4)2(dppe)2]n+ and [trans-Ru(C=CC6H4R1-4)(C=CC6H4R2-4)(dppe)2]n+ (n=0, 1) Complexes: Interpretations beyond the Lowest Energy Conformer Paradigm," Organometallics, 2014; 33:4947-4963.

Wheeler, Steven E., "Controlling the local arrangements of pi-stacked polycyclic aromatic hydrocarbons through substituent effects," CrystEngComm, 2012; 14:6140-6145.

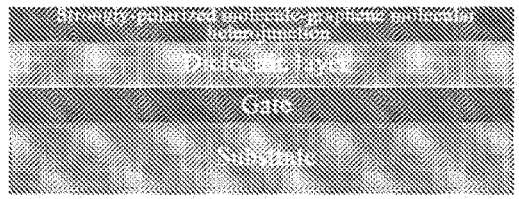 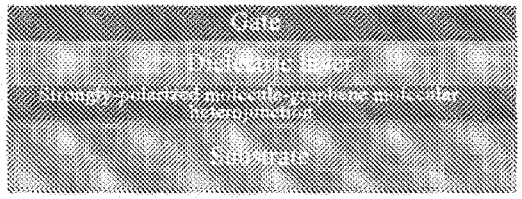
FIG. 1　　　　　　　　　　FIG. 2
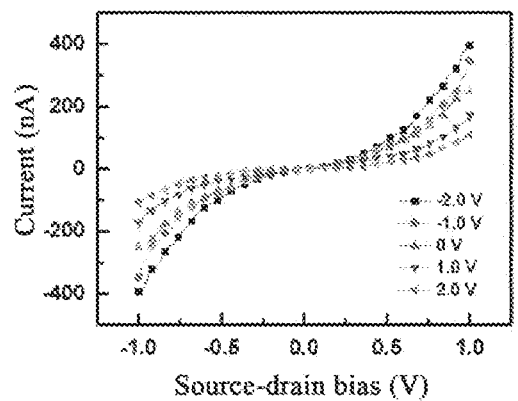 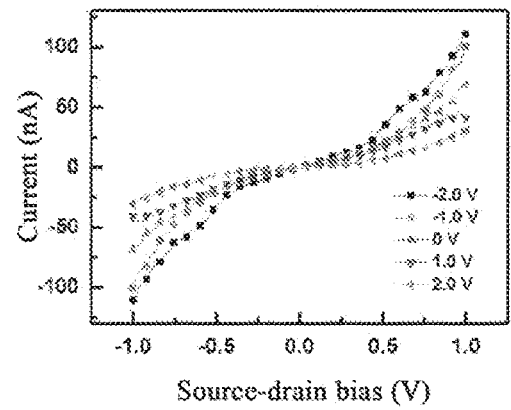
FIG. 3　　　　　　　　　　FIG. 4
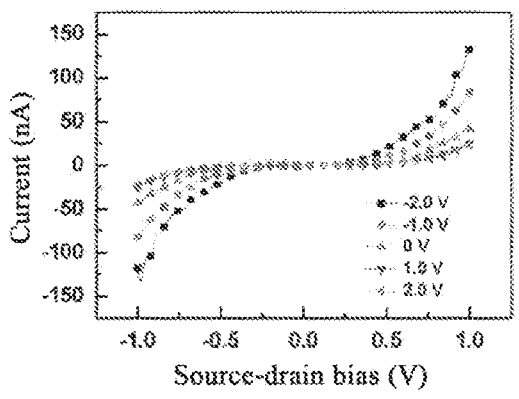 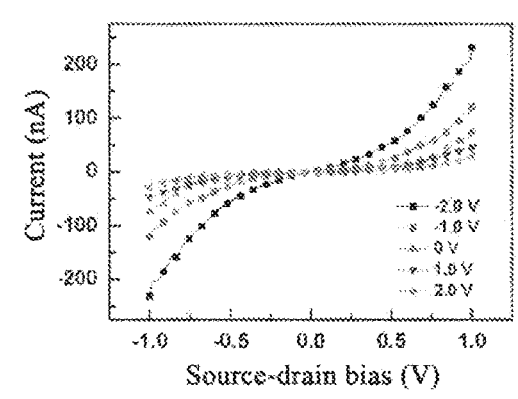
FIG. 5　　　　　　　　　　FIG. 6

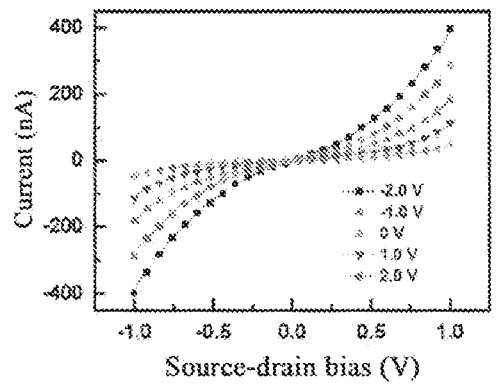
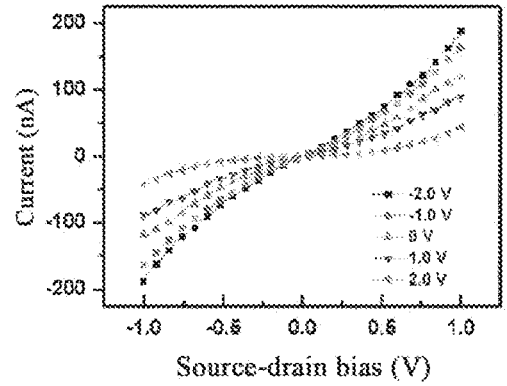
FIG. 7　　　　　　　　　FIG. 8
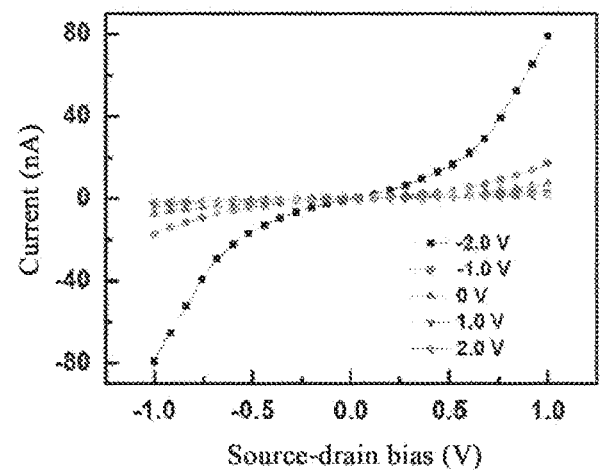
FIG. 9

STRONGLY-POLARIZED MOLECULE, AND SINGLE MOLECULE FIELD EFFECT TRANSISTOR PREPARED THEREFROM

The present application claims the priority of Chinese Patent Application No. 201810283361.X, filed before the CNIPA on Apr. 2, 2018, with the title of "STRONGLY-POLARIZED MOLECULE, AND SINGLE MOLECULE FIELD EFFECT TRANSISTOR PREPARED THEREFROM", which is incorporated herein by reference in its entirety.

FIELD OF THE INVENTION

This application relates to the technical field of single molecule electronic devices, in particular to a strongly-polarized molecule and a single molecule field effect transistor prepared therefrom.

BACKGROUND OF THE INVENTION

In the current semiconductor industry, the core of electronic circuits is transistors, which are the cornerstone of the contemporary digital revolution. Since the first model of transistors was proposed in 1947, researchers have developed various types of transistors. The fundamental principle of transistors is that: as the capacitance effect of the dielectric layer can change the carrier concentration at the interface between the insulation layer and the semiconductor layer, the current between source electrodes and drain electrodes can be modulated by applying an appropriate voltage to the gate. Therefore, on the one hand, the logic function of the switch can be realized, and on the other hand, since the output power is higher than the input power, the transistor has an amplifier function. Similarly, in the field of single molecule electronics, single molecule field effect transistors have also aroused great interest among researchers. The electrostatic potential of a molecule in a single molecule heterojunction can be modulated by applying gate voltage, and thereby energy levels of the molecules are changed, which is different from traditional field-effect transistors. Therefore, on the one hand, the conductive properties of the molecule can be modulated, and on the other hand, certain information related to the vibration mode and excited state of the molecule and vibration-related information can be obtained. However, single molecule field effect transistors are still only at the conceptual stage and have not been implemented in the prior art.

SUMMARY OF THE INVENTION

The examples of the present application aim to provide a strongly-polarized molecule and a single molecule field effect transistor prepared therefrom. The specific technical solutions are as follows:

First of all, the present application provides a strongly-polarized molecule of general formula (I):

general formula (I)

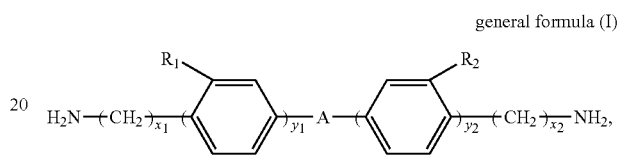

wherein A is a group having a polarizability greater than 2 Cm·$^2$/V;

$R_1$ and $R_2$ are respectively any one of hydrogen, halogen, hydroxyl, amino, cyano, nitro, carboxyl, $C_{1-12}$ alkyl, $C_{1-12}$ alkoxy, halogenated $C_{1-12}$ alkyl, halogenated $C_{1-12}$ alkoxy, hydroxyl $C_{1-12}$ alkyl, hydroxyl $C_{1-12}$ alkoxy, or $C_{1-12}$ alkyl amino;

$x_1$ and $x_2$ are 0 or a positive integer, respectively; preferably, $0 \leq x_1 \leq 3$; $0 \leq x_2 \leq 3$; more particularly, $x_1$ and $x_2$ are 0, 1, 2 or 3, respectively;

$y_1$ and $y_2$ are 0 or a positive integer, respectively; preferably, $0 \leq y_1 \leq 2$, $0 \leq y_2 \leq 2$; more particularly, $y_1$ and $y_2$ are 0, 1 or 2, respectively.

In some embodiments of the present application, $x_1$ and $x_2$ can be the same or different;

Similarly, in some embodiments of the present application, $y_1$ and $y_2$ can be the same or different;

Some embodiments of the present application relate to the strongly-polarized molecule of general formula (I) as described above, wherein A is:

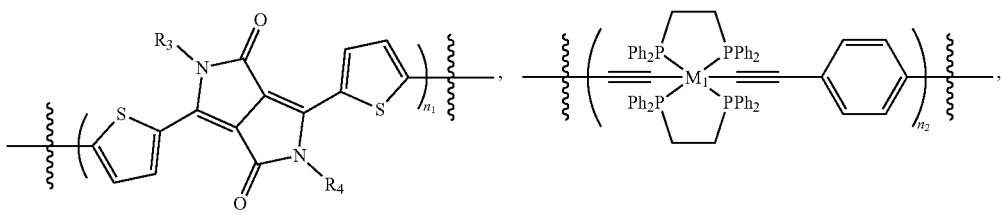

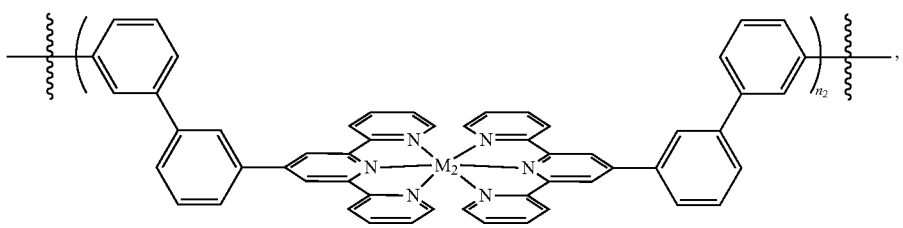

-continued
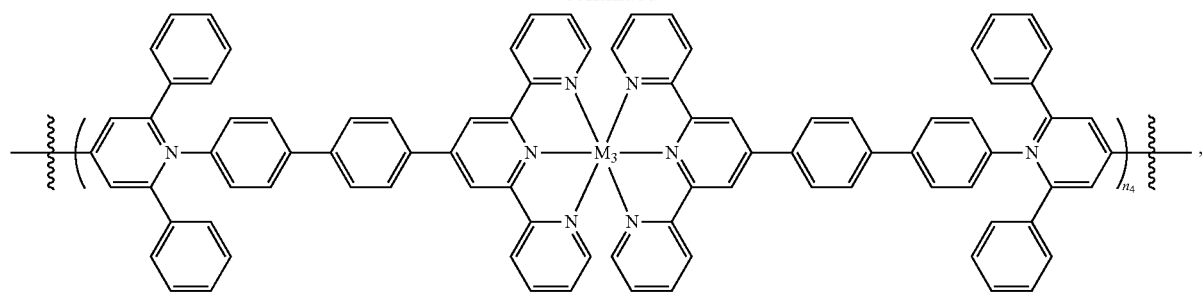
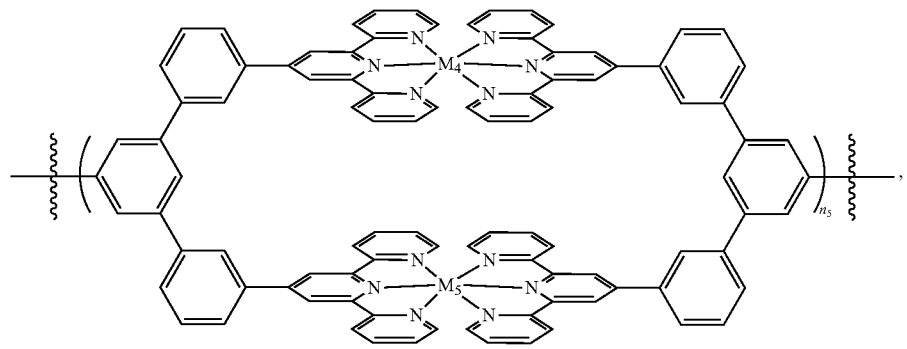
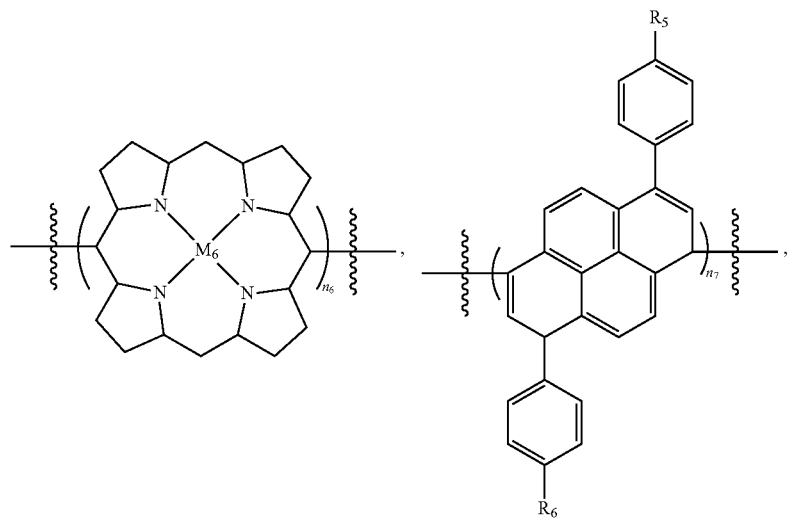
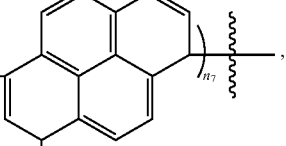
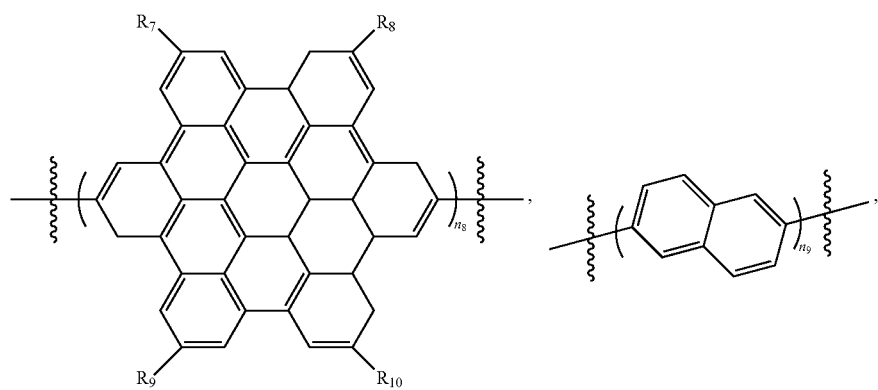
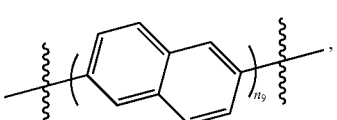

-continued

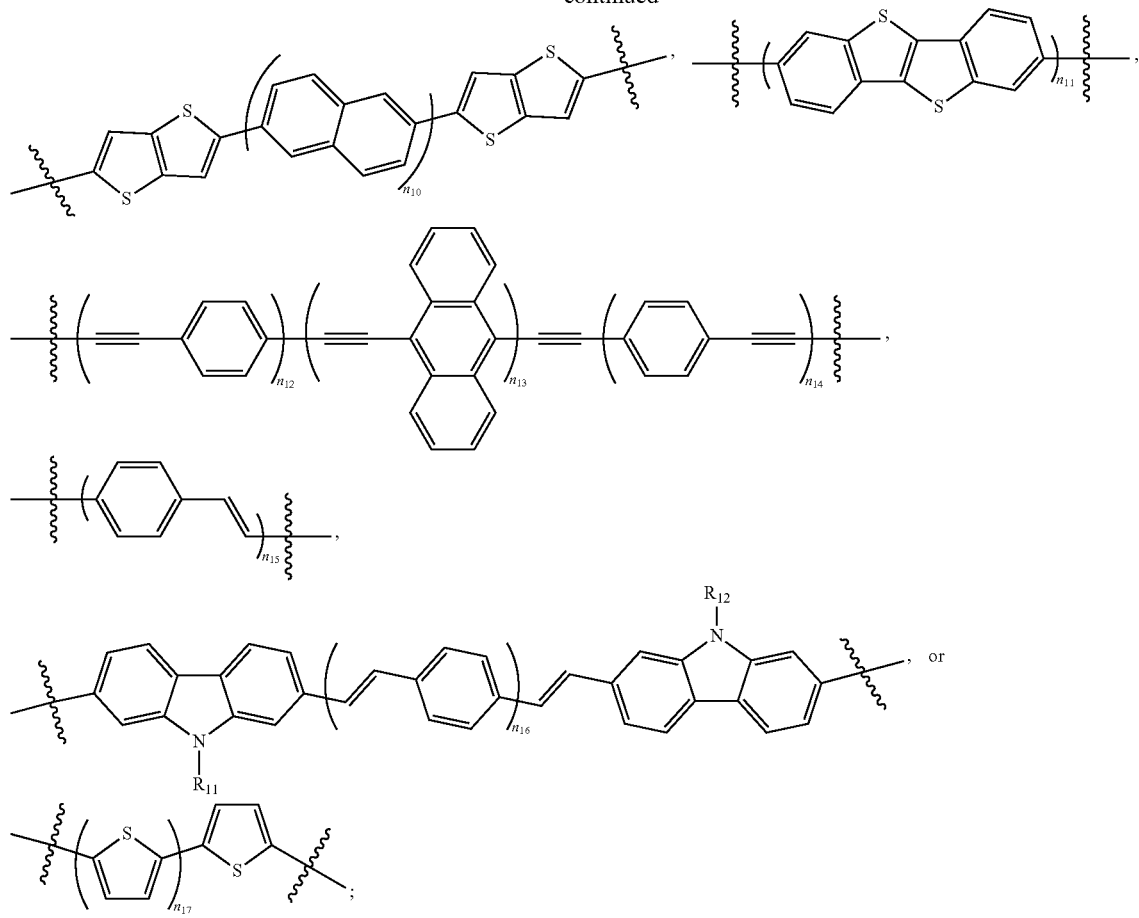

$R_3$, $R_4$, $R_5$, $R_6$, $R_7$, $R_8$, $R_9$, $R_{10}$, $R_{11}$ and $R_{12}$ are respectively any one of hydrogen, halogen, hydroxyl, amino, cyano, nitro, carboxyl, $C_{1-12}$ alkyl, $C_{1-12}$ alkoxy, halogenated $C_{1-12}$ alkyl, halogenated $C_{1-12}$ alkoxy, hydroxyl $C_{1-12}$ alkyl, hydroxyl $C_{1-12}$ alkoxy, or $C_{1-12}$ alkyl amino;

$M_1$, $M_2$, $M_3$, $M_4$, $M_5$ and $M_6$ are respectively a central atom or central ion of the complex; preferably, $M_1$, $M_2$, $M_3$, $M_4$, $M_5$ and $M_6$ are respectively selected from the group consisting of Ru, Fe, Zn, Mn, Co, Ni and cation thereof;

$n_1$, $n_2$, $n_3$, $n_4$, $n_5$, $n_6$, $n_7$, $n_8$, $n_9$, $n_{10}$, $n_{11}$, $n_{12}$, $n_{13}$, $n_{14}$, $n_{15}$, $n_{16}$ and $n_{17}$ are respectively a positive integer; preferably, $n_1$, $n_2$, $n_3$, $n_4$, $n_5$, $n_6$, $n_7$, $n_8$, $n_9$, $n_{10}$, $n_{11}$, $n_{12}$, $n_{13}$, $n_{14}$, $n_{15}$, $n_{16}$ and $n_{17}$ are smaller than or equal to 3.

As used herein, the abbreviation "Ph" is phenyl.

As used herein, the term "halogen" refers to fluorine, chlorine, bromine or iodine.

As used herein, the term "$C_{1-12}$ alkyl" refers to a linear or branched saturated hydrocarbon group containing 1-12 carbon atoms, including but not limited to methyl, ethyl, n-propyl, isopropyl, n-butyl, isobutyl, 3-ethylheptyl and n-dodecyl.

As used herein, the "〰" in the structural formula of a group represents the attachment site of the group to the other parts of the molecule.

As used herein, "complex" can also be referred to as a chelate. Those skilled in the art can easily determine the valence of the metal according to the structural formula of the complex or the complex ion based on the prior art, when Ru, Fe, Zn, Mn, Co, Ni, etc. are in the form of cations for forming complexes. For example, the core ion in the complex can be $Ru^{2+}$, $Fe^{2+}$, $Zn^{2+}$, $Mn^{2+}$, $Co^{2+}$, $Ni^{2+}$, etc.

Some embodiments of the present application relate to the aforementioned strongly-polarized molecules, which have one of the following general formulae:

general formula (II)

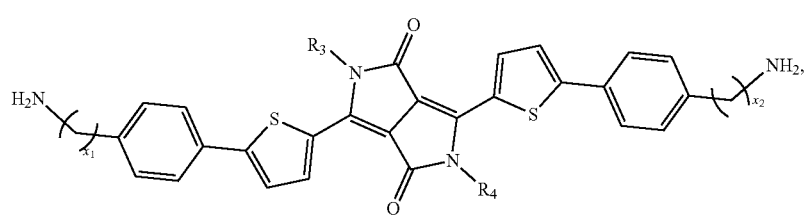

-continued
general formula (III)
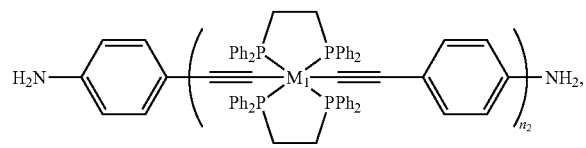
general formula (IV)
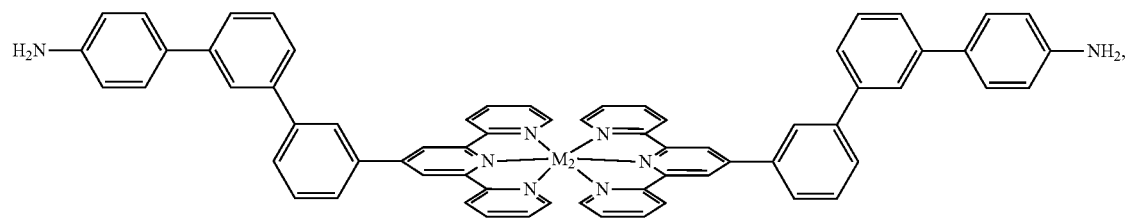
general formula (V)
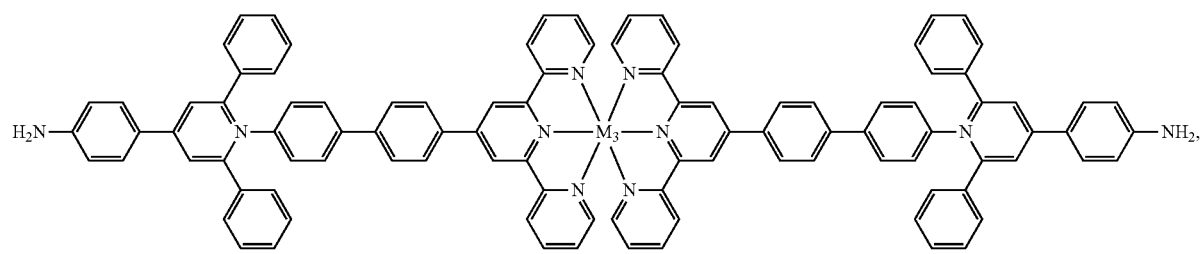
general formula (VI)
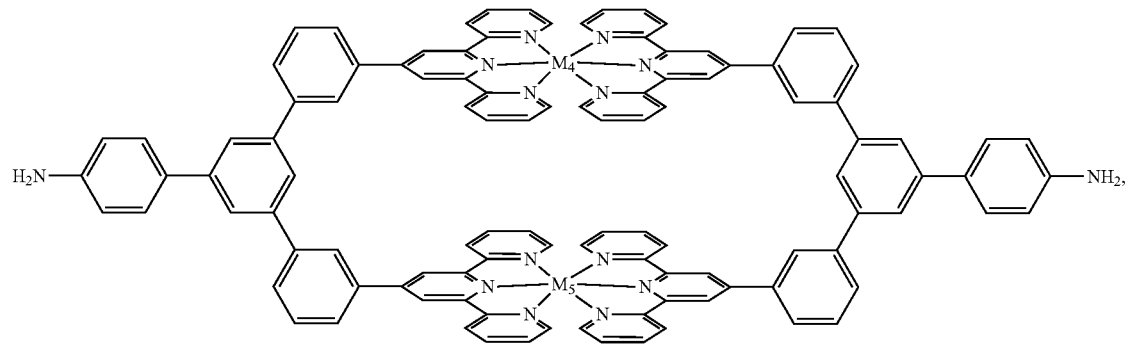
general formula (VII)
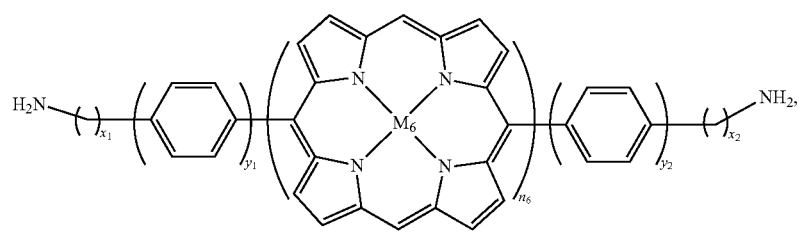

general formula (VIII)
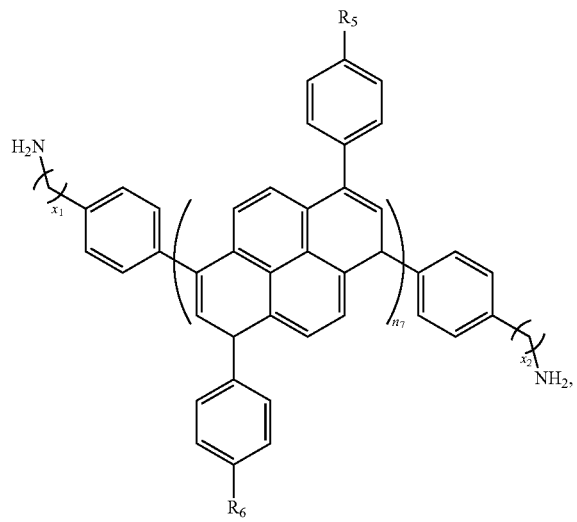
general formula (IX)
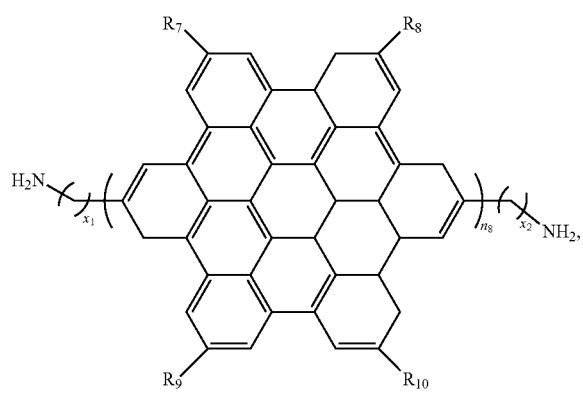
general formula (X)
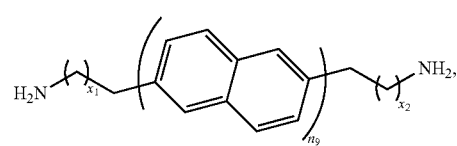
general formula (XI)
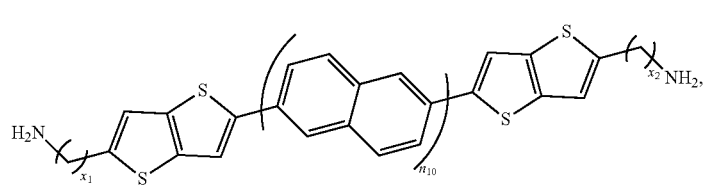
general formula (XII)
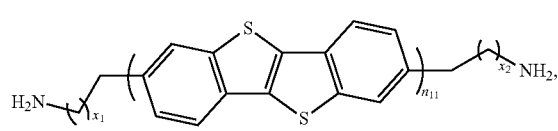
general formula (XIII)
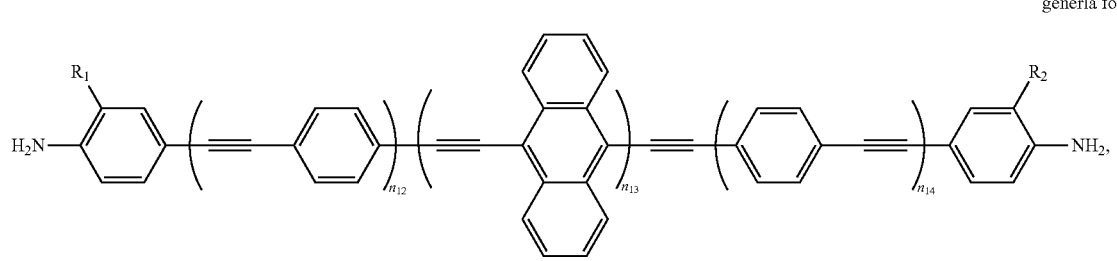
general formula (XIV)
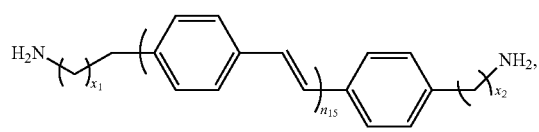

general formula (XV)

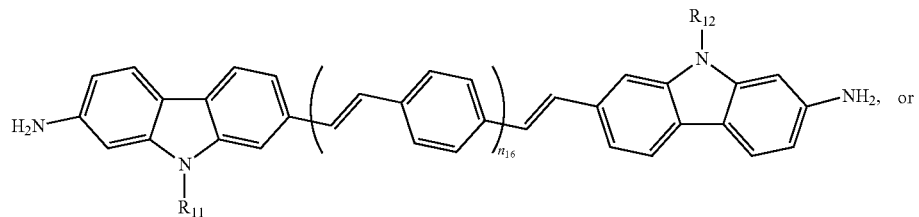

general formula (XVI)

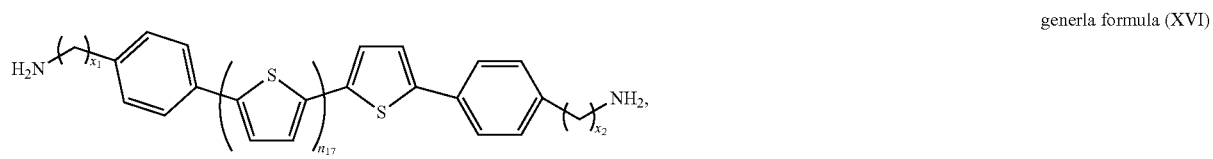

wherein, $R_1$, $R_2$, $R_3$, $R_4$, $R_5$, $R_6$, $R_7$, $R_8$, $R_9$, $R_{10}$, $R_{11}$, $R_{12}$, $M_1$, $M_2$, $M_3$, $M_4$, $M_5$, $M_6$, $n_2$, $n_6$, $n_7$, $n_8$, $n_9$, $n_{10}$, $n_{11}$, $n_{12}$, $n_{13}$, $n_{14}$, $n_{15}$, $n_{16}$, $n_{17}$, $x_1$, $x_2$, $y_1$, and $y_2$ are as defined above.

In some embodiments of the present application, the strongly-polarized molecules represented by the aforementioned general formulae (I)-(XVI) have one of the following structural formulae:

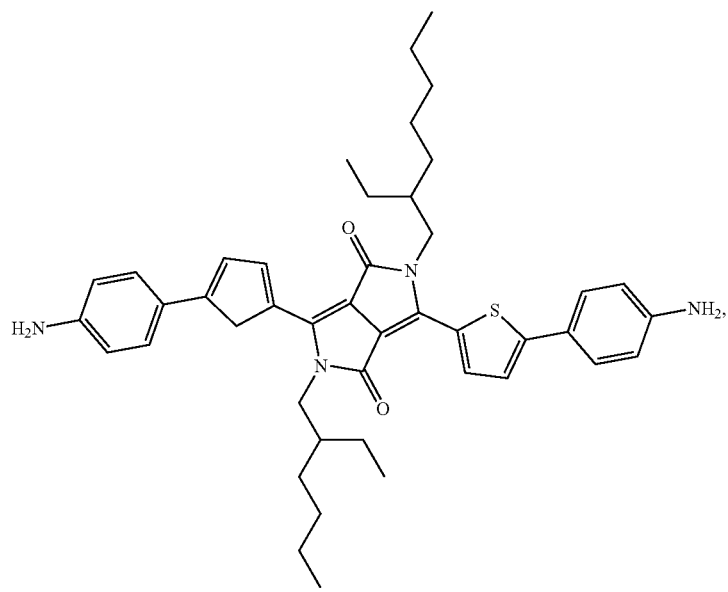

-continued
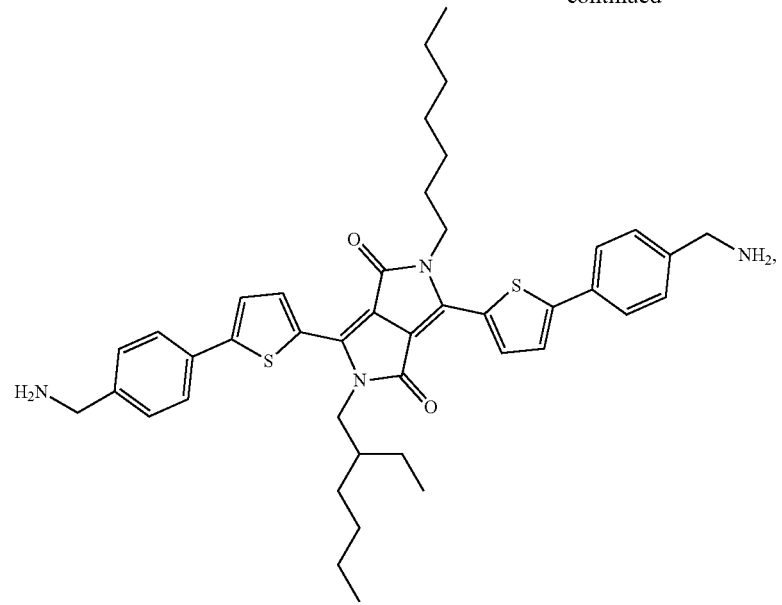
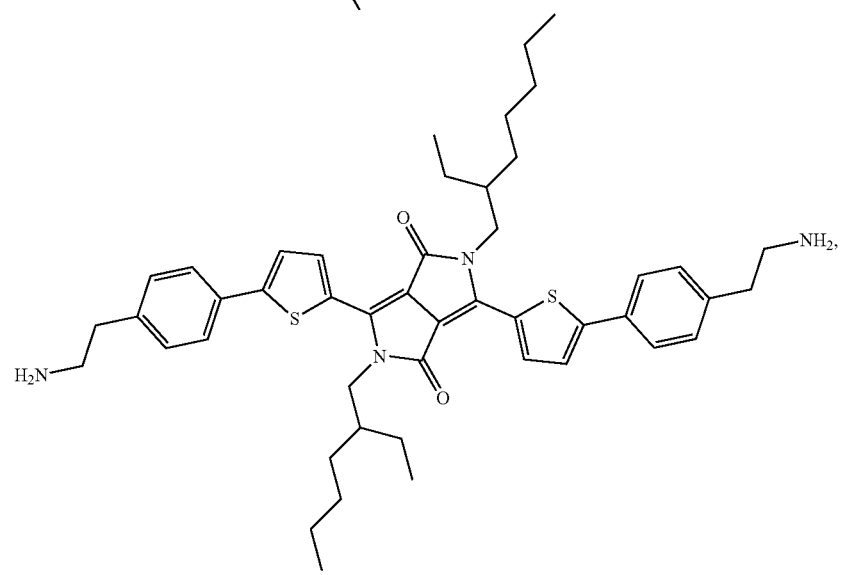
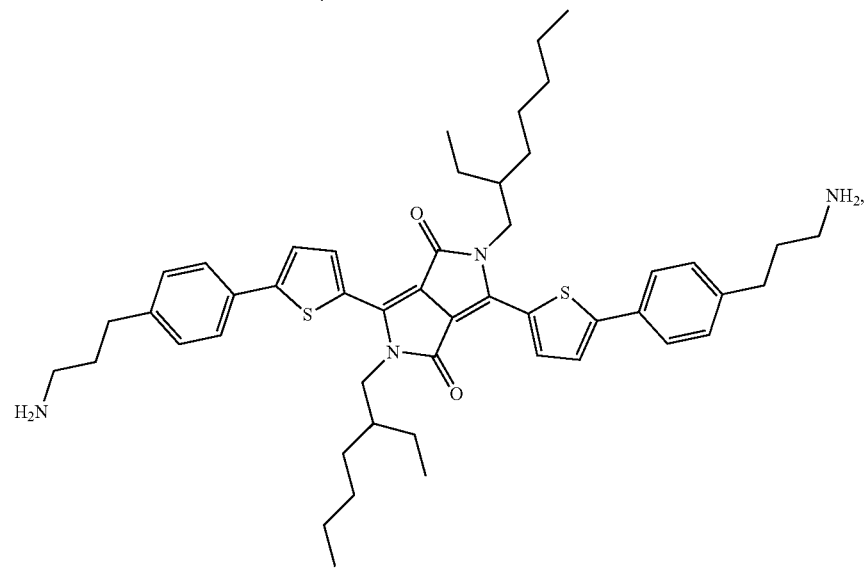

-continued
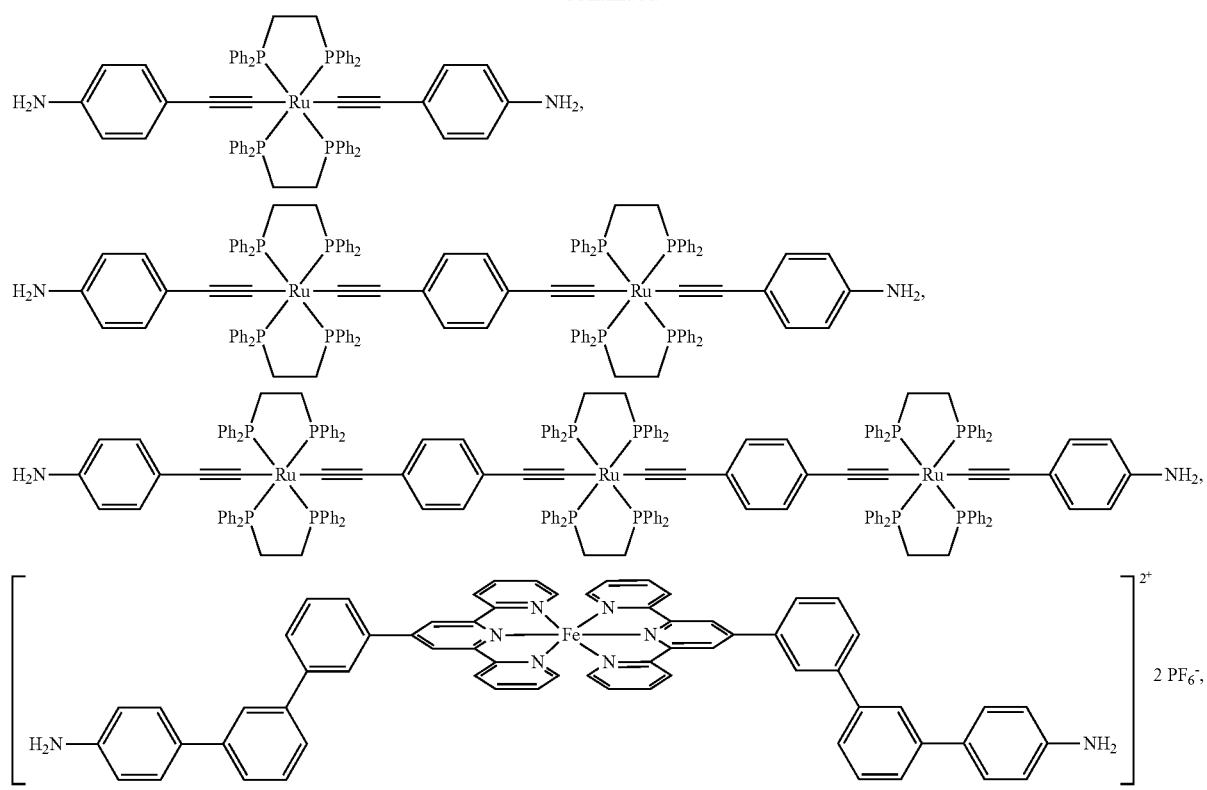
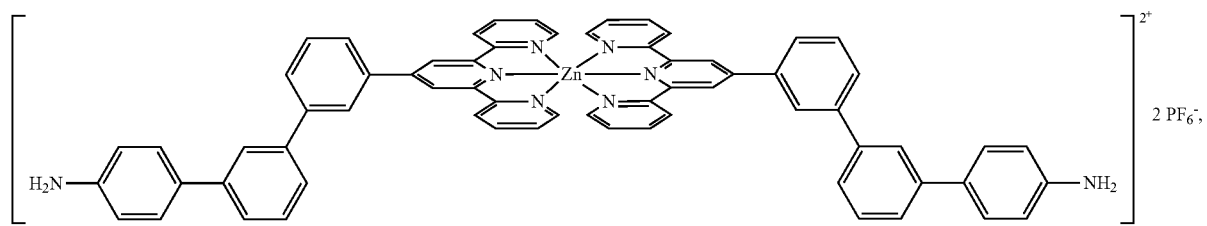
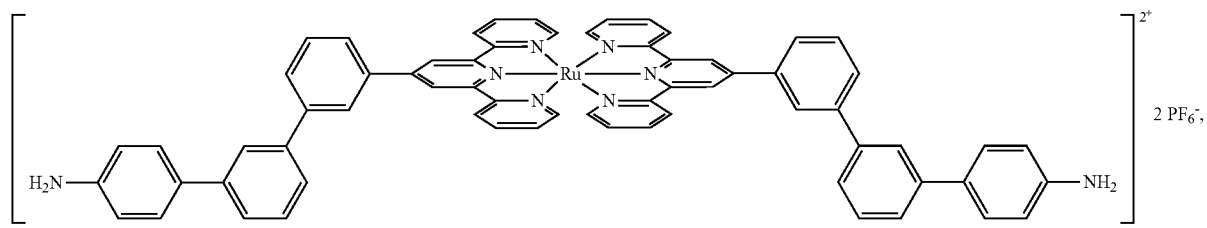
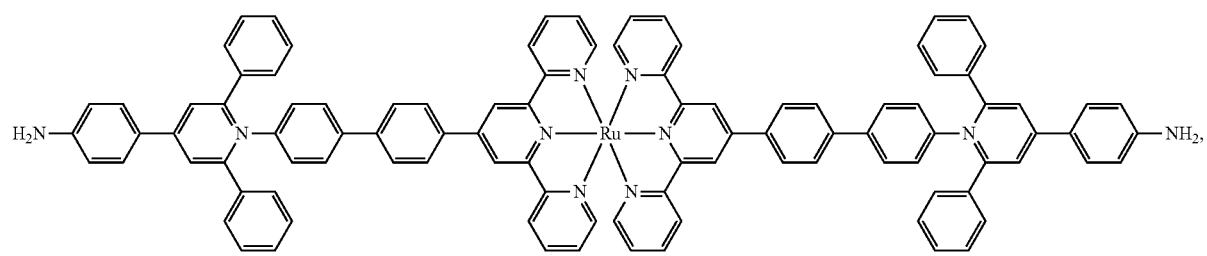

-continued

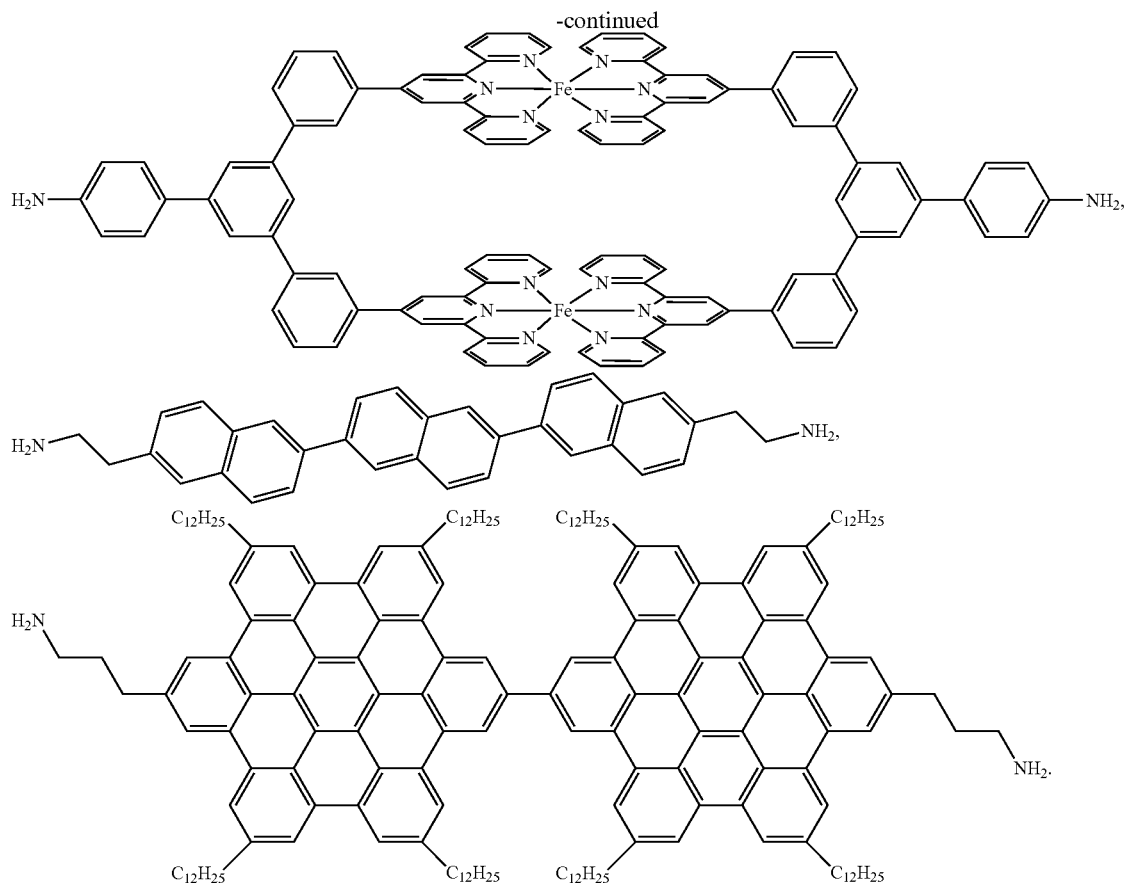

Through in-depth research, the inventor found that, without being limited to any theory, when a voltage is applied, especially within the gate modulation voltage of −2 V to +2 V, the aforementioned strongly-polarized molecules are prone to polarization so that the molecular orbital energy level shifts for compatible with gate modulation. Therefore, the gate modulation of the single molecule field effect transistor can be effectively realized.

The present application also provides a strongly-polarized molecule-graphene molecular heterojunction, wherein the molecular heterojunction includes the aforementioned strongly-polarized molecule bridging between layers of the two-dimensional single-layer graphene via amide covalent bonds.

In some embodiments of the present application, the two-dimensional single-layer graphene with a nanogap is a two-dimensional single-layer graphene with an array of nanogaps.

This application also provides a method for preparing a strongly-polarized molecule-graphene molecular heterojunction, which includes the following steps:

(1) preparing the two-dimensional single-layer graphene with a nanogap, which can be constructed on a support;

(2) dissolving the strongly-polarized molecule provided in the present application and dehydrating agents (for example: 1-ethyl-3-(3-dimethylaminopropyl) carbodiimide hydrochloride, EDCI) in an organic solvent (for example: pyridine) to obtain a solution of molecules to be connected;

(3) adding the two-dimensional single-layer graphene with nanogap (which can be together with its support) into the solution, reacting for 1-4 days in the absence of light, washing and drying.

In this application, the "two-dimensional single-layer graphene with a nanogap" can be prepared by the method described in the literature (see *Angew. Chem. Int. Ed.* 2012, 51, 12228.), which has been incorporated herein by reference in its entirety, and will not be repeated here.

The "two-dimensional single-layer graphene with a nanogap" or "two-dimensional single-layer graphene with an array of nanogaps" is also referred to as graphene nanogap electrode or graphene nano-electrode in the prior art.

The term "in the absence of light" can also be understood as in dark. For those skilled in the art, the meaning of in the absence of light or in dark is clear.

In a specific embodiment of the present application, after the reaction is completed in the absence of light, the two-dimensional single-layer graphene with a nanogap is taken out of the solution, washed with a large amount of acetone and ultrapure water, and dried in $N_2$ gas stream. In this application, the ultrapure water used preferably has a resistivity greater than 18 MΩ·cm.

This application also provides a single molecule field effect transistor, which may comprise a substrate, a gate, a dielectric layer, and the strongly-polarized molecule-graphene molecular heterojunction. The dielectric layer is located between the gate and the strongly-polarized molecule-graphene molecular heterojunction.

In a specific implementation process, the two-dimensional single-layer graphene on both sides of the gap in the strongly-polarized molecule-graphene molecule heterojunction can be used as source electrodes and drain electrodes of the single-molecule field effect transistor.

In some embodiments of the present application, the material of the gate is one of graphene or metallic aluminum.

In some embodiments of the present application, the material of the dielectric layer is one of hafnium oxide, zirconium oxide, titanium oxide and aluminum oxide, or any combinations thereof.

In some embodiments of the present application, the present application provides a single molecule field effect transistor, wherein:
- the dielectric layer is a hafnium oxide layer, and the gate is a graphene layer; or
- the dielectric layer is a zirconium oxide layer, and the gate is a graphene layer; or
- the dielectric layer is a titanium oxide layer, and the gate is a graphene layer; or
- the dielectric layer is an aluminum oxide layer, and the gate is a metal aluminum layer; or
- the dielectric layer is a composite layer of aluminum oxide and hafnium oxide, and the gate is a metal aluminum layer.

The inventor found that the single molecule field effect transistor obtained by using the above-mentioned gate material, dielectric layer material, and the above-mentioned combination of gate and dielectric layer has a higher gate modulation efficiency with a relatively simple preparation method of transistor and better application prospects.

Herein, the "substrate" may also be referred to as a base. In some specific embodiments of the present application, the substrate may be a silicon wafer having a silicon oxide layer, which is commercially available. In a specific implementation process, the gate or the strongly-polarized molecule-graphene molecular heterojunction is located on the silicon oxide layer. The inventor found that when the thickness of the silicon oxide layer is 200-400 nm, and preferably 300 nm, the optical contrast of the graphene is better. Of course, those skilled in the art can also use other substrates to implement the technical solutions of the present application.

In some embodiments of the present application, the thickness of the dielectric layer is 3-10 nm, preferably 4-7 nm, and more preferably 5 nm.

Regarding the thickness of the gate, since it has no substantial influence on the performance of the transistor itself, it is not specifically limited here in the present application. The thickness of the gate can be selected by those skilled in the art according to the actual requirements of size of the transistor itself. In some embodiments of the present application, the thickness of aluminum can be selected from 20 to 30 nm, when the metal aluminum is used as the gate material; the thickness of the single-layer graphene itself is less than 1 nm, when graphene is used as the gate material.

In some embodiments of the present application, the present application provides a single-molecule field effect transistor, wherein the gate is located on the substrate, the dielectric layer is located on the gate, and the strongly-polarized molecule-graphene molecule heterojunction is located on the dielectric layer, to form a bottom gate structure, as shown in FIG. 1;

or the strongly-polarized molecule-graphene molecule heterojunction is located on the substrate, the dielectric layer is located on the strongly-polarized molecule-graphene molecule heterojunction, and the gate is located on the dielectric layer, to form a top gate structure, as shown in FIG. 2.

In some specific embodiments of the present application, 5 combinations in the following Table 1 can be used to make a single molecule field effect transistor with a bottom gate structure:

TABLE 1

| Combination of gate and dielectric layer | | | | | |
|---|---|---|---|---|---|
| Combination No. | 1 | 2 | 3 | 4 | 5 |
| Gate | Graphene | Graphene | Graphene | Aluminum | Aluminum |
| Dielectric layer | Hafnium oxide | Zirconium oxide | Titanium oxide | Aluminum oxide | Aluminum oxide + Hafinum oxide |

In a specific embodiment, the single molecule field effect transistor with a bottom gate structure can be prepared by the following method:

For combination 1, combination 2 and combination 3, a single-layer graphene grown by chemical vapor deposition (see *Sci. Rep.* 2012, 2, 707.) can be transferred onto the substrate (for example, a silicon wafer having an oxide layer of 300 nm) as the gate (referred to as bottom gate) (see *ACS Nano* 2011, 5, 6916.). Then a dielectric layer is formed on the bottom gate. The thickness of each of the three types of dielectric layers can be 3-10 nm. Hafnium oxide can be prepared by atomic layer deposition and sol-gel method (see *Adv. Mater* 2015, 27, 2113.), wherein the sol-gel method is relatively cheap and therefore more preferred. Both zirconium oxide and titanium oxide can be prepared by electron beam evaporation deposition or atomic layer deposition.

For combination 4, an aluminum layer with a certain thickness (such as 35 nm) can be deposited on the substrate by electron beam evaporation deposition, and then heated at 180° C. for 1 hour, so that an aluminum oxide layer of a certain thickness (such as 5 nm) can be made on the aluminum layer.

For combination 5, an aluminum layer with a certain thickness (such as 35 nm) can be deposited on the substrate by electron beam evaporation deposition, located in the atmosphere for a period of time (such as 24 hours), and naturally oxidized to obtain an aluminum oxide layer with a certain thickness (such as 3 nm), on which a hafnium oxide layer with a certain thickness (such as 2 nm) is further deposited by atomic layer deposition.

After the bottom gate and the dielectric layer are prepared by the previous method, a two-dimensional single-layer graphene with a nanogap is constructed on the dielectric layer (see *Angew. Chem. Int. Ed.* 2012, 51, 12228.), and then through the chemical self-assembly method, specifically, through acylation reaction, the strongly-polarized molecules represented by the aforementioned general formulae (I)-(XVI) bridge between layers of graphene to form a strongly-polarized molecules-graphene molecule heterojunction.

It should be noted that the "electron beam evaporation deposition" and "atomic layer deposition" herein are both conventional micro-nano processing techniques. In order to realize the technical solution of this application, electron beam evaporation deposition of a metal layer or metal oxide layer with a certain thickness, or atomic layer deposition of a metal layer or metal oxide layer with a certain thickness is very easy to implement for those skilled in the art, which will not be repeated in this application.

In some specific embodiments of the present application, when preparing a single molecule field effect transistor with a top gate structure, the gate and the dielectric layer can also use the 5 combinations in Table 1. Nevertheless, the first three combinations are preferred from the perspective of the simplicity of preparation process. In a specific implementation process, for combination 1, combination 2 and combination 3, a two-dimensional single-layer graphene with a nanogap array is firstly constructed on the substrate. After forming the strongly-polarized molecule-graphene molecule heterojunction by chemical self-assembly method, PMMA (polymethyl methacrylate) is used as a support to transfer the dielectric layer and the gate onto the monomolecular heterojunction. The transferring process of the dielectric layer and the gate may specifically include: firstly, preparing a dielectric layer on a silicon wafer, which may be implemented by using the dielectric layer preparation method in the preparation method of the bottom gate structure, then transferring the graphene grown by chemical vapor deposition on the dielectric layer, further spin-coating PMMA thereon, etching the silicon wafer having hydrofluoric acid, rinsing the dielectric layer/graphene/PMMA film with deionized water and isopropanol three times, and then located placing it on the molecular heterojunction (see *ACS Nano* 2011, 5, 6916.). As used herein, "support" refers to the carrier used to transfer the graphene gate.

The present application also provides a molecular switch, which includes the aforementioned single molecule field effect transistor.

The present application also provides a semiconductor chip, which includes the aforementioned single molecule field effect transistor.

This application provides a strongly-polarized molecule as shown in general formula (I). Single molecule field effect transistors are prepared with these molecules for the first time, which is a breakthrough. Since graphene is used as source electrodes and drain electrodes, and the graphene has the matching size with the molecules, which greatly improves the coupling efficiency between the molecules and the gate, and, the efficient gate modulation can be realized cooperating with the strongly-polarized molecule structure.

Moreover, the size of the single molecule field effect transistor provided by the present application is within the molecular size range, which strongly promotes the miniaturization of the field effect transistor. Therefore, the semiconductor chip prepared by the single molecule field effect transistor provided by the present application can greatly improve integration. Furthermore, the single molecule field effect transistor provided in the present application has good performance reproducibility, which is more conducive to the application of single molecule field effect transistors.

In addition, since the strongly-polarized molecule-graphene molecule heterojunction can be produced in batches, the single molecule field effect transistor device constructed based on the strongly-polarized molecule-graphene molecule heterojunction provided in this application can be produced in batches.

In summary, the single molecule field effect transistor provided in this application is of epoch-making significance in the technological field of semiconductor.

DESCRIPTION OF THE DRAWINGS

In order to more clearly illustrate the examples of the present application and the embodiments of the prior art, the following description of the embodiments and the drawings of the prior art will be briefly described. It is obvious to those skilled in the art that the drawings in the following description are only some examples of the application, and may be used to obtain other figures from these figures without any inventive efforts.

FIG. 1 is a schematic diagram of the structure of the single molecule field effect transistor with a bottom gate structure.

FIG. 2 is a schematic diagram of the structure of the single molecule field effect transistor with a top gate structure.

FIG. 3 is an I-V characteristic curve of the compound 1 based single molecule field effect transistor prepared in Example 1.

FIG. 4 is an I-V characteristic curve of the compound 2 based single molecule field effect transistor prepared in Example 2 within a gate voltage range of −2 V to +2 V.

FIG. 5 is an I-V characteristic curve of the compound 3 based single molecule field effect transistor prepared in Example 3 within a gate voltage range of −2 V to +2 V.

FIG. 6 is an I-V characteristic curve of the compound 4 based single molecule field effect transistor prepared in Example 4 within a gate voltage range of −2 V to +2 V.

FIG. 7 is an I-V characteristic curve of the compound 5 based single molecule field effect transistor prepared in Example 5 within a gate voltage range of −2 V to +2 V.

FIG. 8 is an I-V characteristic curve of the compound 6 based single molecule field effect transistor prepared in Example 6 within a gate voltage range of −2 V to +2 V.

FIG. 9 is an I-V characteristic curve of the compound 7 based single molecule field effect transistor prepared in Example 7 within a gate voltage range of −2 V to +2 V.

DETAILED DESCRIPTION OF THE INVENTION

The technical solutions in the embodiments of the present application are clearly and completely described in the following with reference to the drawings in the examples of the present application. It is obvious that the described examples are only a part of the examples of the present application, but not all of them. All other examples obtained by those skill in the art based on the examples of the present application without making inventive efforts are within the scope of the present application.

The experimental methods described in the following examples are conventional methods unless otherwise specified. The reagents and materials, unless otherwise specified, are commercially available.

Preparation Example of Single Molecule Field Effect Transistor
Example 1: Preparation of Compound 1 Based Single Molecule Field Effect Transistor
(1) Synthesis of Compound 1
The synthetic route is as follows:
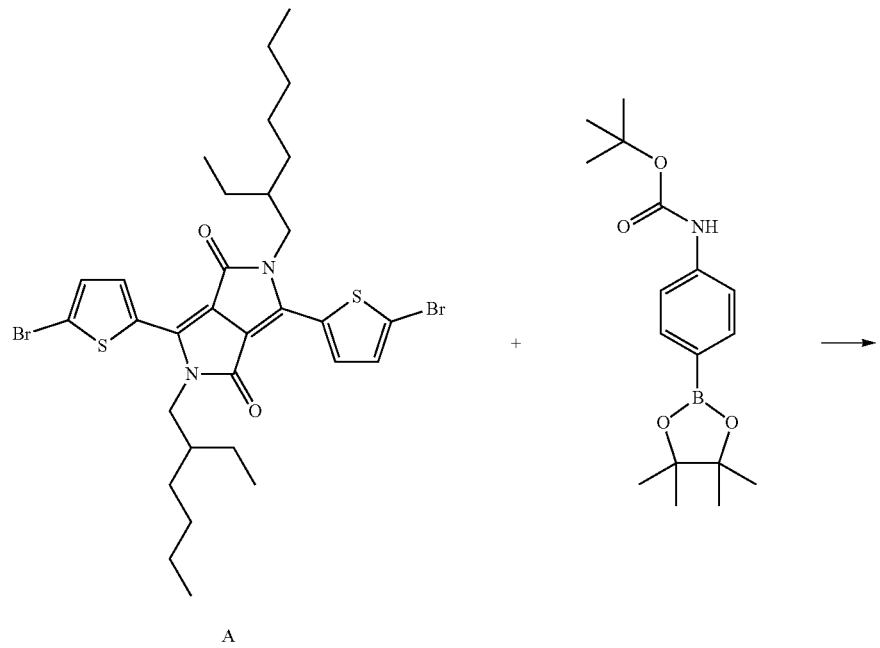
A
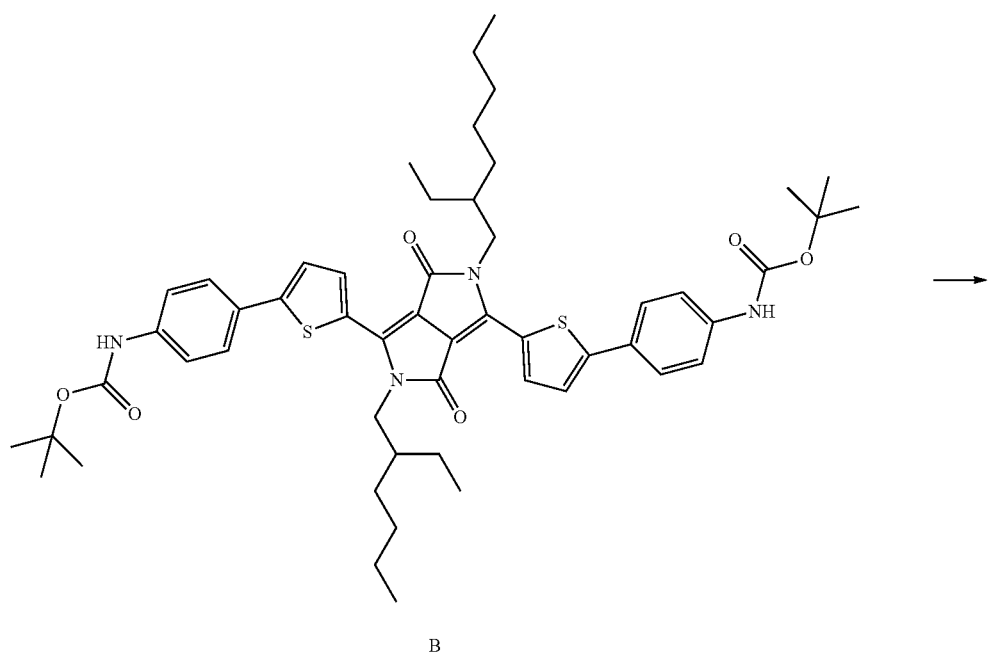
B

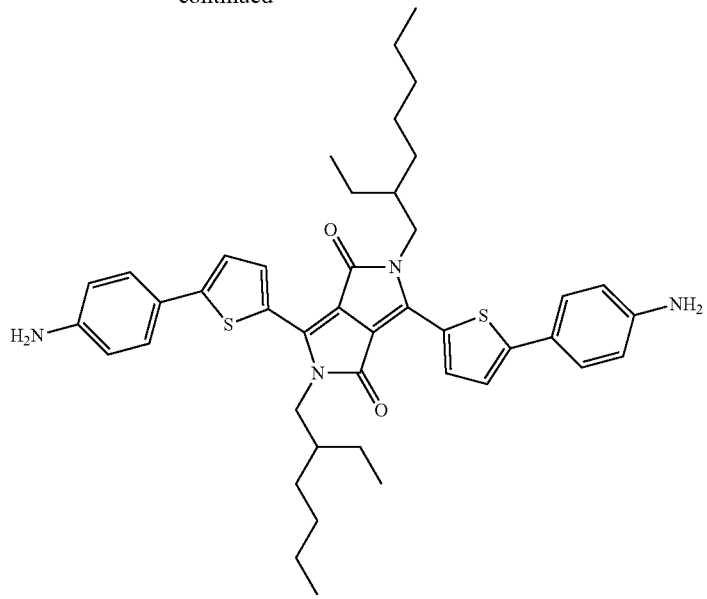

Compound A was synthesized according to the method described in the literature (*J. Am. Chem. Soc.,* 2010, 132 (44), pp 15547-15549).

Compound A (857 mg, 1.23 mmol), N—Boc-4-aminophenylboronic acid pinacol ester (865 mg, 2.71 mmol), bis(dibenzalacetone) palladium (22.6 mg, 24.6 μmol), tri(o-tolyl)phosphine (30.1 mg, 98.6 μmop, and anhydrous potassium carbonate (1.60 g, 11.6 mmol) were added to a 100 mL Schlenk bottle in sequence. After adding 2 drops of aliquat 336 (methyl trioctyl ammonium chloride), 24 mL of toluene and 6 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). After the organic phases were combined and dried over anhydrous sodium sulfate, the solvent was removed under reduced pressure. The crude product was analyzed and purified by silica gel column chromatography to obtain compound B as a purple solid. $^1$H NMR (400 MHz, CDCl$_3$, 298 K): δ 7.87 (d, =8.5 Hz, 2.11), 7.65 (ddd, 0.1=8.7, 1.3, 0.4 Hz, 4H), 739 (m, 614), 4.10 (d, 7.0 Hz, 4H), 1.64 (m, 2H), 1.45 (s, 18H), 1.15-1.38 (m, 14H), 0.76-0.91 (m, 16H). $^{13}$C NMR (100 MHz, CDCl$_3$, 298 K): δ 1.7183, 153.93, 148.85, 145.64, 138.76, 133.63, 127.67, 127.38, 123.40, 121.45, 119.57, 100.02, 80.43, 46.33, 38.65, 37.60, 32.11, 30.79, 79.64, 28.61, 28.16, 75.09, 23.56, 22.79, 14.09, 14.06, 11.51. HRMS (TOF-ESI$^+$) (m/z): C$_{53}$H$_{68}$N$_4$O$_6$S$_2$ calculated: 921.47 [M+H$^+$]; found: 921.49.

Trifluoroacetic acid (1.0 mL, 0.34 g, 3.73 mmol) was added dropwise to compound B (0.120 g, 0.13 mmol) in dichloromethane (10 mL). After stirring for 2 hours at room temperature, the reaction mixture was added dropwise to saturated aqueous sodium bicarbonate solution (20 mL), and extracted with dichloromethane (50 mL). The organic layer was washed with saturated aqueous sodium bicarbonate solution (30 mL) and saturated sodium chloride solution, and dried over anhydrous sodium sulfate. The solvent was evaporated in vacuo to obtain interested compound 1 as a dark purple solid.

$^1$H NMR (400 MHz, CDCl$_3$, 2515 K): δ 7.80 (d, J=8.5 Hz, 2H), 7.35 (ddd, J=8.2, 1.6, 0.4 Hz, 4H), 7.26 (d, J=8.5 Hz, 2H), 7.02 (ddd, J=8.7, 1.2, 0.4 Hz, 4H), 4.12 (d, J=7.0 Hz, 4H), 1.64 (m, 2H), 1.15-1.38 (m, 14H), 0.76-1.91 (m, 16H). $^{13}$C NMR (100 MHz, CDCl$_3$, 298 K): δ 172.83, 150.10, 148.85, 145.64, 133.63, 128.09, 127.67, 122.80, 121.45, 144.80, 100.02, 46.33, 38.65, 32.60, 32.11, 30.79, 29.64, 28.61, 25.09, 23.56, 22.79, 14.09, 14.06, 11.51, HRMS (TOF-ESI$^+$) (m/z): C$_{43}$H$_{52}$N$_4$O$_2$S$_2$ calculated: 721.36 [M+H$^+$]; found: 721.35.

(2) Preparation of Compound 1 Based Single Molecule Field Effect Transistor

Graphene was used as the gate electrode, and hafnium oxide with a thickness of 5 nm was used as the dielectric layer to construct a field effect transistor with a bottom gate structure.

First, the single-layer graphene grown by chemical vapor deposition was transferred onto a silicon wafer having a oxide layer of 300 nm, as the bottom gate.

A hafnium oxide layer with a thickness of 5 nm was deposited on the bottom gate by the sol-gel method.

A two-dimensional single-layer graphene with a nanogap was constructed on the dielectric layer to obtain a molecule device to be assembled.

A strongly-polarized molecule-graphene molecule heterojunction was constructed on the molecule device to be assembled to obtain a single molecule field effect transistor device. The specific process is as follows.

First, the compound of formula 1 and the carbodiimide dehydrator-activator 1-ethyl-3-(3-dimethylaminopropyl) carbodiimide hydrochloric acid (EDCI) were dissolved in pyridine. The concentrations were 10$^{-4}$ mol/L and 3×10$^{-3}$ mol/L, respectively. Then, the molecule device to be assembled was added into the above solution, and reacted for 48 h in argon atmosphere in dark. After that, the device was taken out of the solution, washed with acetone and ultrapure water three times, respectively, and dried with a nitrogen stream to obtain the compound 1 based single molecule field effect transistor.

It should be noted that the specific methods, conditions, parameters, and the like in the preparation process of the molecule device to be assembled can be implemented according to the methods in the relevant documents previously described herein, which will not be repeated in this application.

Example 2: Preparation of Compound 2 Based Single Molecule Field Effect Transistor (1) Synthesis of Compound 2

The synthetic route is as follows:

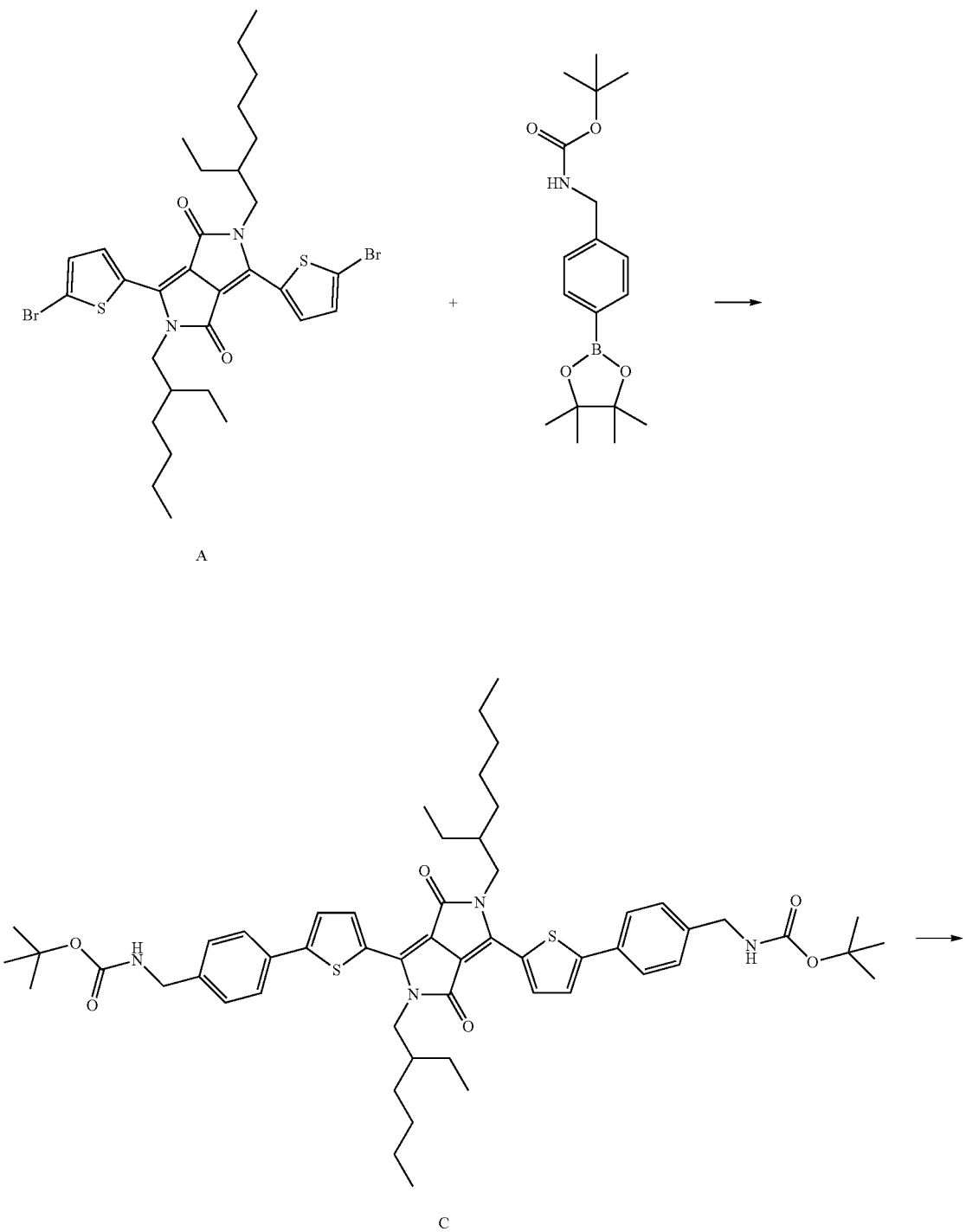

-continued

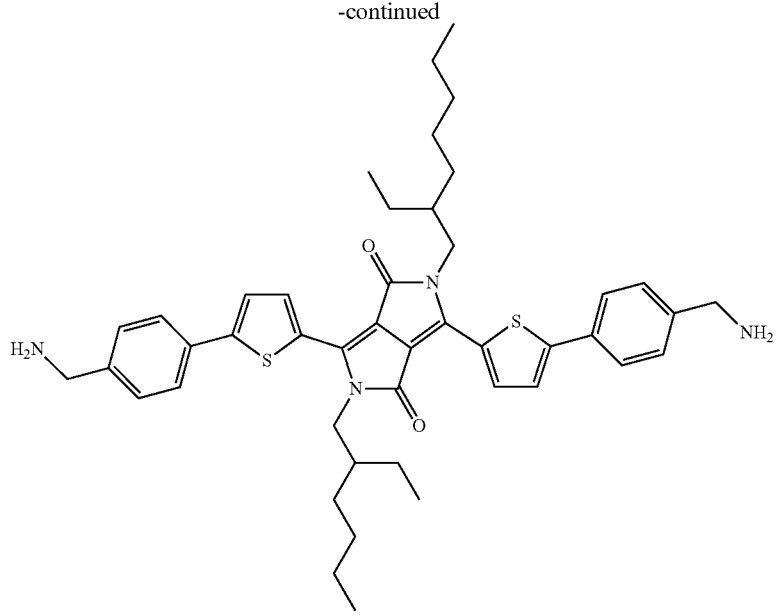

2

Compound A was synthesized according to the method of Example 1.

Compound A (697 mg, 1.00 mmol), 4-(N—Boc-aminomethyl)phenylboronic acid pinacol ester (734 mg, 2.20 mmol), bis(dibenzalacetone) palladium (18.4 mg, 20 μmop, tri(o-tolyl)phosphine (24.5 mg, 80.2 μmop, and anhydrous potassium carbonate (1.30 g, 9.43 mmol) were added to a 100 mL Schlenk bottle in sequence. After adding 2 drops of aliquat 336, 24 mL of toluene and 6 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). After the organic phases were combined and dried over anhydrous sodium sulfate, the solvent was removed under reduced pressure. The crude product was analyzed and purified by silica gel column chromatography to obtain compound C as a purple solid.

$^1$H NMR (400 MHz, CDCl$_3$, 298 K): δ 7.70 (d, J=8.6 Hz, 2H). 7.60-7.67 (m, 4H), 7.40 (ddd, J=8.5, 1.5, 0.5 Hz 6H), 4.32 (s, 4H), 4.12 (d, J=7.0 HZ, 4H), 1.54-1.76 (m 2H), 1.44 (s, 18H), 1.15-1.38 (m, 14H), 0.76-0.91 (m, 16H). $^{13}$C NMR (100 MHz, CDCl$_7$, 298 K): δ 172.83, 156.0.3, 148.85, 145.64, 143.21, 133.63, 133.12, 128.11, 127.67, 126.29, 121.45, 100.02, 79.66, 46.33, 43.70, 38.65, 32.60, 32.11, 30.79, 29.64, 28.61, 28.30, 25.09, 23.56, 22.79, 14.09, 14.06, 11.51. HRMS (TOF-ESI$^+$) (m/z): C$_{55}$H$_{72}$O$_6$S$_2$ calculated: 94). 50 [M+H$^+$]; found: 949.50.

The located reaction was carried out according to the method of Example 1, except that compound B was relocated with compound C (0.120 g, 0.13 mmol), to obtain the interested compound 2 as a dark purple solid.

$^1$H NMR (400 MHz, CDCl$_3$, 298 K): δ 7.70 (d, J=8.6 Hz, 2H), 7.63 (dd, J=6.5, 1.3 Hz, 4H), 7.38 (ddd, J=6.5, 1.3, 0.5 Hz, 6H), 4.10 (d, J=7.0 Hz, 4H), 3.67 (s, 4H), 1.54-4.76 (in, 2H), 1.15-1.38 (m, 14H), 0.76-0.91 (m, 16H). $^{13}$C NMR (100 MHz, CDCl$_3$, 298 K): δ 172.83, 148.85, 145.64, 141.15, 133.63, 133.34, 128.28, 127.67, 126.74, 121.45, 100.02, 46.33, 45.58, 38.65, 32.60, 32.11, 30.79, 29.64, 28.61, 25.09, 23.56, 22.79, 14.09, 14.06, 11.51. HRMS (TOF-ESI$^+$) (m/z): C$_{45}$H$_{56}$N$_4$O$_2$S$_2$ calculated: 749.39 [M+H$^+$]; found: 749.35.

(2) Preparation of Compound 2 Based Single Molecule Field Effect Transistor

A strongly-polarized molecule-graphene molecular heterojunction was constructed to obtain a compound 2 based field effect transistor with bottom gate structure according to the preparation method of transistor in Example 1, in which graphene was used as the gate electrode, hafnium oxide with a thickness of 5 nm was used as the dielectric layer, and compound 2 was used to replace compound 1.

Example 3: Preparation of Compound 3 Based Single Molecule Field Effect Transistor
(1) Synthesis of Compound 3
The synthetic route is as follows:
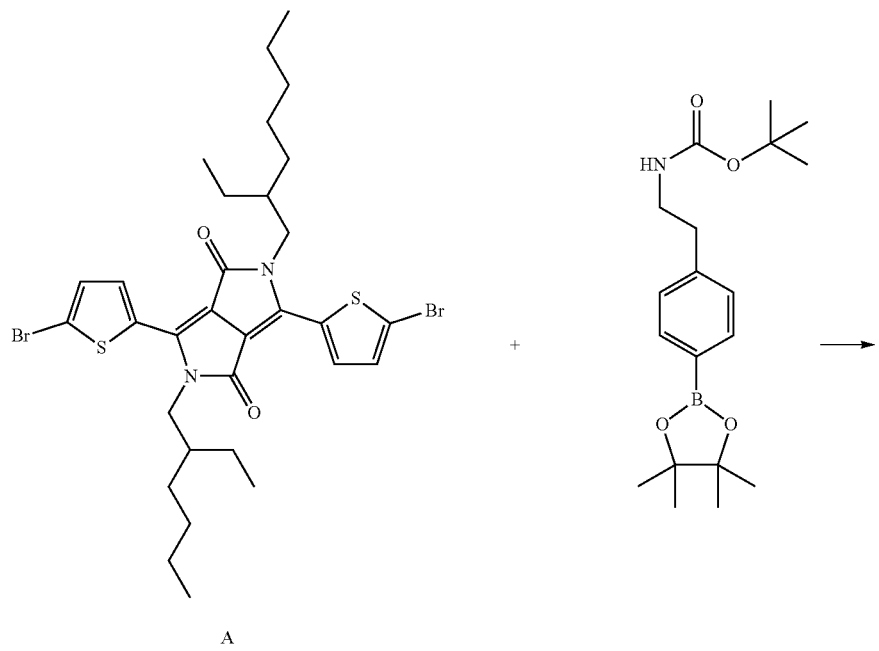
A
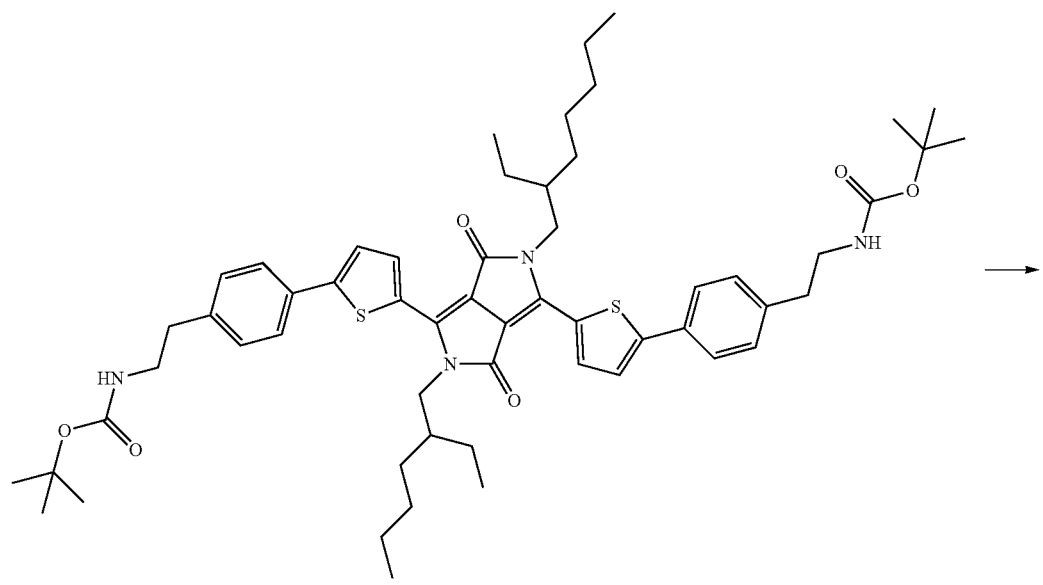
D -continued

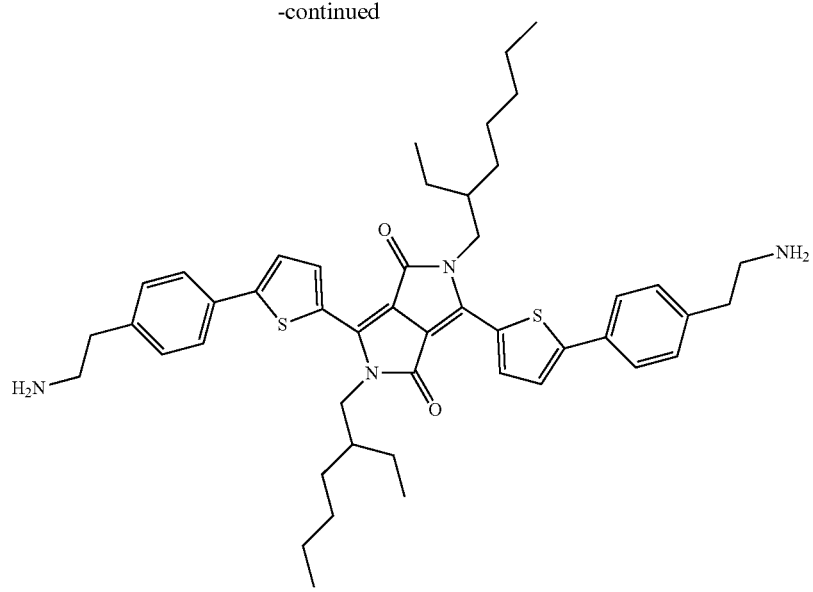

3

Compound A was synthesized according to the method of Example 1.

Compound A (843 mg, 1.21 mmol), 4-(N—Boc-aminomethyl)phenylboronic acid pinacol ester (924 mg, 2.66 mmol), bis(dibenzalacetone)palladium (22.3 mg, 24 μmop, tri(o-tolyl)phosphine (29.6 mg, 97.0 μmop, and anhydrous potassium carbonate (1.57 g, 11.41 mmol) were added to a 100 mL Schlenk bottle in sequence. After adding 2 drops of aliquat 336, 24 mL of toluene and 6 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). After the organic phases were and combined and dried over anhydrous sodium sulfate, the solvent was removed under reduced pressure. The crude product was analyzed and purified by silica gel column chromatography to obtain compound D as a purple solid.

$^1$H NMR (400 MHz, CDCl$_3$, 298 K): δ 7.72 (d, J=8.6 Hz, 2H), 7.64 (ddd, J=8.5, 1.5, 0.5 Hz, 4H), 7.39 (d, J=8.6 Hz, 2H), 7.19 (ddd, J=8.2, 1.5, 0.5 Hz, 4H), 4.13 (d, J=7.0 Hz, 4H), 3.50 (t, J=5.3 Hz, 4H), 2.55 (t, J=5.3 Hz, 4H), 1.54-1.76 (m, 2H), 1.43 (s, 18H), 1.15-1.38 (m, 14H), 0.76-0.91 (m, 16H). $^{13}$C NMR (100 MHz, CDCl$_3$, 298 K): δ 172.83, 156.24, 148.85, 145.64, 136.73, 133.63, 132.41, 128.18, 127.67, 126.64, 121.45, 100.02, 79.52, 46.33, 42.33, 38.65, 35.31, 32.60, 32.11, 30.79, 29.64, 28.61, 28.30, 25.09, 23.56, 22.79, 14.09, 14.06, 11.51. HRMS (TOF-ESI$^+$) (m/z): C$_{57}$H$_{76}$N$_4$O$_6$S$_2$ calculated: 977.53 [M+H$^+$]; found: 977.50.

The located reaction was carried out according to the method of Example 1, except that compound B was relocated with compound D (0.127 g, 0.13 mmol), to obtain the interested compound 3 as a dark purple solid.

$^1$H NMR (400 MHz, CDCl$_3$, 298 K): δ 7.72 (d, J=8.6 Hz, 2H), 7.63 (ddd, J=8.5, 1.5, 0.5 Hz, 4H), 7.38 (d, J=8.6 Hz, 2H), 7.17 (ddd, J=8.1, 1.5, 0.5 Hz, 4H), 4.10 (d, J=7.0 Hz, 4H), 2.76 (t, J=6.6 Hz, 4H), 2.49 (t, J=6.6 Hz, 4H), 1.54-1.76 (m, 211), 1.15-1.38 (m, 14H), 0.76-0.91 (m, 16H). $^{13}$C NMR (100 MHz, CDCl$_3$, 298 K): δ 172.83, 148.85, 145.64, 136.83, 133.63, 132.36, 127.92, 127.67, 126.58, 121.45, 100.02, 46.33, 42.84, 38.87, 38.65, 32.60, 32.11, 30.79, 29.64, 28.61, 25.09, 23.56, 22.79, 14.09, 14.06, 11.51. HRMS (TOF-ESI$^+$) (m/z): C$_{47}$H$_{60}$N$_4$O$_2$S$_2$ calculated: 777.42 [M+H$^+$]; found. 777.42.

(2) Preparation of Compound 3 Based Single Molecule Field Effect Transistor

A strongly-polarized molecule-graphene molecular heterojunction was constructed to obtain a compound 3 based field effect transistor with bottom gate structure according to the preparation method of transistor in Example 1, in which graphene was used as the gate electrode, hafnium oxide with a thickness of 5 nm was used as the dielectric layer, and compound 3 was used to replace compound 1.

Example 4: Preparation of Compound 4 Based Single Molecule Field Effect Transistor
(1) Synthesis of Compound 4
The synthetic route was as follows.
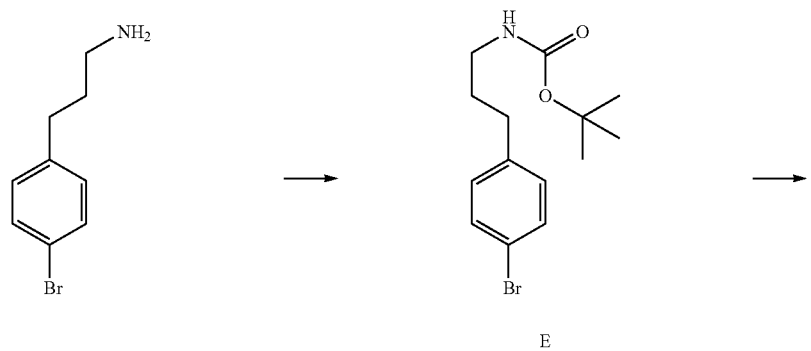
E
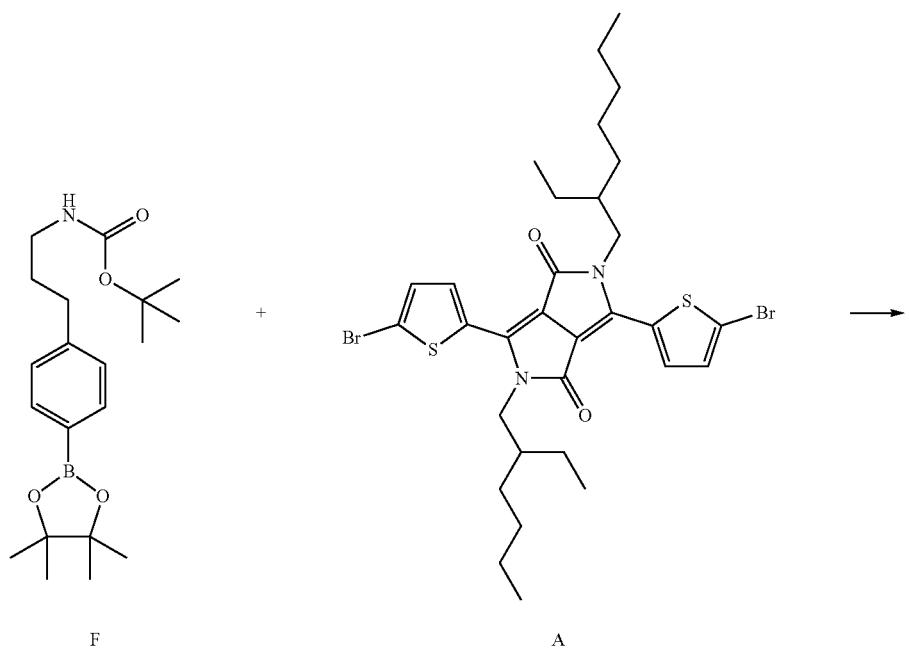
F   +   A -continued

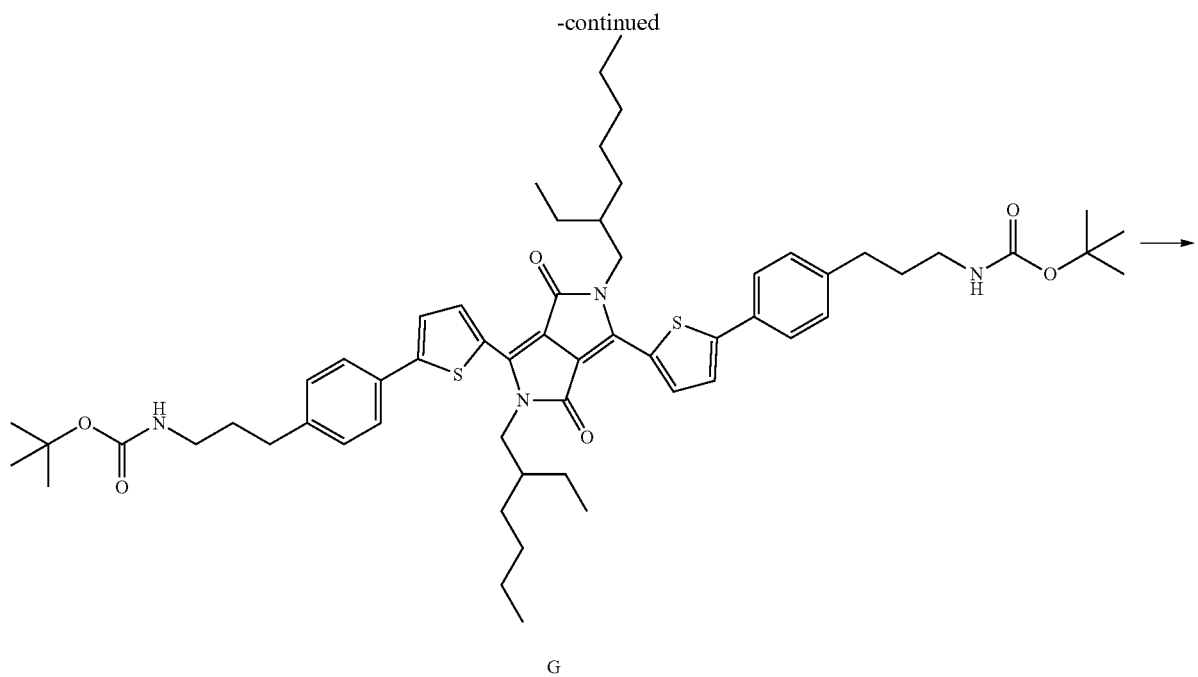

G

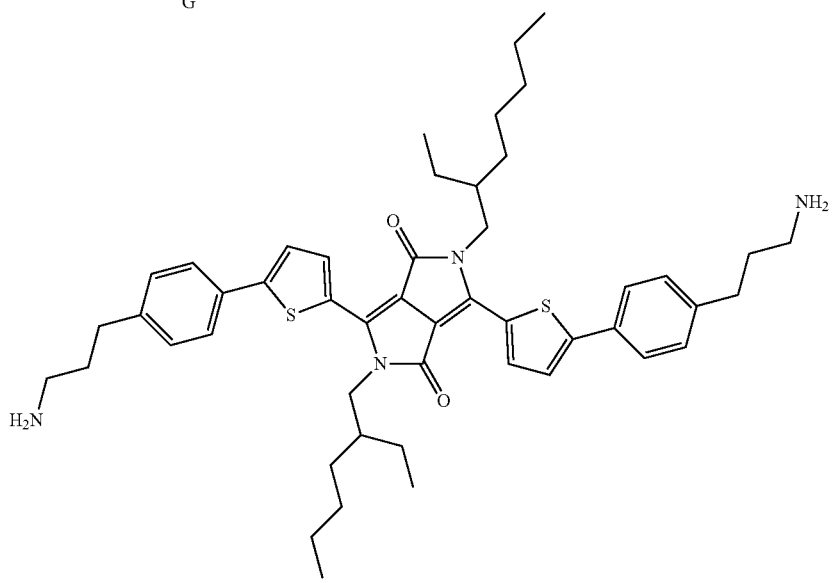

4

Dichloromethane (15 mL), p-bromoamphetamine (1.293 g, 6.04 mmol) and triethylamine (944 mg, 1.3 mL, 9.33 mmol) were added into a 50 mL reaction flask under the protection of argon, and the reaction flask was located in an ice-water bath. Di-tert-butyl dicarbonate (1.61 g, 1.7 mL, 7.40 mmol) was added dropwise with stirring, allowed to warm to room temperature, and reacted for 4 h. After that, the reaction solution was poured into dichloromethane (30 mL) and washed with water (2×20 mL) and saturated sodium chloride solution (20 mL), and then dried over anhydrous sodium sulfate. The solvent was removed under reduced pressure. The crude product was analyzed and purified by silica gel column chromatography to obtain compound E as a colorless oily liquid.

$^1$H NMR (400 MHz, CDCl$_3$, 298 K): δ 7.45-7.39 (m, 2H), 7.12-7.06 (m, 2H), 3.24 (t, J=5.0 Hz, 2H), 2.61-2.53 (m, 2H), 1.77 (tt, J=8.0, 5.0 Hz, 2H), 1.44 (s, 9H). $^{13}$C NMR (100 MHz, CDCl$_3$, 298 K): δ 156.19, 140.06, 131.22, 129.96, 119.50, 79.52, 40.56, 33.48, 30.67, 28.30. HRMS (TOF-ESI$^+$) (m/z): C$_{14}$H$_{20}$BrNO$_2$ calculated 314.07 [M+H$^+$]; found: 314.01.

Compound E (1.02 g, 3.26 mmol), pinacol diborate (993 mg, 3.91 mmol), palladium tetrakis(triphenylphosphine) (151 mg, 0.13 mmol), and potassium acetate (1.60 g, 16.30 mmol) were added to a 100 mL Schlenk bottle in sequence, and then 50 mL of N,N-dimethylformamide was added. The resultant was circulated 3 times by a freezing and thawing pump circulation method to remove oxygen, and then heated and stirred at 90° C. under the protection of argon for 10 h. After cooling, the reaction mixture was poured into water (50 mL) and extracted with dichloromethane (3×30 mL).

The organic phase was washed with water (3×30 mL) and saturated sodium chloride solution (30 mL) in turn, and dried with anhydrous sodium sulfate. The solvent was removed under reduced pressure. The crude product was analyzed and purified by silica gel column chromatography to obtain compound F as a colorless oily liquid.

$^1$H NMR (400 MHz, CDCl$_3$, 298 K): δ 7.57-7.51 (m, 2H), 7.08 (dt, J=7.4, 1.0 Hz, 2H), 5.94 (t, J=6.4 Hz, 2H), 3.17 (td, J=7.1, 6.4 Hz, 2H), 2.66 (tt, J=7.1, 1.0 Hz, 2H), 1.83 (p, J=7.1 Hz, 2H), 1.42 (s, 9H), 1.24 (s, 9H). $^{13}$C NMR (100 MHz, CDCl$_3$, 298 K): δ 156.63, 143.39, 134.66, 134.61, 126.72, 84.02, 79.63, 39.62, 33.32, 29.09, 29.05, 24.82. HRMS (TOF-ESI$^+$) (m/z): C$_{20}$H$_{32}$BNO$_4$ calculated. 362.25 [M+H$^+$], found: 362.29.

Compound A (843 mg, 1.21 mmol), compound F (965 mg, 2.66 mmol), bis(dibenzalacetone) palladium (22.3 mg, 24 μmol), tri(o-tolyl)phosphine (29.6 mg, 97.0 μmol), and anhydrous potassium carbonate (1.57 g, 11.41 mmol) were added to a 100 mL Schlenk bottle in sequence. After adding 2 drops of aliquat 336, 24 mL of toluene and 6 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). After the organic phases were combined and dried over anhydrous sodium sulfate, the solvent was removed under reduced pressure. The crude product was analyzed and purified by silica gel column chromatography to obtain compound G as a purple solid.

$^1$H NMR (400 MHz, CDCl$_3$, 298 K): δ 7.76 (d, J=8.6 Hz, 2H), 7.59-7.66 (m, 4H), 7.39 (dd, J=24.6, 7.5 Hz, 2H), 7.16 (ddd, J=8.2, 1.5, 0.5 Hz, 4H), 4.11 (d, J=6.9 Hz, 4H), 3.19 (t, J=6.4 Hz, 4H), 2.39 (t, J=6.8 Hz, 4H), 1.84-2.03 (m, 4H), 1.54-1.76 (m, 2H), 1.43 (s, 18H), 1.15-1.38 (m, 14H), 0.76-0.91 (m, 16H). $^{13}$C NMR (100 MHz, CDCl$_3$, 298 K): δ 172.83, 156.19, 148.85, 145.64, 141.66, 133.63, 132.81, 128.37, 127.67, 126.29, 121.45, 100.02, 79.52, 46.33, 40.56, 38.65, 33.48, 32.60, 32.11, 30.79, 30.67, 29.64, 28.61, 28.30, 25.09, 23.56, 22.79, 14.09, 14.06, 11.51. HRMS (TOF-ESI$^+$) (m/z): C$_{59}$H$_{80}$N$_4$O$_6$S$_2$ calculated: 1005.55 [M+H$^+$]; found: 1005.55.

The located reaction was carried out according to the method of Example 1, except that compound B was relocated with compound G (0.131 g, 0.13 mmol), to obtain the interested compound 4 as a dark purple solid.

$^1$H NMR (400 MHz, CDCl$_3$, 298 K): δ 7.72 (d, J=8.6 Hz, 2H), 7.63 (ddd, J=J=8.5, 1.5, 0.5 Hz, 4H), 7.40 (d, J=8.6 Hz, 2H), 7.12-7.19 (m, 4H), 4.07-4.15 (m, 4H), 2.60-2.68 (m, 4H), 2.29-2.37 (t, J=6.6 Hz, 4H), 1.54-1.94 (m, 6H), 1.15-1.38 (m, 14H), 0.76-0.91 (m, 16H). $^{13}$C NMR (100 MHz, CDCl$_3$, 298 K): δ 172.83, 148.85, 145.64, 141.66, 133.63, 132.81, 128.37, 127.67, 126.29, 121.45, 100.02, 46.33, 41.70, 38.65, 33.53, 33.05, 32.60, 32.11, 30.79, 29.64, 28.61, 25.09, 23.56, 22.79, 14.09, 14.06, 11.51. HRMS (TOF-ESI$^+$) (m/z): calculated: 805.45 [M+H$^+$]; found: 805.42.

(2) Preparation of Compound 4 Based Single Molecule Field Effect Transistor

A strongly-polarized molecule-graphene molecular heterojunction was constructed to obtain a compound 4 based field effect transistor with bottom gate structure according to the preparation method of transistor in Example 1, in which graphene was used as the gate electrode, hafnium oxide with a thickness of 5 nm was used as the dielectric layer, and compound 4 was used to replace compound 1.

Example 5: Preparation of Compound 5 Based Single Molecule Field Effect Transistor (1) Synthesis of Compound 5
The synthetic route is as follows:

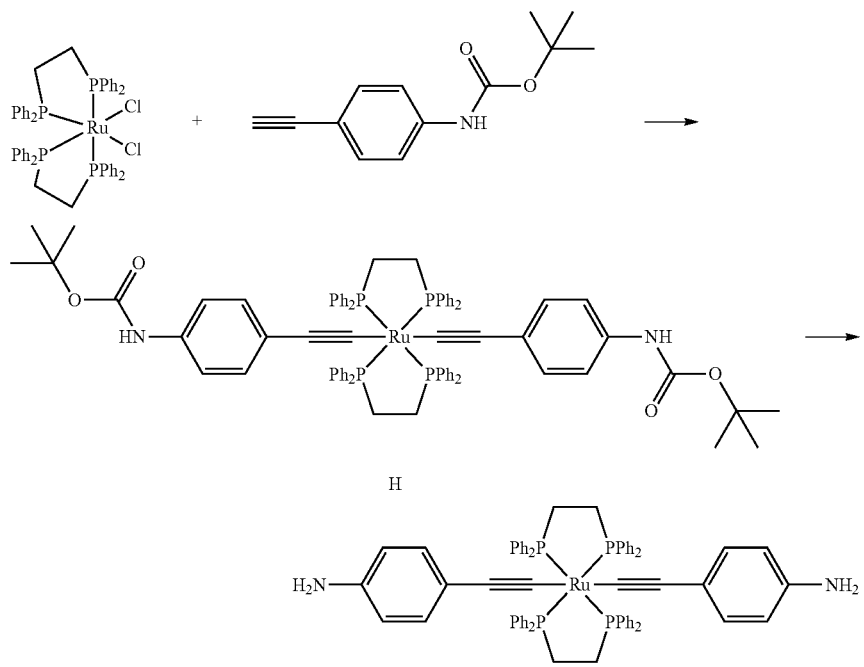

5

Bis[1,2-bis(diphenylphosphine)ethane]ruthenium dichloride (223 mg, 0.23 mmol), N—Boc-4-ethynylaniline (150 mg, 0.69 mmol), and sodium hexafluorophosphate (154 mg, 0.92 mmol) were added to a 50 mL Schlenk bottle, which was then dissolved in dry dichloromethane (15 mL). Triethylamine (0.190 mL) was added drop wise to the above reaction solution under the protection of argon, which was then reacted at 35° C. with stirring for 24 h. After the reaction was completed, the reaction mixture was filtered. The solvent was removed under reduced pressure. The obtained solid was washed with n-pentane (25 mL). The crude product was analyzed and purified by silica gel column chromatography to obtain compound H as a yellow solid.

$^{31}$P NMR (162 MHz, CDCl$_3$, 298 K): δ 53.4. $^1$H NMR (400 MHz, CDCl$_3$, 298 K): δ 6.98-7.55 (m, 48H), 2.45 (m, 8H), 1.50 (s, 18H). $^{13}$C NMR (100 MHz, CDCl$_3$, 298 K): δ 195.14, 138.85, 132.99, 131.93, 131.20, 131.08, 128.13, 121.56, 119.15, 116.90, 79.54, 30.23, 25.43, HRMS (TOF-ESI+) (m/z): C$_{78}$H$_{76}$N$_2$O$_4$P$_4$Ru calculated. 1331.44[M+H$^+$]; found: 1331.39.

Trifluoroacetic acid (1.0 mL, 0.34 g, 3.73 mmol) was added drop wise to compound H (0.173 g, 0.13 mmol) in dichloromethane (10 mL). After stirring for 20 hours at room temperature, the reaction mixture was added dropwise to saturated aqueous sodium bicarbonate solution (20 mL), and extracted with dichloromethane (50 mL). The organic layer was washed with saturated aqueous sodium bicarbonate solution (30 mL) and saturated sodium chloride solution, and dried over anhydrous sodium sulfate. The solvent was evaporated in vacuo to obtain interested compound 5 as a yellow solid.

$^{31}$P NMR (162 MHz, CDCl$_3$, 298 K): d=53.4 $^1$H NMR (400 MHz, CDCl$_3$, 298 K): δ 6.98-7.55 (m, 48H), 2.45 (m, 8H). $^{13}$C NMR (100 MHz, CDCl$_3$, 298 K): δ 148.85, 132.99, 131.93, 131.20, 131.08, 128.13, 121.56, 119.15, 116.90, 24.96. HRMS (TOF-ESI+) (m/z): C$_{68}$H$_{60}$N$_2$P$_4$Ru calculated 0.1131.28 [M+H$^+$]; found: 1131.29.

(2) Preparation of Compound 5 Based Single Molecule Field Effect Transistor

A strongly-polarized molecule-graphene molecular heterojunction was constructed to obtain a compound 5 based field effect transistor with bottom gate structure based on compound 5 with reference to the preparation method of transistor in Example 1, in which graphene was used as the gate electrode, hafnium oxide with a thickness of 5 nm was used as the dielectric layer, and compound 5 was used to replace compound 1.

Example 6: Preparation of Compound 6 Based Single Molecule Field Effect Transistor (1) Synthesis of Compound 6
The synthetic route is as follows:

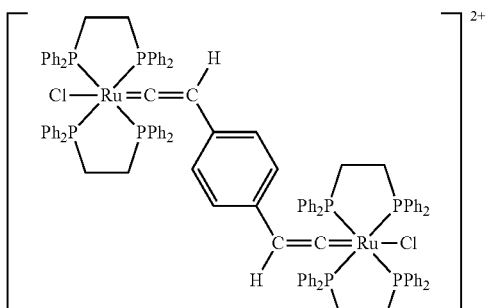

I

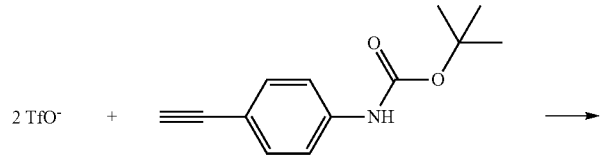

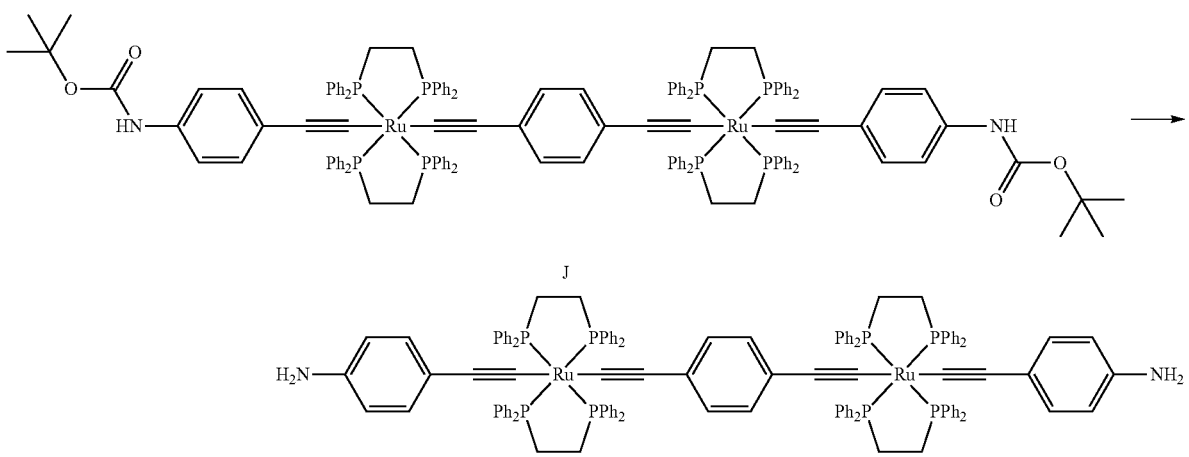

J

Compound I was synthesized according to the method described in the literature (*New J. Chem.*, 2011, 35, 2105-2113).

Compound I (527 mg, 0.23 mmol), N—Boc-4-ethynylaniline (150 mg, 0.69 mmol), and sodium hexafluorophosphate (154 mg, 0.92 mmol) were added to a 50 mL Schlenk bottle, which was then dissolved in dry dichloromethane (15 mL). Triethylamine (0.190 mL) was added dropwise to the above reaction solution under the protection of argon, which was then reacted at 35° C. with stirring for 48 h. After the reaction was completed, the reaction mixture was filtered. The solvent was removed under reduced pressure. The obtained solid was washed with n-pentane (25 mL). The crude product was analyzed and purified by silica gel column chromatography to obtain compound J as a yellow solid.

$^{31}$P NMR (162 MHz, CDCl$_3$, 298 K): δ 54.9. $^1$H NMR (400 MHz, CDCl$_3$, 298 K): δ 6.98-7.55 (m, 92H), 2.45 (m, 16H), 1.50 (s, 18H). $^{13}$C NMR (100 MHz, CDCl$_3$, 298 K): δ 195.14, 138.85, 137.24, 132.99, 131.93, 131.20, 131.08, 128.13, 125.60, 121.56, 119.15, 116.90, 79.54, 30.23, 25.43, HRMS (TOF-ESI+) (m/z): C$_{140}$H$_{128}$N$_2$O$_4$P$_8$Ru$_2$ calculated. 2353.59 [M+H]$^+$; found: 2353.50.

The reaction was carried out located according to the method of Example 5, except that compound H was relocated with compound J (0.306 g, 0.13 mmol, to obtain the interested compound 6 as a yellow solid.

$^{31}$P NMR (162 MHz, CDCl$_3$, 298 K): d=55.4 $^1$H NMR (400 MHz, CDCl$_3$, 298 K): δ 6.98-7.55 (m, 92H), 2.45 (m, 16H). $^{13}$C NMR (100 MHz, CDCl$_3$, 298 K): δ 150.20, 137.39, 137.23, 132.46, 132.41, 123.20, 122.20, 117.38, 113.78, 103.62, 133.05, 132.92, 128.47, 128.42, 24.96; HRMS (TOF-ESI+) (m/z): C$_{130}$H$_{112}$N$_2$P$_8$Ru$_2$ calculated: 2153.48 [M+H$^+$]; found: 2153.49.

(2) Preparation of Compound 6 Based Single Molecule Field Effect Transistor

A strongly-polarized molecule-graphene molecular heterojunction was constructed to obtain a compound 6 based field effect transistor with bottom gate structure according to the preparation method of transistor in Example 1, in which graphene was used as the gate electrode, hafnium oxide with a thickness of 5 nm was used as the dielectric layer, and compound 6 was used to replace compound 1.

Example 7: Preparation of Compound 7 Based Single Molecule Field Effect Transistor (1) Synthesis of Compound 7
The synthetic route is as follows:

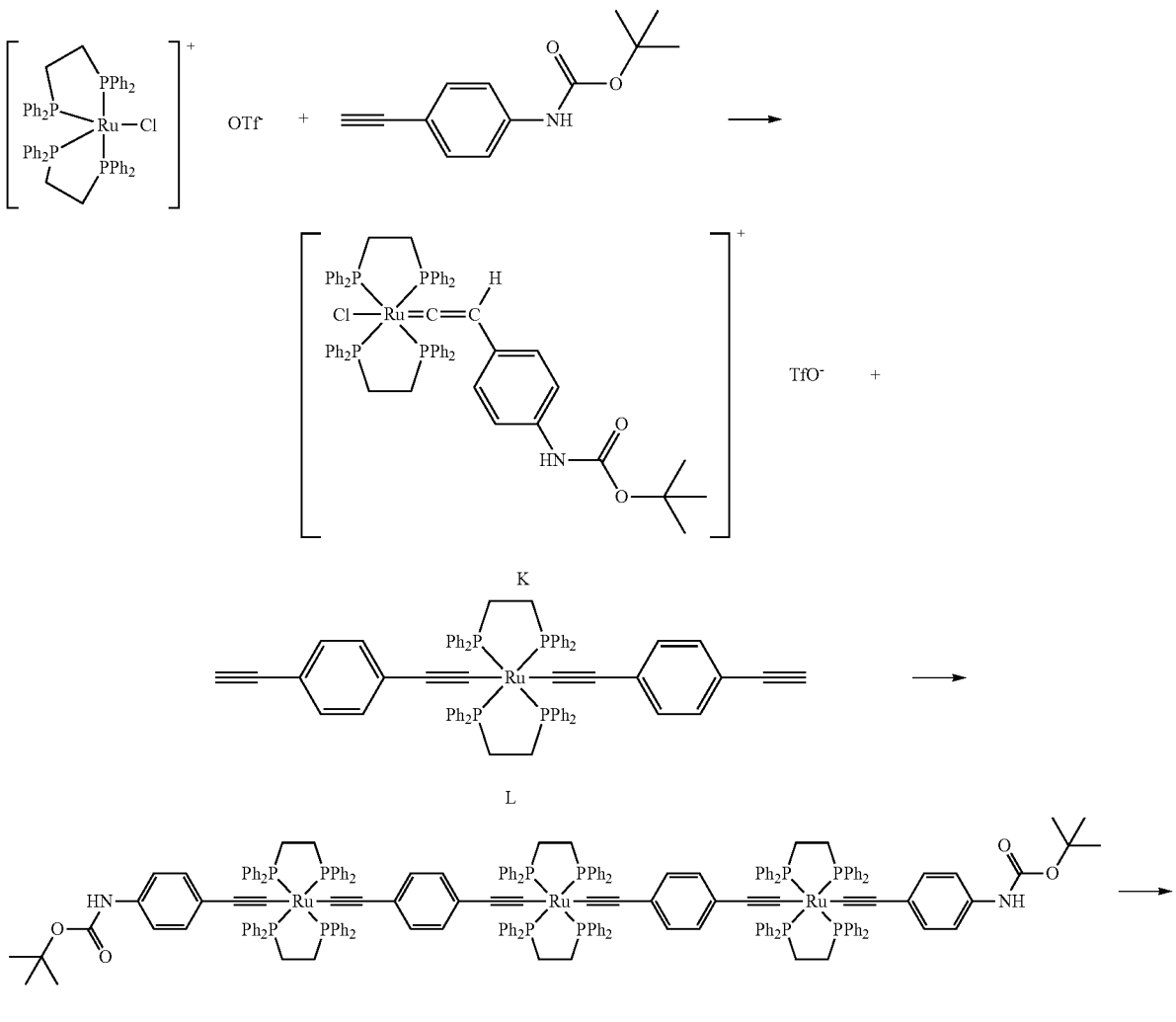

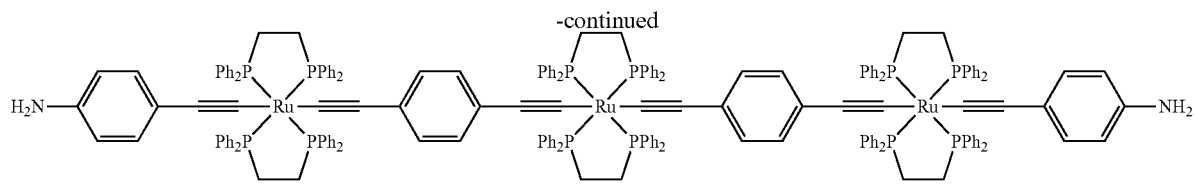

7

Bis[1,2-bis(diphenylphosphine)ethane] ruthenium chloride triflate (825 mg, 0.75 mmol) and N—Boc-4-ethynylaniline (330 mg, 1.52 mmol) were added to a 100 mL Schlenk bottle, and dissolved in 40 mL of dichloromethane. The reaction was stirred at room temperature under the protection of argon for 6 h, and then filtered. The solvent of the filtrate was removed under reduced pressure. The resulting precipitate was washed with ether (4×30 mL) to obtain compound K as a dark green solid.

$^{31}$P NMR (162 MHz, CDCl$_3$, 298 K): δ 38.2. $^1$H NMR (400 MHz, CDCl$_5$, 298 K): δ 7.51-7.05 (m, 40H), 6.55 (d, J=7.8 Hz, 2H), 5.64 (d, J=8.0 Hz, 2H), 4.10 (s, 1H), 2.92 (m, 8H), 1.50 (s, 18H). $^{13}$C NMR (100 MHz, CDCl$_3$, 298 K): δ 354.27, 194.75, 137.24, 132.99, 131.93, 131.20, 131.08, 128.13, 125.60, 124.93, 120.4, 108.98, 79.54, 30.23, 28.68. HRMS (TOF-ESI+) (m/z): C$_{66}$H$_{63}$ClF$_3$NO$_5$P$_4$RuS calculated: 1300.21 [M+H]$^+$; found: 1300.20.

Compound L was synthesized according to the method described in the literature (*New J. Chem.*, 2011, 35, 2105-2113).

Compound K (338 mg, 0.26 mmol), Compound L (149 mg, 0.13 mmol), sodium hexafluorophosphate (88 mg, 0.2 mmol) were added to a 50 mL Schlenk bottle, and then dissolved in dry dichloromethane (30 mL). Triethylamine (0.150 mL) was added dropwise to the above reaction solution under the protection of argon, which was then reacted at 35° C. with stirring for 96 h. After the reaction was completed, the reaction mixture was filtered. The solvent was removed under reduced pressure. The obtained solid was washed with n-pentane (25 mL). The crude product was analyzed and purified by silica gel column chromatography to obtain compound M as a yellow solid.

$^{31}$P NMR (162 MHz, CDCl$_3$, 298 K): δ 54.89. $^1$H NMR (400 MHz, CDCl$_3$, 298 K): δ 6.98-7.55 (m, 136H), 2.45 (m, 24H), 1.50 (s, 18H). $^{13}$C NMR (100 MHz, CDCl$_3$, 298 K): δ 195.14, 137.95-126.92, 119.15, 118.42, 116.90, 79.54, 30.23, 25.43, HRMS (TOF-ESI+) (m/z): C$_{202}$H$_{180}$N$_2$O$_4$P$_{12}$Ru$_3$ calculated: 3375.79 [M+H]$^+$; found: 3375.70.

The reaction was carried out located according to the method of Example 5, except that compound H was relocated with compound M (0.439 g, 0.13 mmol), to obtain the interested compound 7 as a yellow solid.

$^{31}$P NMR (162 MHz, CDCl$_3$, 298 K): d=55.00, $^{13}$C NMR (400 MHz, CDCl$_3$, 298 K): δ 6.98-7.55 (m, 136H), 2.45 (m, 24H). $^{13}$C NMR (100 MHz, CDCl$_3$, 298 K): δ 195.14, 137.95-126.92, 119.15, 118.42, 116.90, 25.43; HRMS (TOF-ESI+) (m/z): C$_{192}$H$_{164}$N$_2$P$_{12}$Ru$_3$ calculated: 3175.68 [M+H]$^+$; found: 3175.68.

(2) Preparation of Compound 7 Based Single Molecule Field Effect Transistor

A strongly-polarized molecule-graphene molecular heterojunction was constructed to obtain a compound 7 based field effect transistor with bottom gate structure according to the preparation method of transistor in Example 1, in which graphene was used as the gate electrode, hafnium oxide with a thickness of 5 nm was used as the dielectric layer, and compound 7 was used to replace compound 1.

Example 8: Preparation of Compound 8 Based Single Molecule Field Effect Transistor (1) Synthesis of Compound 8
The synthetic route is as follows:

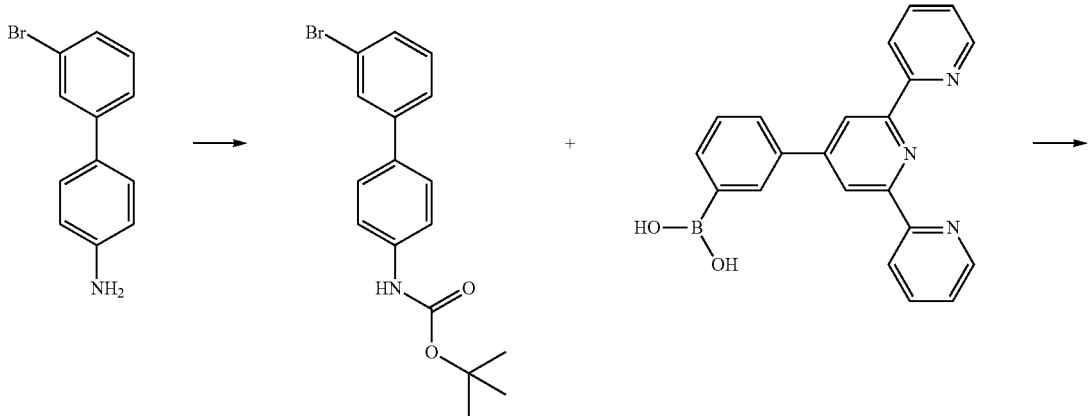

N          O

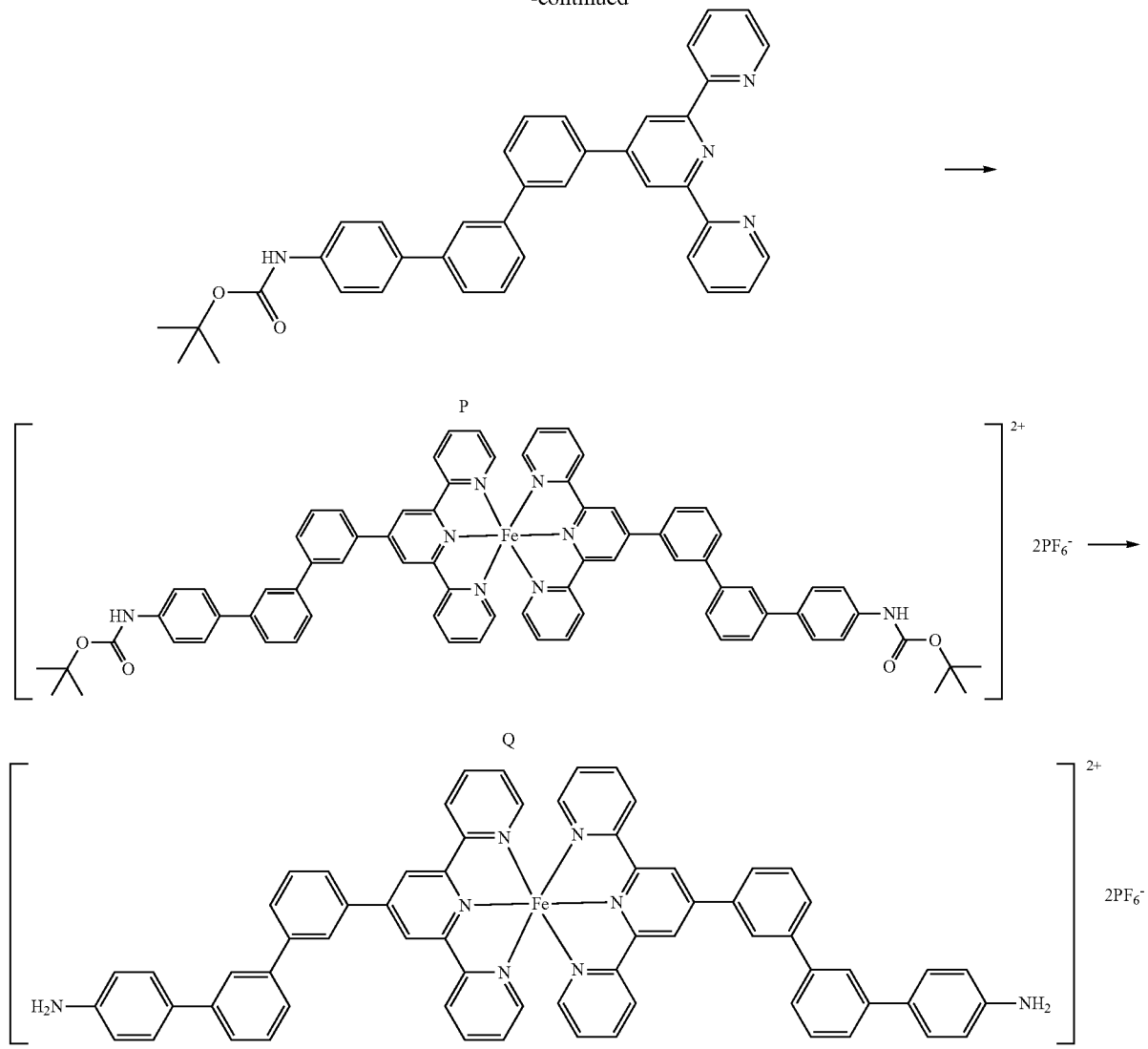

Dichloromethane (15 mL), 3-bromo-4'-aminobiphenyl (1.499 g, 6.04 mmol) and triethylamine (944 mg, 1.3 mL, 9.33 mmol) were added into a 50 mL reaction flask under argon protection, and the reaction flask was located in an ice-water bath. Di-tert-butyl dicarbonate (1.61 g, 1.7 mL, 7.40 mmol) was added dropwise with stirring, allowed to warm to room temperature, and reacted for 4 h. After that, the reaction solution was poured into dichloromethane (30 mL) and washed with water (2×20 mL) and saturated sodium chloride solution (20 mL) in turn, and then dried over anhydrous sodium sulfate. The solvent was removed under reduced pressure. The crude product was analyzed and purified by silica gel column chromatography to obtain compound N as a white solid.

$^1$H NMR (400 MHz, CDCl$_3$, 298 K): δ 7.78 (t, J=2.0 Hz, 1H), 7.72-7.65 (m, 2H), 7.62 (dt, J=7.5, 2.0 Hz, 1H), 7.53 (dq, J=8.2, 2.1 Hz, 3H), 7.31 (t, J=7.5 Hz, 1H), 6.57 (s, 1H), 1.50 (s, 9H). $^{13}$C NMR (100 MHz, CDCl$_3$, 298 K): δ 153.93, 143.4.3, 137.44, 136.75, 131.50, 130.90, 130.48, 127.82, 126.46, 126.38, 123.40, 80.43, 28.16. HRMS (TOF-ESI$^+$) (m/z): C$_{17}$H$_{18}$BrNO$_2$ calculated. 348.06 [M+H$^+$]; found: 348.06.

Compound O was synthesized according to the method described in the literature (J. Am. Chem. Soc. 2014, 136, 8165-8168).

Compound N (428 mg, 1.23 mmol), compound O (477 mg, 1.35 mmol), tetrakis(triphenylphosphine) palladium (14.6 mg, 12.3 μmol), and anhydrous potassium carbonate (1.60 g, 11.6 mmol) were added to a 100 mL Schlenk bottle in sequence, and then 25 mL of tetrahydrofuran and 5 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). After the organic phases were combined and dried over anhydrous sodium sulfate, the solvent was removed under reduced pressure. The crude product was analyzed and purified by silica gel column chromatography to obtain compound P as a white solid.

$^1$H NMR (400 MHz, CDCl$_3$, 298 K): δ 8.58 (dd, J=10.2, 1.1 Hz, 2H), 8.55-8.48 (m, 4H), 8.08 (t, J=2.0 Hz, 1H), 8.01 (t, J=2.0 Hz, 1H), 7.80-7.55 (m, 10H), 7.48 (td, J=7.9, 1.2 Hz, 2H), 6.93 (ddd, J=8.0, 5.1, 1.1 Hz, 2H), 6.59 (s, 1H), 1.50 (s, 9H). $^{13}$C NMR (100 MHz, CDCl$_3$, 298 K): δ 156.38, 155.79, 153.93, 149.14, 147.56, 142.54, 140.08, 139.77, 138.84, 137.44, 136.75, 136.59, 129.45, 129.37, 129.27, 128.17, 128.05, 127.82, 127.76, 126.46, 125.60, 124.02, 121.39, 120.06, 80.43, 28.16. HRMS (TOF-ESI$^+$) (m/z): C$_{38}$H$_{32}$N$_4$O$_2$ calculated. 577.26 [M+H$^+$]; found: 577.26.

Methanol (10 mL) was added to a 50 mL reaction flask to dissolve compound P (182 mg, 0.316 mmol). After that, ferrous chloride (21 mg, 0.158 mmol) in methanol (10 mL) was added dropwise, and the reactant was stirred and refluxed under the protection of argon for 4 h. Then the reactant was cooled to room temperature, and an excess of saturated ammonium hexafluorophosphate in methanol was added dropwise until the precipitation was completely precipitated, which was filtered. The obtained solid was rinsed with distilled water (2×10 mL) and ether (2×10 mL) in turn. The crude product was recrystallized with a mixed solvent of acetonitrile and acetone to obtain compound Q as a purple solid.

$^1$H NMR (400 MHz, CDCl$_3$, 298 K): δ 8.85 (dd, J=7.5, 1.4 Hz, 4H), 8.69 (d, J=8.0 Hz, 8H), 8.04 (t, J=2.0 Hz, 4H), 7.76 (dd, J=8.1, 6.7 Hz, 4H), 7.71-7.49 (m, 20H), 7.00 (td, J=7.4, 1.6 Hz, 4H), 1.50 (s, 18H). $^{13}$C NMR (100 MHz, CDCl$_3$, 298 K): δ 195.12, 155.16, 153.93, 152.39, 150.10, 149.69, 142.54, 140.08, 139.77, 138.84, 138.67, 137.44, 136.75, 129.45, 129.37, 129.27, 128.17, 128.05, 127.82, 127.76, 126.46, 125.60, 125.08, 122.82, 80.43, 28.16. HRMS (TOF-ESI$^+$) (m/z): C$_{76}$H$_{64}$FeN$_8$O$_4$ calculated: 1029.44 [M−2PF$_6^-$+H$^+$]; found. 1029.44.

Trifluoroacetic acid (1.0 mL, 0.34 g, 3.73 mmol) was added dropwise to compound Q (0.135 g, 0.13 mmol) in dichloromethane (10 mL). After stirring for 20 hours at room temperature, the reaction mixture was added dropwise to saturated aqueous sodium bicarbonate solution (20 mL), and extracted with dichloromethane (50 mL). The organic layer was washed with saturated aqueous sodium bicarbonate solution (30 mL) and saturated sodium chloride solution, and dried over anhydrous sodium sulfate. The solvent was evaporated in vacuo to obtain interested compound 8 as a purple solid.

$^1$H NMR (400 MHz, CDCl$_3$, 298 K): δ 8.43-8.52 (m, 12H), 8.05 (t, J=2.0 Hz, 2H), 7.97 (t, J=2.0 Hz, 2H), 7.79-7.58 (m, 12H), 7.48 (td, J=8.0, 1.3 Hz, 4H), 7.31-7.25 (m, 4H), 6.93 (ddd, J=8.0, 5.1, 1.1 Hz, 4H), 6.79-6.73 (m, 4H). $^{13}$C NMR (100 MHz, CDCl$_3$, 298 K) δ 156.38, 155.79, 149.14, 148.03, 147.56, 142.54, 140.08, 139.77, 138.84, 136.59, 134.36, 129.45, 129.37, 129.27, 128.17, 128.15, 128.05, 127.76, 125.60, 124.02, 121.39, 120.06, 115.37. HRMS (TOF-ESI$^+$) (m/z): C$_{66}$H$_{48}$FeN$_8$ calculated: 1009.34 [M−2PF$_6^-$+H$^+$], found: 1009.34.

(2) Preparation of Compound 8 Based Single Molecule Field Effect Transistor

A strongly-polarized molecule-graphene molecular heterojunction was constructed to obtain a compound 8 based field effect transistor with bottom gate structure according to the preparation method of transistor in Example 1, in which graphene was used as the gate electrode, hafnium oxide with a thickness of 5 nm was used as the dielectric layer, and compound 8 was used to replace compound 1.

Example 9: Preparation of Compound 9 Based Single Molecule Field Effect Transistor (1) Synthesis of Compound 9
The synthetic route is as follows:

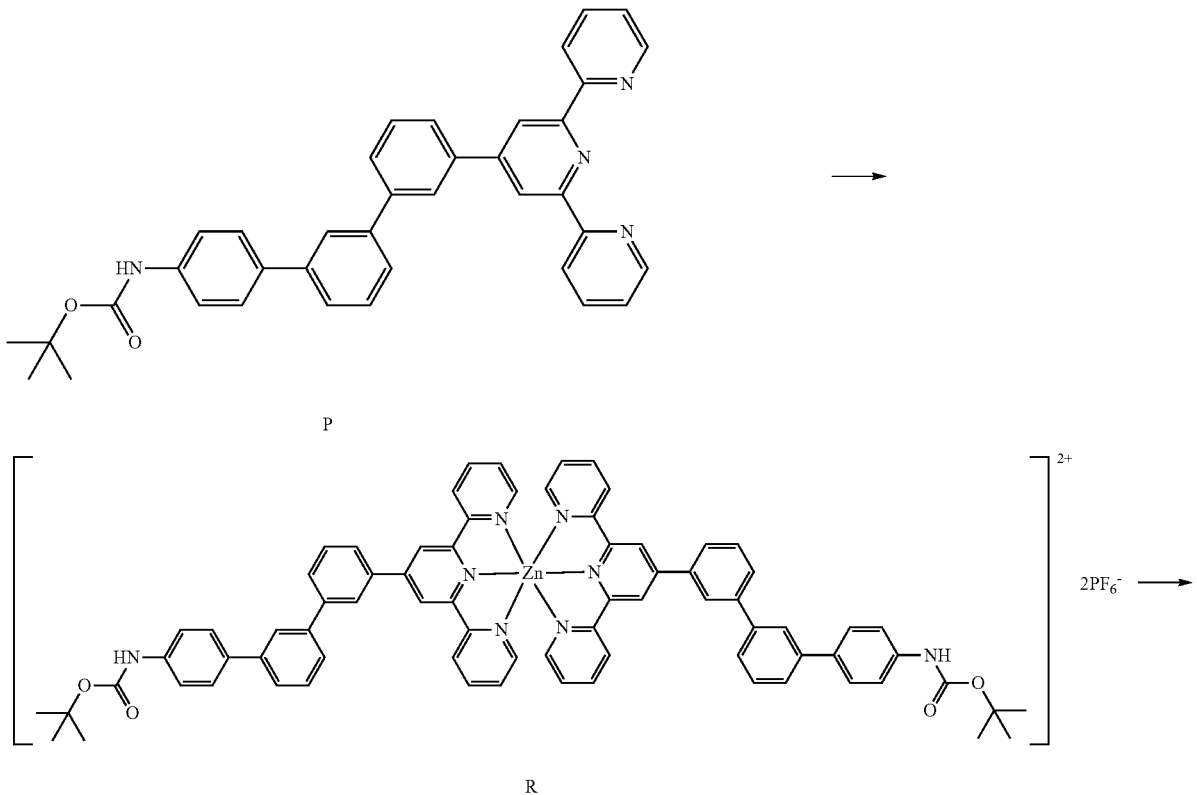

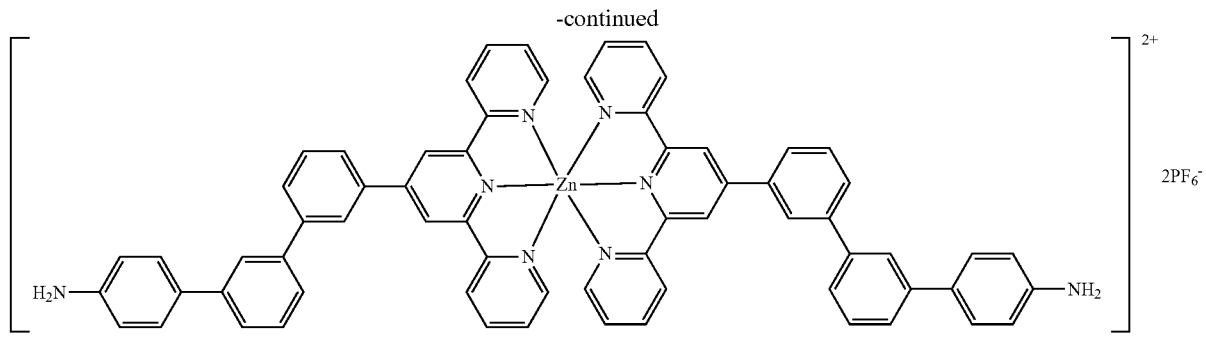

9

Methanol (10 mL) was added to a 50 mL reaction flask to dissolve compound P (182 mg, 0.316 mmol). After that, zinc chloride (26 mg, 0.158 mmol) in methanol (10 mL) was added dropwise, and the reactant was stirred and refluxed under the protection of argon for 4 h. Then the reactant was cooled to room temperature, and an excess of saturated ammonium hexafluorophosphate in methanol was added dropwise until the precipitation was completely precipitated, which was filtered. The obtained solid was rinsed with distilled water (2*10 mL) and ether (2*10 mL) in turn. The crude product was recrystallized with a mixed solvent of acetonitrile and acetone to obtain compound R.

$^1$H NMR (400 MHz, CDCl$_3$, 298 K): δ 8.75 (dd, J=7.5, 1.4 Hz, 4H), 8.59 (d, J=8.0 Hz, 8H), 7.94 (t, J=2.0 Hz, 4H), 7.66 (dd, J=8.1, 6.7 Hz, 4H), 7.61-7.39 (m, 20H), 7.00 (td, J=7.4, 1.6 Hz, 4H), 1.50 (s, 18H)$^{13}$C NMR (100 MHz, CDCl$_3$, 298 K): δ 195.12, 156.16, 153.93, 152.39, 151.10, 149.69, 142.64, 140.08, 139.77, 138.88, 138.77, 137.44, 136.75, 129.45, 129.37, 129.27, 128.17, 128.15, 127.82, 127.76, 126.46, 125.60, 125.08, 122.82, 80.43, 28.16. HRMS (TOF-ESI$^+$) (m/z): C$_{76}$H$_{64}$ZnN$_8$O$_4$ calculated: 1017.45 [M−2PF$_6^-$+H$^+$]; found: 1017.45.

The reaction was carried out located according to the method of Example 8, except that compound Q was relocated with compound R (0.158 g, 0.13 mmol), to obtain the interested compound 9.

$^1$H NMR (400 MHz, CDCl$_3$, 298 K): δ 8.43-8.52 (m, 12H), 8.05 (t, J=2.0 Hz, 2H), 7.97 (t, J=2.0 Hz, 2H), 7.79-7.58 (m, 12H), 7.48 (td, J=8.0, 1.3 Hz, 4H), 7.31-7.25 (m, 4H), 6.93 (ddd, J=8.0, 5.1, 1.1 Hz, 4H), 6.79-6.73 (m, 4H). $^{13}$C NMR (100 MHz, CDCl$_3$, 298 K) δ 156.38, 155.79, 149.14, 148.03, 147.56, 142.54, 140.08, 139.77, 138.84, 136.59, 134.36, 129.45, 129.37, 129.27, 128.17, 128.15, 128.05, 127.76, 125.60, 124.02, 121.39, 120.06, 115.37. HRMS (TOF-ESI$^+$) (m/z): C$_{60}$H$_{48}$ZnN$_8$ calculated: 1017.33 [M−2PF$_6^-$+H$^+$]; found: 1017.34.

(2) Preparation of Compound 9 Based Single Molecule Field Effect Transistor

A strongly-polarized molecule-graphene molecular heterojunction was constructed to obtain a compound 9 based field effect transistor with bottom gate structure according to the preparation method of transistor in Example 1, in which graphene was used as the gate electrode, hafnium oxide with a thickness of 5 nm was used as the dielectric layer, and compound 9 was used to replace compound 1.

Example 10: Preparation of Compound 10 Based Single Molecule Field Effect Transistor (1) Synthesis of Compound 10

The synthetic route is as follows:

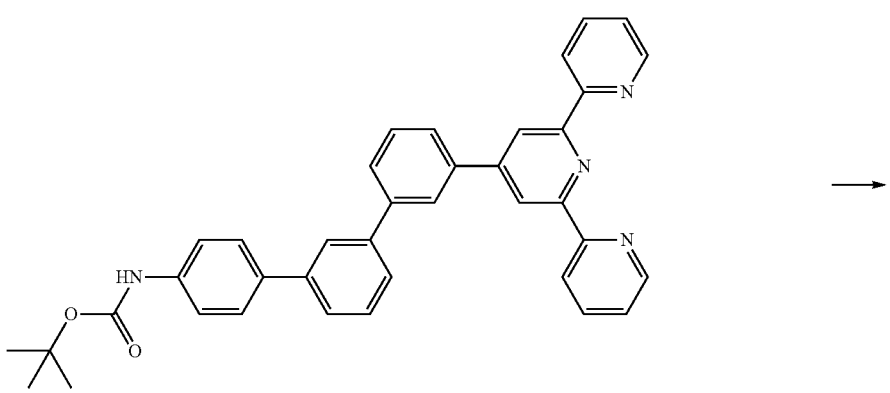

P

-continued

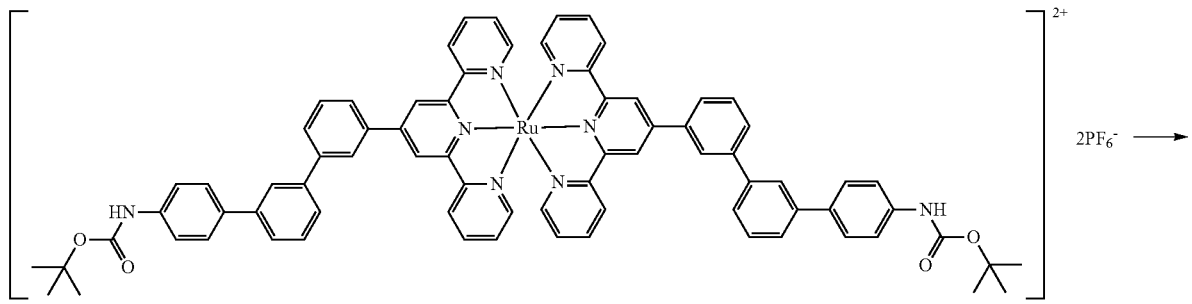

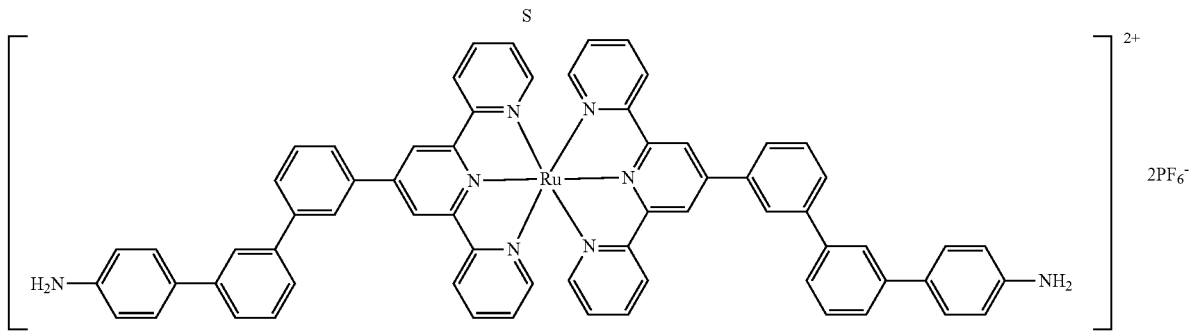

10

30

Methanol (10 mL) was added to a 50 mL reaction flask to dissolve compound P (182 mg, 0.316 mmol). After that, ruthenium chloride (33 mg, 0.158 mmol) in methanol (10 mL) was added dropwise, and the reactant was stirred and refluxed under the protection of argon for 4 h. Then the reactant was cooled to room temperature, and an excess of saturated ammonium hexafluorophosphate in methanol was added dropwise until the precipitation was completely precipitated, which was filtered. The obtained solid was rinsed with distilled water (2×10 mL) and ether (2×10 mL) in turn. The crude product was recrystallized with a mixed solvent of acetonitrile and acetone to obtain compound S as a red solid.

$^1$H NMR (400 MHz, CDCl$_3$, 298 K): δ 9.05 (dd, J=7.5, 1.4 Hz, 4H), 8.79 (d, J=8.0 Hz, 8H), 8.14 (t, J=2.0 Hz, 4H), 7.76 (dd, J=8.1, 6.7 Hz, 4H), 7.71-7.49 (m, 20H), 7.10 (td, J=7.4, 1.6 Hz, 4H), 1.50 (s, 18H). $^{13}$C NMR (100 MHz, CDCl$_3$, 298 K): δ 195.12, 155.16, 153.93, 152.39, 150.10, 149.69, 142.54, 141.08, 139.77, 138.94, 138.67, 137.44, 136.75, 129.45, 129.37, 129.27, 128.17, 128.15, 127.82, 127.76, 126.46, 125.60, 125.08, 122.82, 80.43, 28.16. HRMS (TOF-ESI$^+$) (m/z): C$_{76}$H$_{64}$RuN$_8$O$_4$ calculated: 1255.40 [M−2PF$_6^-$+H$^+$]; found: 1255.40.

The located reaction was carried out according to the method of Example 8, except that compound Q was relocated with compound S (0.164 g, 0.13 mmol), to obtain the interested compound 10 as a red solid.

$^1$H NMR (400 MHz, CDCl$_3$, 298 K): δ 8.63-8.72 (m, 12H), 8.25 (t, J=2.0 Hz, 2H), 8.17 (t, J=2.0 Hz, 2H), 7.89-7.68 (m, 12H), 7.68 (td, J=8.0, 1.3 Hz, 4H), 7.31-7.25 (m, 4H), 6.93 (ddd, J=8.0, 5.1, 1.1 Hz, 4H), 6.79-6.73 (m, 4H). $^{13}$C NMR (100 MHz, CDCl$_3$, 298 K) δ 156.38, 155.79, 149.14, 148.03, 147.56, 142.54, 140.08, 139.77, 138.84, 136.59, 134.36, 129.45, 129.37, 129.27, 128.17, 128.15, 128.05, 127.76, 125.60, 124.02, 121.39, 120.06, 115.37. HRMS (TOF-ESI$^+$) (m/z): C$_{66}$H$_{48}$RuN$_8$ calculated: 1055.31 [M−2PF$_6^-$+H$^+$]; found: 1055.31.

(2) Preparation of Compound 10 Based Single Molecule Field Effect Transistor

A strongly-polarized molecule-graphene molecular heterojunction was constructed to obtain a compound 10 based field effect transistor with bottom gate structure according to the preparation method of transistor in Example 1, in which graphene was used as the gate electrode, hafnium oxide with a thickness of 5 nm was used as the dielectric layer, and compound 10 was used to replace compound 1.

Example 11: Preparation of Compound 11 Based Single Molecule Field Effect Transistor (1) Synthesis of Compound 11

The synthetic route is as follows:

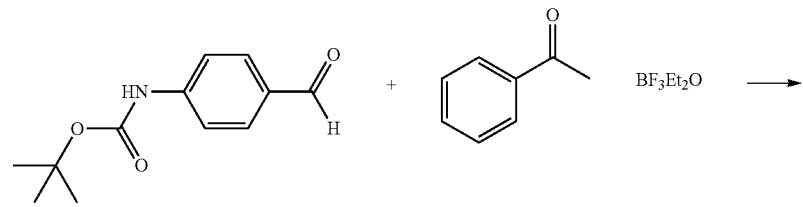

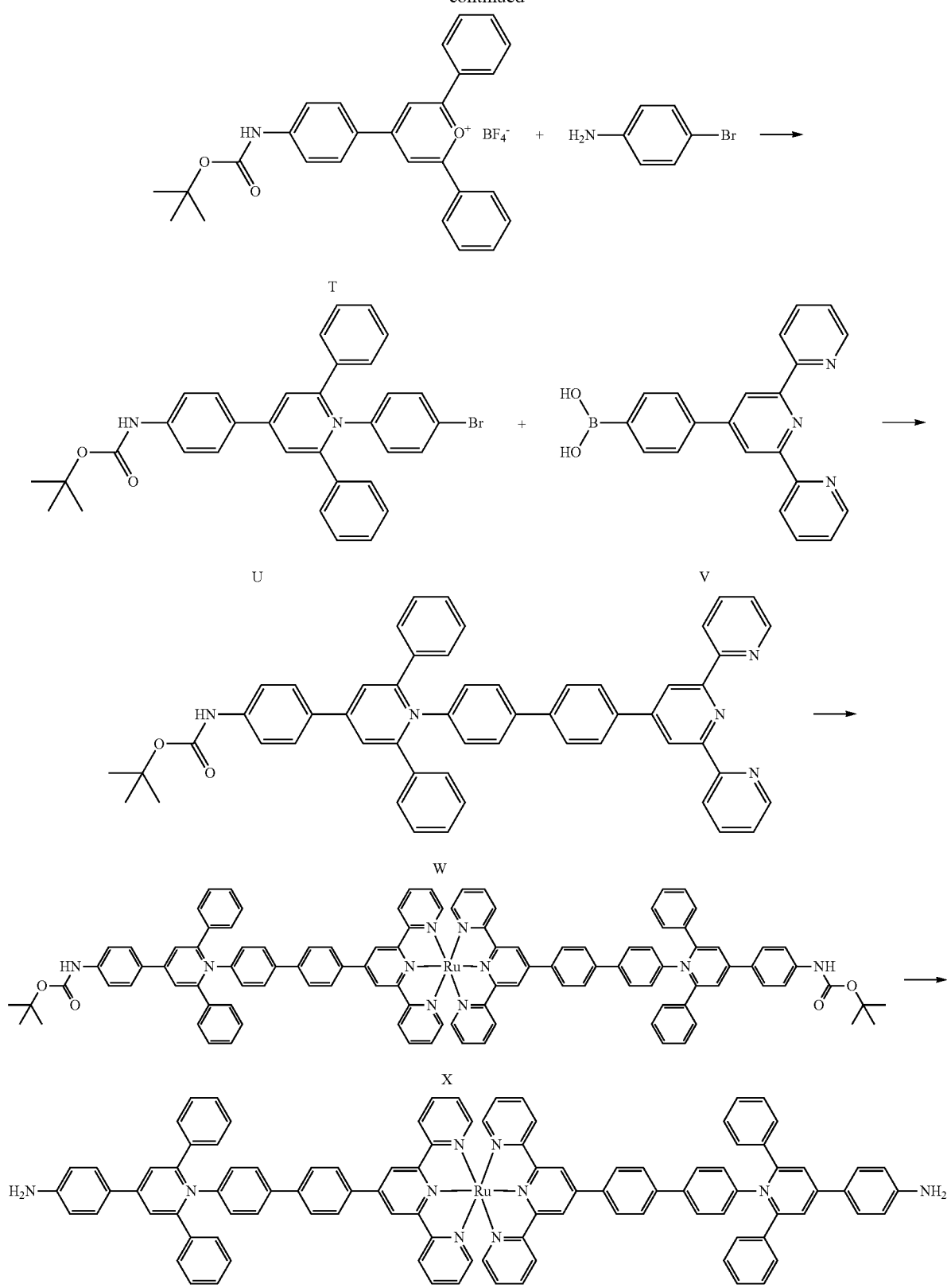

4-(Boc-amino) benzaldehyde (2.212 g, 10 mmol) and acetophenone (2.403 g, 20 mmol) were added to a reaction flask under the protection of argon. Boron trifluoride ether (4.258 g, 30 mmol) was added dr op wise with stirring, which was reacted at 100° C. for 3 h. After that, the reaction solution was cooled to room temperature, poured into ether (200 mL), and filtered to obtain the precipitated solid, which was recrystallized with absolute ethanol to obtain compound T as a yellow solid.

$^1$H NMR (400 MHz, CDCl$_3$, 298 K): δ 8.91-8.85 (m, 6H), 7.80-7.72 (m, 4H), 7.47-7.41 (m, 2H), 7.23 (tt, J=7.4, 2.0 Hz, 2H), 6.56-6.50 (m, 2H), 1.50 (s, 9H). $^{13}$C NMR (100 MHz, CDCl$_3$, 298 K) δ 168.71, 166.14, 153.93, 137.71, 133.99, 132.58, 131.06, 130.95, 129.13, 127.95, 126.42, 115.21, 80.43, 28.16. HRMS (TOF-ESI+) (m/z): C28H26NO3 calculated: 425.19 [M−BF$_4^-$+H+]; found: 425.19.

Compound T (511 mg, 1 mmol) was added to a reaction flask under the protection of argon, and dissolved with tetrahydrofuran (5 mL). After that, p-bromoaniline (172 mg, 1 mmol) was added. The reactant was refluxed for 4 h, cooled to room temperature. Ethanol was added for recrystallization, to obtain compound U.

$^1$H NMR (400 MHz, CDCl$_3$, 298 K): δ 7.89-7.81 (m, 4H), 7.59-7.53 (m, 2H), 7.52-7.46 (m, 6H), 7.41 (qd, J=3.8, 1.5 Hz, 6l1), 7.19-7.13 (m, 2H), 1.50 (s, 9H). $^{13}$C NMR (100 MHz, CDCl$_3$, 298 K) δ 156.07, 153.93, 140.59, 137.71, 136.23, 134.01, 132.14, 130.72, 129.94, 129.48, 128.57, 128.09, 127.95, 126.43, 126.40, 120.79, 80.43, 28.16. HRMS (TOF-ESI$^+$)(m/z): C$_{34}$H$_{30}$BrN$_2$O$_2$ calculated: 578.16[M−BF$_4^-$+H$^+$]; found: 578.16.

Compound V was synthesized according to the method described in the literature (J. Am. Chem. Soc. 2012, 134, 7672-7675).

Compound U (710 mg, 1.23 mmol), compound V (477 mg, 1.35 mmol), tetrakis(triphenylphosphine) palladium (14.6 mg, 12.3 μmol), and anhydrous potassium carbonate (1.60 g, 11.6 mmol) were added to a 100 mL Schlenk bottle in sequence, and then 25 mL of tetrahydrofuran and 5 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). After the organic phases were combined and dried over anhydrous sodium sulfate, the solvent was removed under reduced pressure. The crude product was analyzed and purified by silica gel column chromatography to obtain compound W.

$^1$H NMR (400 MHz, CDCl$_3$, 298K) δ 8.81 (dd, J=8.0, 1.0 Hz, 2H), 8.58 (s, 2H), 8.52 (dd, J=5.0, 1.3 Hz, 2H), 7.90-7.81 (m, 10H), 7.59-7.52 (m, 4H), 7.52-7.45 (m, 6H), 7.41 (qd, J=3.8, 1.5 Hz, 6H), 6.93 (ddd, J=8.0, 5.1, 1.1 Hz, 2H), 1.50 (s, 9H). $^{13}$C NMR (100 MHz, CDCl$_3$, 298 K) δ 156.72, 156.07, 155.79, 153.93, 149.49, 149.14, 142.53, 141.53, 138.74, 137.71, 136.59, 136.23, 135.65, 134.01, 131.13, 130.72, 129.94, 129.48, 128.90, 128.09, 127.95, 127.79, 127.28, 126.43, 126.40, 124.02, 121.39, 118.36, 80.43, 28.16 HRMS (TOF-ESI$^+$)(m/z). C$_{55}$H$_{44}$N$_5$O$_2$ calculated: 807.34 [M−BF$_4^-$+H$^+$]; found: 807.34.

Methanol (10 mL) was added to a 50 mL reaction flask to dissolve compound W (282 mg, 0.316 mmol). After that, ruthenium chloride (33 mg, 0.158 mmol) in methanol (10 mL) was added dropwise, and the reactant was stirred and refluxed under the protection of argon for 4 h. Then the reactant was cooled to room temperature, and an excess of saturated ammonium hexafluorophosphate in methanol was added dropwise until the precipitation was completely precipitated, which was filtered. The obtained solid was rinsed with distilled water (2×10 mL) and ether (2×10 mL) in turn. The crude product was recrystallized with a mixed solvent of acetonitrile and acetone to obtain compound X as a red solid.

$^1$H NMR (400 MHz, CDCl$_3$, 298 K): δ 8.75 (dd, J=7.5, 1.4 Hz, 4H), 8.59 (d, J=8.0 Hz, 8H), 7.90-7.81 (m, 20H), 7.59-7.52 (m, 8H), 7.51-7.37 (m, 25H), 7.00 (td, J=7.4, 1.6 Hz, 4H), 1.50 (s, 18H). $^{13}$C NMR (100 MHz, CDCl$_3$, 298 K): δ 156.07, 154.69, 153.93, 151.96, 150.33, 149.96, 142.53, 141.53, 138.80, 138.75, 137.71, 136.23, 135.65, 134.01, 131.13, 130.72, 129.94, 129.67, 129.48, 128.90, 128.09, 127.95, 127.79, 127.28, 126.43, 126.40, 125.48, 124.07, 80.43, 28.16. HRMS (TOF-ESI$^+$) (m/z): C$_{110}$H$_{88}$N$_{10}$O$_4$Ru calculated: 1715.61 [M−2BF$_4^-$−2PF$_6^-$+H$^+$]; found: 1715.61.

The reaction was carried out located according to the method of Example 8, except that compound Q was relocated with compound X (0.283 g, 0.13 mmol), to obtain the interested compound 11 as a red solid.

$^1$H NMR (400 MHz, CDCl$_3$, 298 K): δ 8.75 (dd, J=7.5, 1.6 Hz, 4H), 8.60-8.56 (m, 8H), 7.90-7.81 (m, 20H), 7.58-7.52 (m, 4H), 7.48 (s, 4H), 7.46-7.37 (m, 16H), 7.21-7.15 (m, 4H), 7.00 (td, J=7.4, 1.6 Hz, 4H), 6.81-6.75 (m, 4H). $^{13}$C NMR (100 MHz, CDCl$_3$, 298 K) δ 156.07, 154.69, 151.96, 150.33, 149.96, 148.03, 142.53, 141.53, 138.80, 138.74, 136.23, 135.65, 134.01, 131.13, 130.72, 129.94, 129.67, 129.48, 128.90, 128.22, 128.09, 127.79, 127.28, 125.48, 125.32, 124.07, 115.05. HRMS (TOF-ESI$^+$) (m/z): C$_{100}$H$_{72}$N$_{10}$Ru calculated. 1515.50 [M−2BF$_4^-$−2PF$_6^-$+H$^+$]; found: 1515.50.

(2) Preparation of Compound 11 Based Single Molecule Field Effect Transistor

A strongly-polarized molecule-graphene molecular heterojunction was constructed to obtain a compound 11 based field effect transistor with bottom gate structure according to the preparation method of transistor in Example 1, in which graphene was used as the gate electrode, hafnium oxide with a thickness of 5 nm was used as the dielectric layer, and compound 11 was used to replace compound 1.

Example 12: Preparation of Compound 12 Based Single Molecule Field Effect Transistor (1) Synthesis of Compound 12
The synthetic route is as follows:

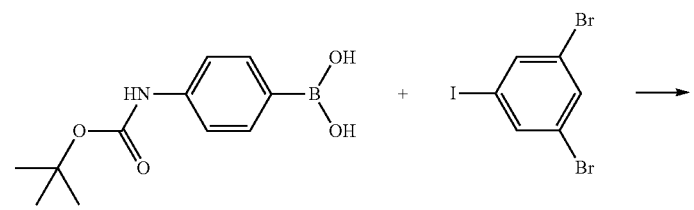

-continued
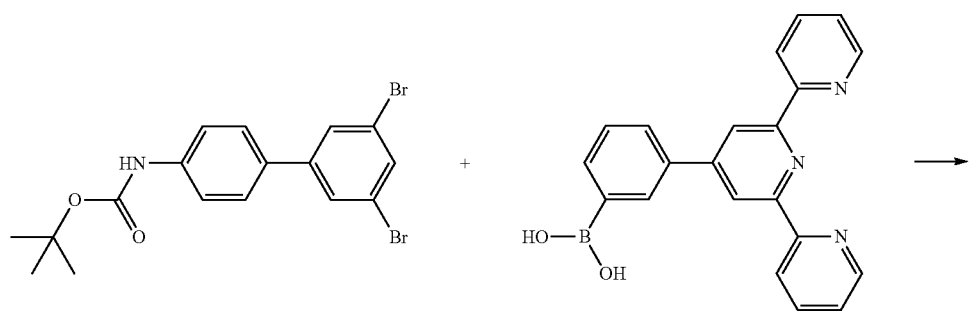
Y  +  O
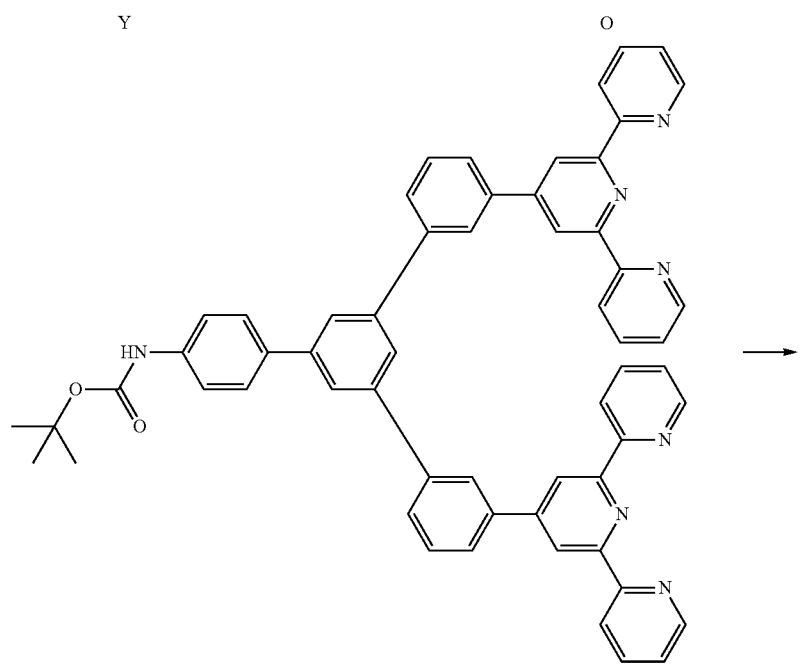
Z
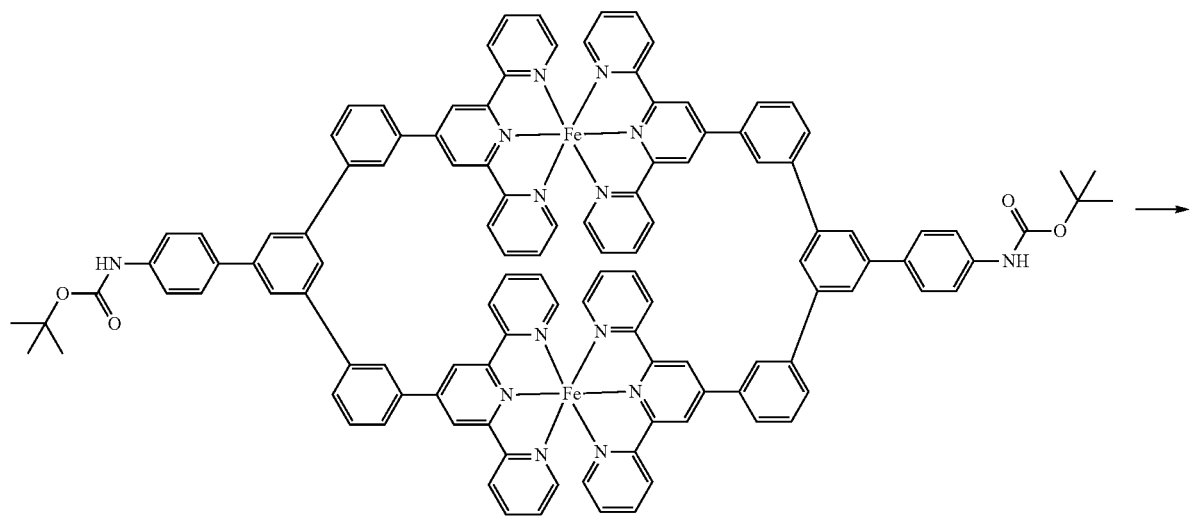
Z2

-continued

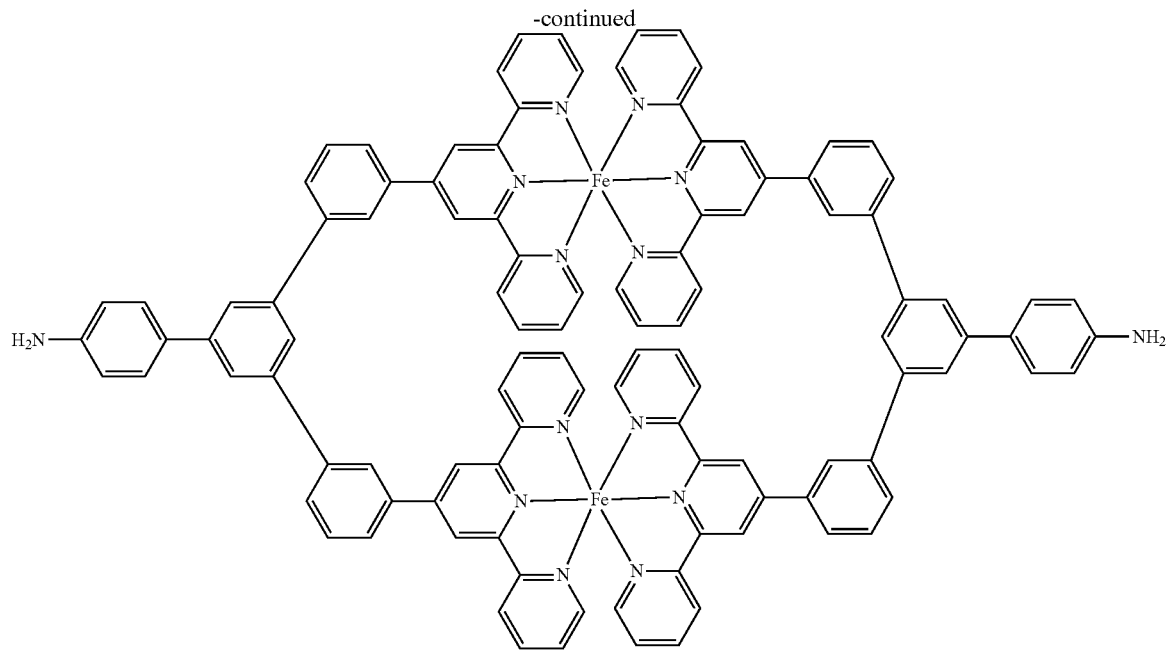

12

1,3-dibromo-5-iodobenzene (1.092 g, 3.02 mmol), 4-(Boc-amino)phenylboronic acid (455 mg, 3.32 mmol), palladium tetrakis(triphenylphosphine) (34.9 mg, 30.3 μmol), and anhydrous potassium carbonate (3.93 g, 28.5 mmol) were added to a 250 mL Schlenk bottle in sequence, and then 60 mL of tetrahydrofuran and 15 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (200 mL) and extracted with dichloromethane (3×60 mL). After the organic phases were combined and dried over anhydrous sodium sulfate, the solvent was removed under reduced pressure. The crude product was analyzed and purified by silica gel column chromatography to obtain compound Y.

$^1$H NMR (400 MHz, CDCl$_3$, 298 K): δ 7.76 (q, J=1.4 Hz, 3H), 7.72-7.65 (m, 2H), 7.56-7.50 (m, 2H), 6.57 (s, 1H), 1.50 (s, 9H). $^{13}$C NMR (100 MHz, CDCl$_3$, 298 K) δ 153.93, 143.19, 137.71, 134.00, 128.66, 127.95, 126.42, 123.44, 80.43, 28.16. HRMS (TOF-ESI$^+$) (m/z): C$_{17}$H$_{17}$Br$_2$NO$_2$ calculated: 425.97 [M+H$^+$]; found. 425.97.

Compound Y (522 mg, 1.23 mmol), compound O (477 mg, 1.35 mmol), tetrakis(triphenylphosphine) palladium (14.6 mg, 12.3 μmol), and anhydrous potassium carbonate (1.60 g, 11.6 mmol) were added to a 100 mL Schlenk bottle in sequence, and then 25 mL of tetrahydrofuran and 5 mL of distilled water were injected. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). After the organic phases were combined and dried over anhydrous sodium sulfate, the solvent was removed under reduced pressure. The crude product was analyzed and purified by silica gel column chromatography to obtain compound Z.

$^1$H NMR (400 MHz, CDCl$_3$, 298 K): δ 8.70-8.44 (m, 12H), 8.31 (dt, J=3.5, 2.0 Hz, 2H), 8.23 (t, J=2.0 Hz, 1H), 8.17 (t, J=2.0 Hz, 1H), 8.12 (t, J=1.9 Hz, 1H), 7.83-7.59 (m, 11H), 7.48 (td, J=8.0, 1.3 Hz, 4H), 6.93 (ddd, J=8.0, 5.1, 1.1 Hz, 4H), 1.50 (s, 9H). $^{13}$C NMR (100 MHz, CDCl$_3$, 298 K) δ 156.38, 155.79, 153.93, 149.14, 147.56, 141.72, 141.37, 138.86, 137.71, 136.59, 133.99, 129.37, 129.27, 129.18, 128.16, 127.95, 126.42, 124.02, 121.39, 120.06, 80.43, 28.16. HRMS (TOF-ESI$^+$) (m/z): C$_{59}$H$_{45}$N$_7$O$_2$ calculated: 884.35 [M+H$^+$]; found: 884.35.

Methanol (10 mL) was added to a 50 mL reaction flask to dissolve compound Z (280 mg, 0.316 mmol). After that, ferrous chloride (21 mg, 0.158 mmol) in methanol (10 mL) was added dropwise, and the reactant was stirred and refluxed under the protection of argon for 4 h. Then the reactant was cooled to room temperature, and an excess of saturated ammonium hexafluorophosphate in methanol was added dropwise until the precipitation was completely precipitated, which was filtered. The obtained solid was rinsed with distilled water (2×10 mL) and ether (2×10 mL) in turn. The crude product was recrystallized with a mixed solvent of acetonitrile and acetone to obtain compound Z2 as a purple solid.

$^1$H NMR (400 MHz, CDCl$_3$, 298 K): δ 8.75 (dd, J=7.5, 1.4 Hz, 8H), 8.59 (d, J=8.0 Hz, 15H), 8.04 (s, 6H), 7.94 (t, J=2.0 Hz, 4H), 7.66-7.42 (m, 28H), 1.50 (s, 18H). $^{13}$C NMR (100 MHz, CDCl$_3$, 298 K): δ 155.16, 153.93, 152.39, 150.10, 149.69, 141.72, 141.37, 138.86, 138.67, 137.71, 133.99, 129.45, 129.37, 129.27, 129.18, 128.16, 127.95, 126.42, 125.08, 122.82, 80.43, 28.16. HRMS (TOF-ESI$^+$) (m/z): C$_{118}$H$_{90}$Fe$_2$N$_{14}$O$_4$ calculated: 1879.58 [M−2PF$_6^-$+H$^+$]; found: 1879.58.

The reaction was carried out located according to the method of Example 8, except that compound Q was relocated with compound Z2 (0.282 g, 0.13 mmol), to obtain the interested compound 12 as a purple solid.

$^1$H NMR (400 MHz, CDCl$_3$, 298 K): δ 8.75 (dd, J=7.5, 1.6 Hz, 8H), 8.60-8.56 (m, 15H), 8.04 (s, 6H), 7.94 (t, J=2.0

Hz, 4H), 7.66 (dd, J=8.0, 6.7 Hz, 4H), 7.58 (dd, J=7.2, 2.0 Hz, 8H), 7.43 (td, J=7.4, 1.6 Hz, 8H), 7.21-7.15 (m, 4H), 7.00 (td, J=7.4, 1.6 Hz, 8H), 6.81-6.75 (m, 4H). $^{13}$C NMR (100 MHz, CDCl$_3$, 298 K) δ 155.16, 152.39, 150.10, 149.69, 148.03, 141.72, 141.37, 138.86, 138.67, 131.31, 129.45, 129.37, 129.27, 129.18, 128.27, 128.16, 125.08, 122.82, 115.05. HRMS (TOF-ESI$^+$) (m/z): C$_{108}$H$_{74}$Fe$_2$N$_{14}$ calculated: 1679.50 [M−2PF$_6^-$+H$^+$]; found: 1679.50.

(2) Preparation of Compound 12 Based Single Molecule Field Effect Transistor

A strongly-polarized molecule-graphene molecular heterojunction was constructed to obtain a compound 12 based field effect transistor with bottom gate structure according to the preparation method of transistor in Example 1, in which graphene was used as the gate electrode, hafnium oxide with a thickness of 5 nm was used as the dielectric layer, and compound 12 was used to replace compound 1.

Example 13: Preparation of Compound 13 Based Single Molecule Field Effect Transistor (1) Synthesis of Compound 13

The synthetic route is as follows:

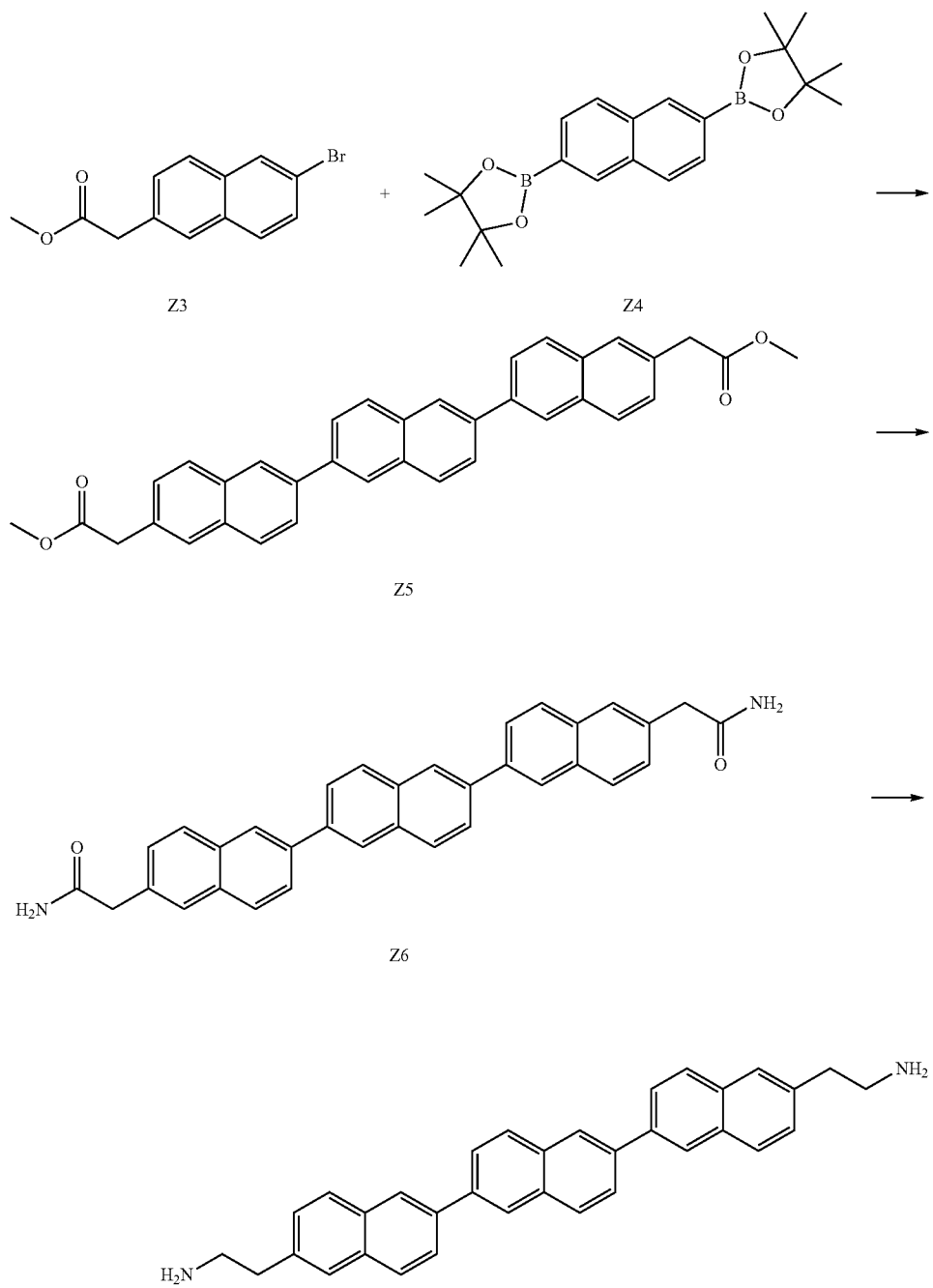

Compound Z3 was synthesized according to the route in the literature (*European Journal of Medicinal Chemistry*, 102, 277-287; 2015).

Compound Z4 was synthesized according to the route in the literature (*Journal of the American Chemical Society*, 136(10), 3972-3980; 2014).

Compound Z3 (0.279 g, 1 mmol), compound Z4 (0.878 g, 2.4 mmol), Pd(PPh$_3$)$_4$ (83 mg, 0.072 mmol) and K$_2$CO$_3$ (1.0 g, 7.2 mmol) were added to a 100 mL Schlenk bottle in sequence, and then THF/H$_2$O (20 mL/4 mL) was injected. The resultant was circulated 3 times by a freezing and thawing pump circulation method to remove oxygen, and then heated and stirred at 90° C. under the protection of argon for 24. After cooling, the reaction mixture was poured into water (50 mL) and extracted with dichloromethane (3×30 mL). The organic phases were combined and dried with Na$_2$SO$_4$ and the solvent was removed under reduced pressure. The crude product was analyzed and purified by silica gel column chromatography to obtain compound Z5 as a yellow solid.

$^1$H NMR (400 MHz, CDCl$_3$, 298 K): δ 8.11-7.96 (m, 6H), 7.92-7.80 (m, 6H), 7.80-7.61 (m, 6H), 3.92 (s, 4H), 3.75 (s, 6H). $^{13}$C NMR (100 MHz, CDCl$_3$, 298 K): δ 172.68, 137.95, 133.76, 132.68, 131.30, 129.89, 129.08, 128.51, 128.06, 127.35, 127.06, 125.89, 123.71, 123.64, 51.97, 40.77. HRMS (TOF-ESI+) (m/z): C$_{36}$H$_{28}$O$_4$ calculated: 525.21 [M+H$^+$]; found: 525.21.

Compound Z5 (0.488 g, 0.93 mmol) was added to 5 mL of 28% ammonia water, and the reaction was stirred at room temperature for 24 h. After that, the reactant was extracted with dichloromethane (3*10 mL). The organic phases were combined and dried over anhydrous sodium sulfate, and the solvent was removed under reduced pressure. The crude product was analyzed and purified by silica gel column chromatography to obtain compound Z6 as a yellow solid.

$^1$H NMR (400 MHz, CDCl$_3$, 298 K): δ 8.12-7.96 (m, 6H), 7.92-7.67 (m, 12H), 3.63 (s, 4H). $^{13}$C NMR (100 MHz, CDCl$_3$, 298 K): δ 172.58, 137.95, 135.09, 133.06, 131.30, 130.40, 128.51, 128.35, 128.06, 127.67, 125.89, 125.49, 123.71, 123.64, 41.07. HRMS (TOF-ESI+) (m/z): C$_{34}$H$_{26}$N$_2$O$_2$ calculated: 495.21 [M+H$^+$]; found: 495.21.

After LiAlH$_4$ (0.152 g, 4 mmol) and anhydrous THF (5 mL) were added to a reaction flask, a solution of compound Z6 (0.198 g, 0.4 mmol) in anhydrous THF (1 mL) was added dropwise. The reactant was then refluxed for 24 h, and cooled to room temperature. Water was added to quench the reaction. The resultant was extracted with dichloromethane (3×10 mL). The organic phases were combined and dried over anhydrous sodium sulfate, and the solvent was removed under reduced pressure. The crude product was analyzed and purified by silica gel column chromatography to obtain compound 13 as a yellow solid.

$^1$H NMR (400 MHz, CDCl$_3$, 298 K): δ 8.11-7.96 (m, 6H), 7.92-7.80 (m, 6H), 7.80-7.61 (m, 6H), 2.53 (s, 4H), 1.24 (s, 4H). $^{13}$C NMR (100 MHz, CDCl$_3$, 298 K): δ 137.95, 133.79, 131.30, 130.12, 128.64, 128.51, 128.06, 126.36, 125.89, 125.43, 123.71, 123.64, 43.70, 39.10. HRMS (TOF-ESI+) (m/z): C$_{34}$H$_{30}$N$_2$ calculated. 467.25 [M+H$^+$]; found: 467.25.

(2) Preparation of Compound 13 Based Single Molecule Field Effect Transistor

A strongly-polarized molecule-graphene molecular heterojunction was constructed to obtain a compound 13 based field effect transistor with bottom gate structure according to the preparation method of transistor in Example 1, in which graphene was used as the gate electrode, hafnium oxide with a thickness of 5 nm was used as the dielectric layer, and compound 13 was used to replace compound 1.

Example 14: Preparation of Compound 14 Based Single Molecule Field Effect Transistor (1) Synthesis of Compound 14

The synthetic route is as follows:

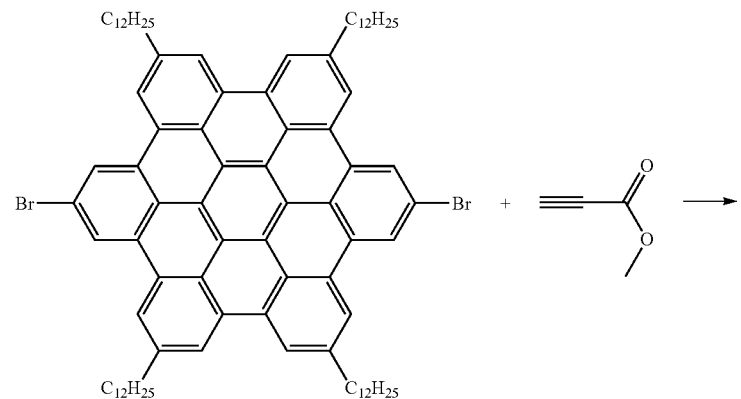

Z7

-continued
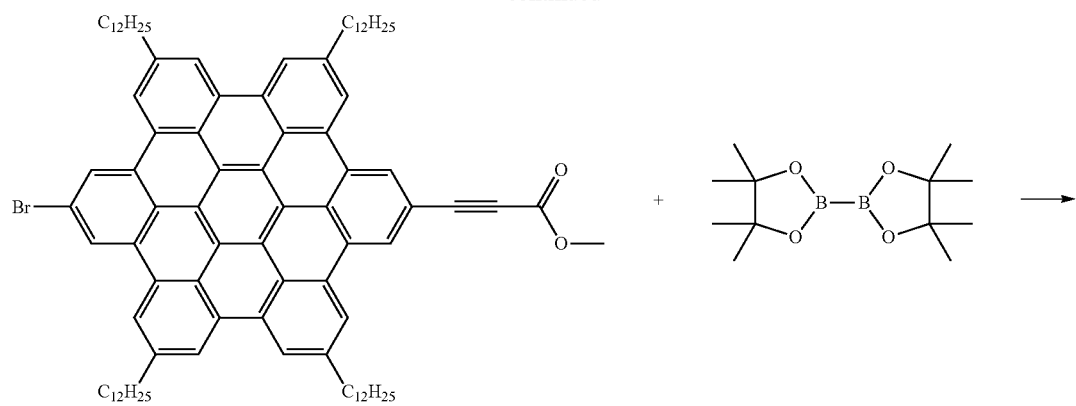
Z8
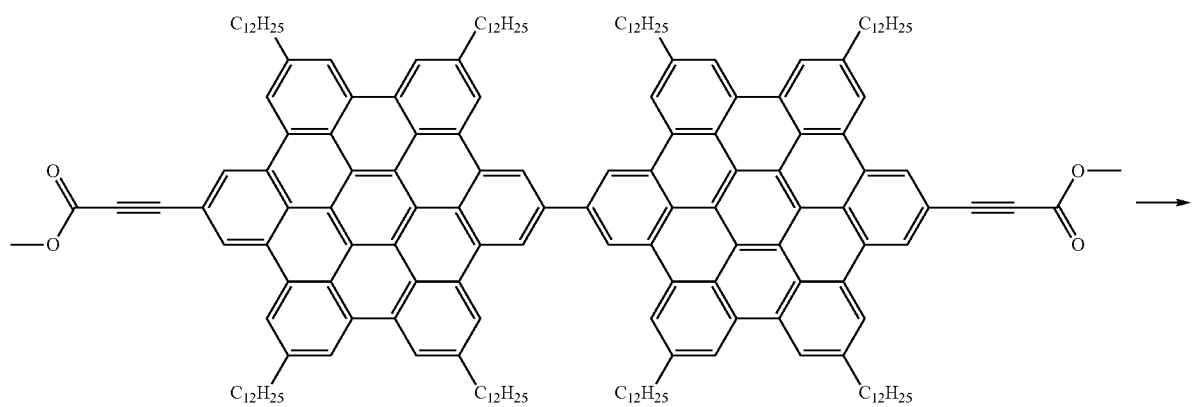
Z9
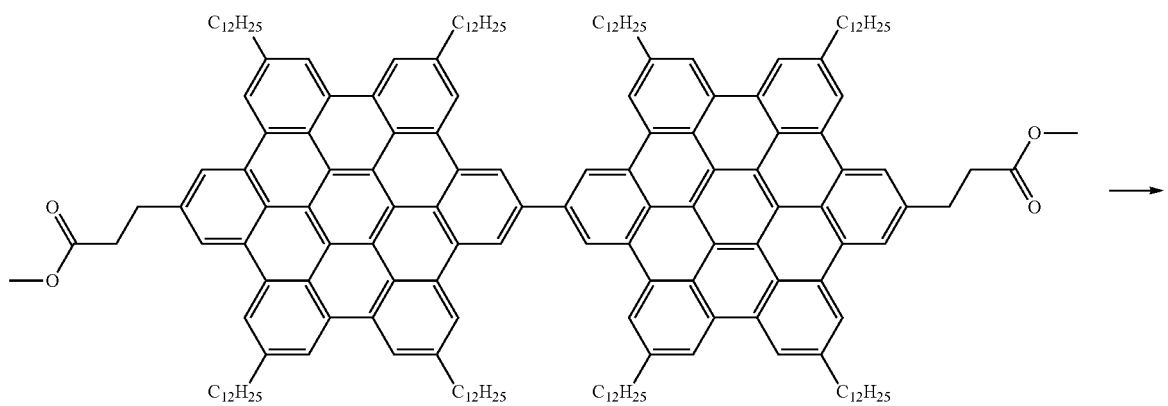
Z10

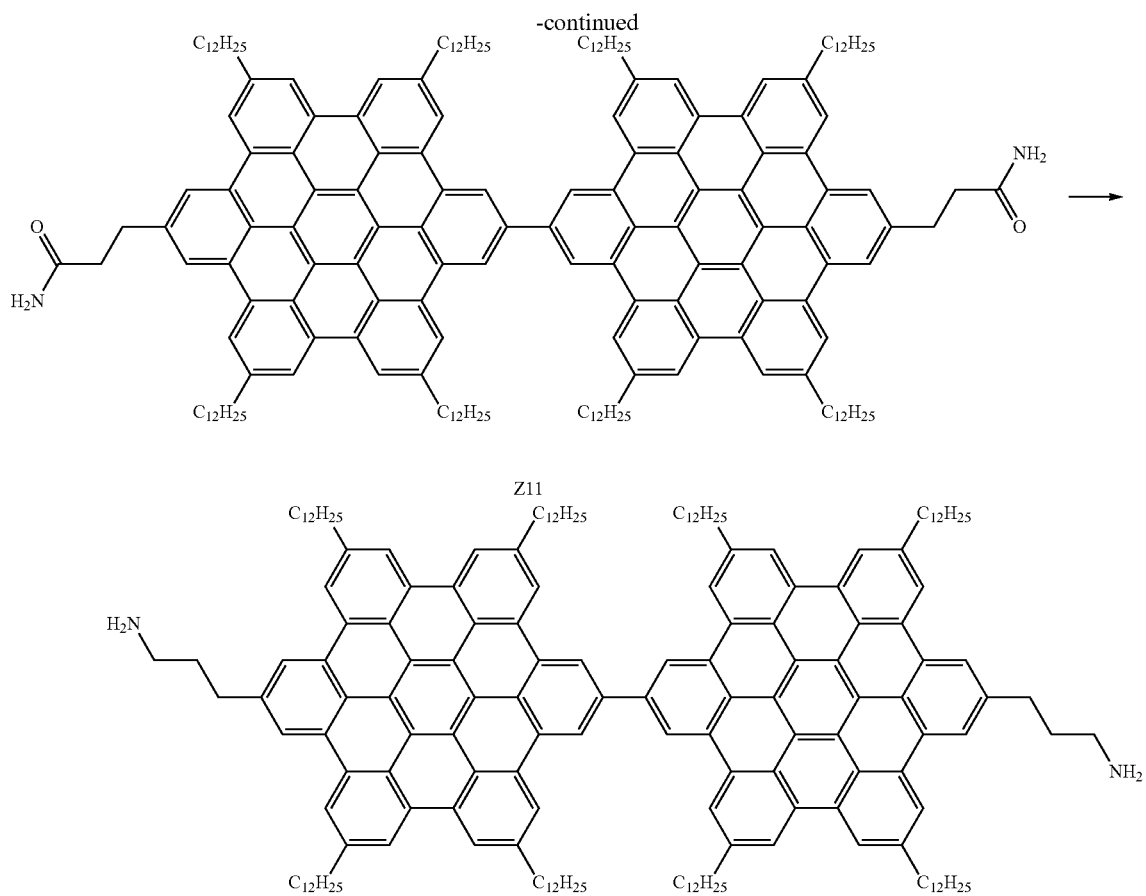

Z11

14

Compound Z7 was synthesized according to the route in the literature (*Chemistry—a European Journal*, 2001, 7(22): 4894-4901).

Compound Z7 (1.00 g, 0.69 mmol), copper iodide (0.572 g, 0.30 mmol), tetrakis(triphenylphosphine) palladium (0.182 g, 0.16 mmol), methyl propiolate (0.060 g, 0.71 mmol) and piperidine (60 mL) were added to a 250 mL Schlenk bottle. The resultant was circulated 3 times by a freezing and thawing pump circulation method to remove oxygen, and then heated and stirred at 90° C. under the protection of argon for 24 h. After cooling, the reaction mixture was poured into water (50 mL) and extracted with dichloromethane (3×30 mL). The organic phases were combined and dried with $Na_2SO_4$ and the solvent was removed under reduced pressure. The crude product was analyzed and purified by silica gel column chromatography to obtain compound Z8 as a yellow solid.

$^1$H NMR (400 MHz, $CDCl_3$, 298 K): δ 8.40 (s, 2H), 8.13 (s, 2H), 8.02 (s, 2H), 7.99 (s, 2H), 7.98 (s, 2H), 7.86 (s, 2H), 3.75 (s, 3H), 1.26 (m, 88H), 0.92-0.86 (m, 12H)$^{13}$C NMR (100 MHz, $CDCl_3$, 298 K): δ 173.44, 139.29, 139.13, 139.10, 129.83, 129.02, 128.96, 128.81, 128.45, 123.60, 123.21, 122.48, 122.29, 120.92, 120.65, 120.53, 120.45, 119.08, 118.94, 118.68, 118.17, 89.82, 82.48, 51.06, 37.29, 37.20, 34.02, 32.45, 32.39, 32.05, 31.98, 30.31, 30.27, 30.10, 30.04, 29.96, 29.88, 29.54, 29.45, 29.41, 25.09, 22.88, 20.15, 14.19.

HRMS (TOF-ESI+) (m/z): $C_{94}H_{115}BrO_2$ calculated: 1355.81 [M+H$^+$]; found: 1355.81.

Compound Z8 (1.10 g, 0.81 mmol), pinacol diborate (0.124 g, 0.49 mmol), palladium tetrakis(triphenylphosphine) (0.038 g, 0.03 mmol), and potassium acetate (0.40 g, 4.07 mmol) were added to a 250 mL Schlenk bottle in sequence, and then 50 mL of N,N-dimethylformamide was added. The resultant was circulated 3 times by a freezing and thawing pump circulation method to remove oxygen, and then heated and stirred at 90° C. under the protection of argon for 10 h. After cooling, the reaction mixture was poured into water (50 mL) and extracted with dichloromethane (3×30 mL). The organic phase was washed with water (3×30 mL) and saturated sodium chloride solution (30 mL) in turn, and dried with anhydrous sodium sulfate. The solvent was removed under reduced pressure. The crude product was analyzed and purified by silica gel column chromatography to obtain compound Z9 as a yellow solid.

$^1$H NMR (400 MHz, $CDCl_3$, 298 K): δ 8.50 (s, 4H), 8.23 (s, 4H), 8.18 (s, 4H), 8.09 (s, 4H), 7.98 (s, 4H), 7.88 (s, 4H), 3.75 (s, 6H), 1.26 (m, 176H), 0.92-0.86 (m, 24H).

$^{13}$C NMR (100 MHz, $CDCl_3$, 298 K): δ 175.49, 149.45, 139.93, 138.10, 129.81, 129.02, 128.96, 128.81, 128.45, 124.60, 124.21, 124.48, 123.39, 121.92, 121.65, 121.53, 120.45, 119.28, 118.94, 118.68, 118.27, 89.87, 82.58, 51.06, 37.29, 37.20, 34.02, 32.45, 32.39, 32.05, 31.98, 30.31, 30.27, 30.10, 30.04, 29.96, 29.88, 29.54, 29.45, 29.41, 25.09, 22.88, 20.15, 14.19.

HRMS (TOF-ESI+) (m/z): $C_{188}H_{230}O_4$ calculated. 2552.78 [M+H$^+$]; found: 2552.78.

Compound Z9 (663 mg, 0.26 mmol) was dissolved in THF (200 mL), and then Pd/C (10%, 285 mg) was added. $H_2$ (1 bar) was introduced at room temperature, and the reaction was stirred for 16 h. After the catalyst was removed by filtration, the solvent was removed under reduced pressure. The crude product was analyzed and purified by silica gel column chromatography to obtain compound Z10 as a yellow solid.

$^1$HNMR (400 MHz, CDCl$_3$, 298 K): δ 8.50 (s, 4H), 8.23 (s, 4H), 8.18 (s, 4H), 8.09 (s, 4H), 7.98 (s, 4H), 7.88 (s, 4HL 3.75 (s, 6H), 1.26 (m, 180H), 2.28 (t, J=7.5 Hz, 4H), 0.92-0.86 (m, 24H).

$^{13}$C NMR (100 MHz, CDCl$_3$, 298 K): δ 173.53, 139.42, 129.36, 122.91, 120.78, 119.15, 52.15, 37.29, 33.99, 32.51, 32.37, 32.04, 30.21, 30.05, 30.01, 29.93, 29.85, 29.76, 29.53, 29.48, 29.31, 25.02, 22.86, 14.18.

HRMS (TOF-ESI+) (m/z): $C_{188}H_{238}O_4$ calculated: 2560.84 [M+H$^+$]; found: 2560.84.

Compound Z10 (0.589 g, 0.23 mmol) was added to 5 mL of 28% ammonia water, and the reaction was stirred at room temperature for 24 h, then extracted with dichloromethane (3×10 mL). The organic phases were combined and dried over anhydrous sodium sulfate, and the solvent was removed under reduced pressure. The crude product was analyzed and purified by silica gel column chromatography to obtain compound Z11 as a yellow solid.

$^1$H NMR (400 MHz, CDCl$_3$, 298 K): δ 8.50 (s, 4H), 8.23 (s, 4H), 8.18 (s, 4H), 8.07 (s, 4H), 7.96 (s, 4H), 7.86 (s, 4H), 1.26 (m, 180H), 2.28 (t, J=7.5 Hz, 4H), 0.92-0.86 (m, 24H)$^{13}$C NMR (100 MHz, CDCl$_3$, 298 K): δ 173.53, 139.42, 129.36, 122.91, 120.78, 119.15, 51.05, 37.29, 33.99, 32.51, 32.37, 32.04, 30.21, 30.05, 30.01, 29.93, 29.85, 29.76, 29.53, 29.48, 29.31, 25.02, 22.86, 14.18.

HRMS (TOF-ESI+) (m/z): $C_{186}H_{236}N_2O_2$ calculated: 2530.85 [M+H$^+$]; found: 2530.85.

After LiAlH$_4$ (0.152 g, 4 mmol) and anhydrous THF (50 mL) were added to a reaction flask, a solution of compound Z11 (0.506 g, 0.20 mmol) in anhydrous THF (50 mL) was added dropwise. The reactant was then refluxed for 24 h, and cooled to room temperature. Water was added to quench the reaction. The resultant was extracted with dichloromethane (3×30 mL). The organic phase were combined and dried over anhydrous sodium sulfate, and the solvent was removed under reduced pressure. The crude product was analyzed and purified by silica gel column chromatography to obtain compound 14 as a yellow solid.

$^1$H NMR (400 MHz, CDCl$_3$, 298 K): δ 8.50 (s, 4H), 8.23 (s, 4H), 8.18 (s, 4H), 8.07 (s, 4H), 7.96 (s, 4H), 7.86 (s, 4H), 1.26 (m, 192H), 0.92-0.86 (m, 24H) $^{13}$C NMR (100 MHz, CDCl$_3$, 298 K): δ 173.53, 139.42, 129.36, 122.91, 120.78, 119.15, 54.05, 48.67, 38.29, 33.89, 32.51, 32.35, 31.84, 30.61, 30.05, 30.01, 29.93, 29.85, 29.76, 29.53, 29.48, 29.31, 25.01, 22.84, 14.19. HRMS (TOF-ESI+) (m/z): $C_{186}H_{240}N_2$ calculated: 2502.89 [M+H$^+$]; found: 2502.89.

(2) Preparation of Compound 14 Based Single Molecule Field Effect Transistor

A strongly-polarized molecule-graphene molecular heterojunction was constructed to obtain a compound 14 based field effect transistor with bottom gate structure according to the preparation method of transistor in Example 1, in which graphene was used as the gate electrode, hafnium oxide with a thickness of 5 nm was used as the dielectric layer, and compound 14 was used to replace compound 1.

Example 15: Preparation of Compound 1 Based Single Molecule Field Effect Transistor Graphene was used as the gate electrode, and zirconium oxide with a thickness of 5 nm was used as the dielectric layer to construct a field effect transistor with a bottom gate structure.

First, a bottom gate was formed on the silicon wafer according to the method described in Example 1.

A zirconium oxide layer with a thickness of 5 nm was deposited on the bottom gate by the electron beam evaporation deposition method.

According to the method described in Example 1, a strongly-polarized molecule-graphene molecule heterojunction was constructed on the dielectric layer to obtain a single molecule field effect transistor device.

Example 16: Preparation of Compound 1 Based Single Molecule Field Effect Transistor Graphene was used as the gate electrode, and titanium oxide with a thickness of 5 nm was used as the dielectric layer to construct a field effect transistor with a bottom gate structure.

First, a bottom gate was formed on the silicon wafer according to the method described in Example 1.

A titanium oxide layer with a thickness of 5 nm was deposited on the bottom gate by the electron beam evaporation deposition method.

According to the method described in Example 1, a strongly-polarized molecule-graphene molecule heterojunction was constructed on the dielectric layer to obtain a single molecule field effect transistor device.

Example 17: Preparation of Compound 1 Based Single Molecule Field Effect Transistor Aluminum was used as the gate electrode, and aluminium oxide with a thickness of 5 nm was used as the dielectric layer to construct a field effect transistor with a bottom gate structure.

First, an aluminum layer with a thickness of 35 nm was deposited on the silicon wafer by electron beam evaporation deposition method. After that, it was heated at 180° C. for 1 hour to prepare an aluminum oxide layer with a thickness of 5 nm.

According to the method described in Example 1, a strongly-polarized molecule-graphene molecule heterojunction was constructed on the dielectric layer to obtain a single molecule field effect transistor device.

Example 18: Preparation of Compound 1 Based Single Molecule Field Effect Transistor Aluminum was used as the gate electrode, and aluminium oxide with a thickness of 3 nm and hafnium oxide with a thickness of 2 nm were used as the dielectric layer to construct a field effect transistor with a bottom gate structure.

First, an aluminum layer with a thickness of 35 nm was deposited on the silicon wafer by electron beam evaporation deposition method. After that, it was located in the atmosphere for 24 hours, and naturally oxidized to obtain an aluminum oxide layer with a thickness of 3 nm, and then a hafnium oxide layer with a thickness of 2 nm was deposited by atomic layer deposition.

According to the method described in Example 1, a strongly-polarized molecule-graphene molecule heterojunction was constructed on the hafnium oxide layer to obtain a single molecule field effect transistor device.

Example 19: Preparation of Compound 1 Based Single Molecule Field Effect Transistor Example 19 differs from Example 15 in that the thickness of zirconium oxide was 3 nm.

Example 20: Preparation of Compound 1 Based Single Molecule Field Effect Transistor Example 20 differs from Example 15 in that the thickness of zirconium oxide was 10 nm.

Example 21: Preparation of Compound 2 Based Single Molecule Field Effect Transistor Graphene was used as the gate electrode, and hafnium oxide with a thickness of 5 nm was used as the dielectric layer to construct a field effect transistor with a top gate structure.

With reference to the method described in Example 1, a strongly-polarized molecule-graphene molecule heterojunction was constructed on a silicon wafer having an oxide layer with a thickness of 300 nm.

On another silicon wafer, a hafnium oxide layer with a thickness of 5 nm was prepared by the sol-gel method. After that, the graphene grown by chemical vapor deposition was transferred thereon, on which PMMA was further spin-coated. Finally, the silicon wafer was etched with hydrofluoric acid. The hafnium oxide/graphene/PMMA film was rinsed with deionized water and isopropanol three times, respectively, which was then located on the molecule heterojunction to obtain a single molecule field effect transistor device with a top gate structure based on compound 2.

Example 22: Preparation of Compound 2 Based Single Molecule Field Effect Transistor Example 22 differs from Example 21 in that: a zirconium oxide layer with a thickness of 5 nm prepared by the electron beam evaporation method was used as the dielectric layer.

Example 23: Preparation of Compound 2 Based Single Molecule Field Effect Transistor Example 23 differs from Example 21 in that: a titanium oxide layer with a thickness of 5 nm prepared by the atomic layer deposition method was used as the dielectric layer.
Performance Test Example of Single Molecule Field Effect Transistor Example 24

Agilent 4155C semiconductor tester and Karl Suss (PM5) manual probe station were used to test the performance of single molecule field effect transistors prepared in Examples 1-7.

At room temperature and atmospheric conditions, the gate voltage is changed within the range of −2 V to +2 V. The source-drain bias voltage (−1 V∼+1 V) was applied with fixing a certain gate voltage. I-V characteristic curve of the above-mentioned single molecule field effect transistor modulated by the gate voltage was determined (as shown in FIGS. 3-9). It can be seen from FIGS. 3-9 that the single molecule field effect transistor prepared in Examples 1-7 exhibits the conductivity characteristic that it varies with the gate voltage. Specifically, the I-V curves under different gate voltages are significantly different. As the gate voltage changes from negative to positive, the conductivity characteristics significantly change by gradually decreasing. This indicates that the single molecular field effect transistors prepared in Examples 1-7 have efficient gate modulation characteristics. At the same time, it is fully proved that the single molecule field effect transistors provided by the present application have indeed realized the characteristics of industrial transistors and have a wide range of application prospects.

In addition, it should be noted that although the gate voltage range of the aforementioned test is −2 V∼+2 V, it is confirmed by experiments that I-V characteristic curves similar to those shown in FIGS. 3-9 can be obtained within the gate voltage range of −4 V∼+4 V, by which the conductivity characteristic that it varies with the gate voltage is also shown.

It should be noted that the single molecule field effect transistors prepared in Examples 8-23 can also fit I-V characteristic curves similar to those of the single molecule field effect transistor prepared in Example 1-7. Therefore, they can achieve the same technical effect of the single molecule field effect transistors prepared in Example 1-7.

Through the performance test experiment analysis, it can be seen that the strongly-polarized molecules containing the groups with the polarizability greater than 2 C·m$^2$/V are prone to polarization due to the abundant electron cloud of the molecules and the application of voltage, which in turn makes molecular orbital energy levels shift more. Therefore, it is easier to effectively realize the gate modulation of the single molecule field effect transistor.

It should be noted that the documents cited herein are incorporated herein by reference in their entirety, which will not be repeated herein.

The above examples are intended to illustrate the substantial content of the present application, but do not limit the scope of protection of the present application. A person skilled in the art should understand that the technical solutions of the present application may be modified or equivalently altered, without departing from the spirit and scope of the technical solutions of the present application.

The invention claimed is:

1. An strongly-polarized molecule represented by general formula (I):

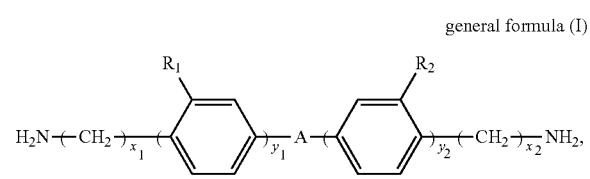

general formula (I)

wherein, A is a group having a polarizability greater than 2 C·m$^2$/V, and where A is:

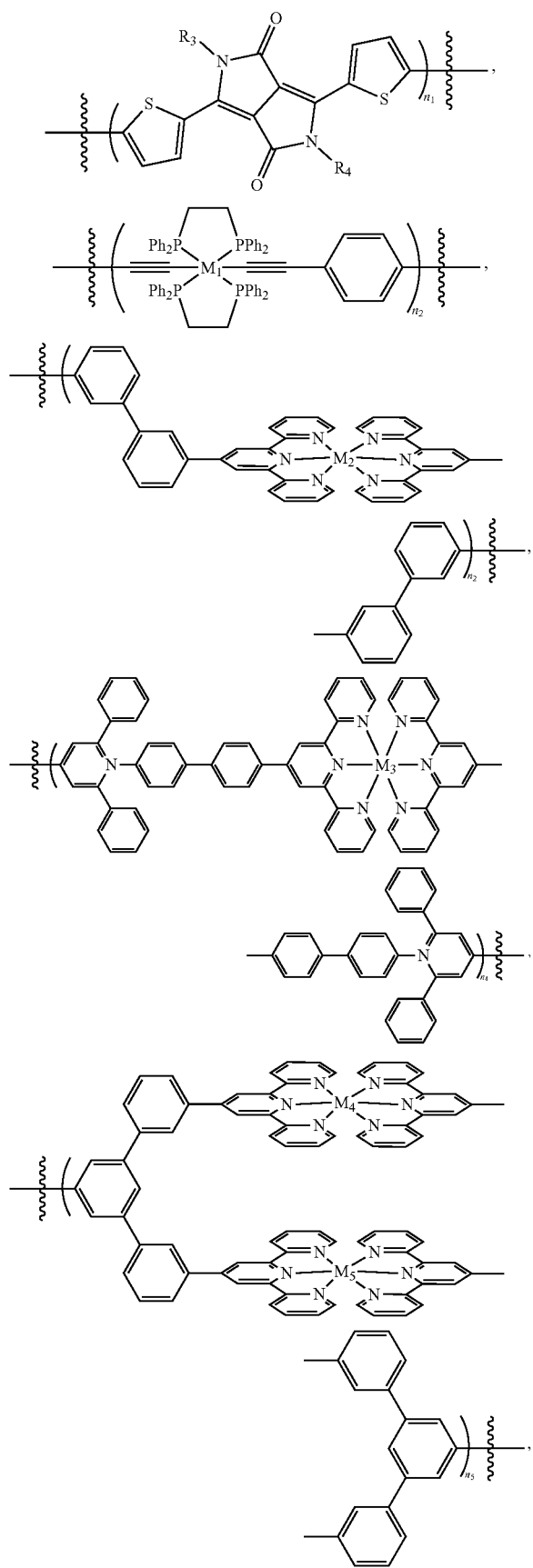
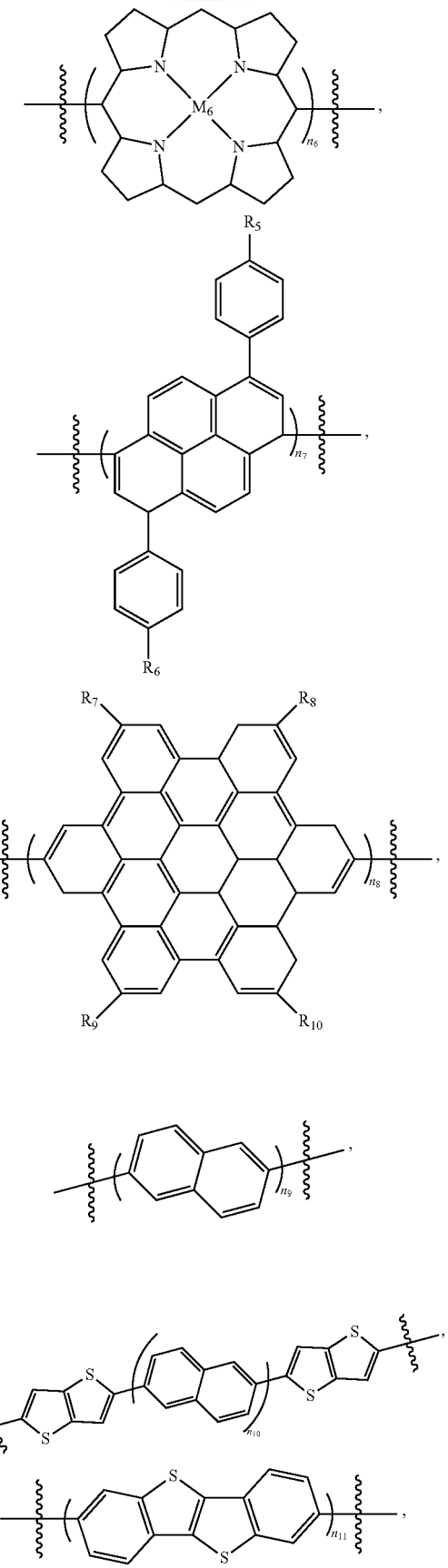

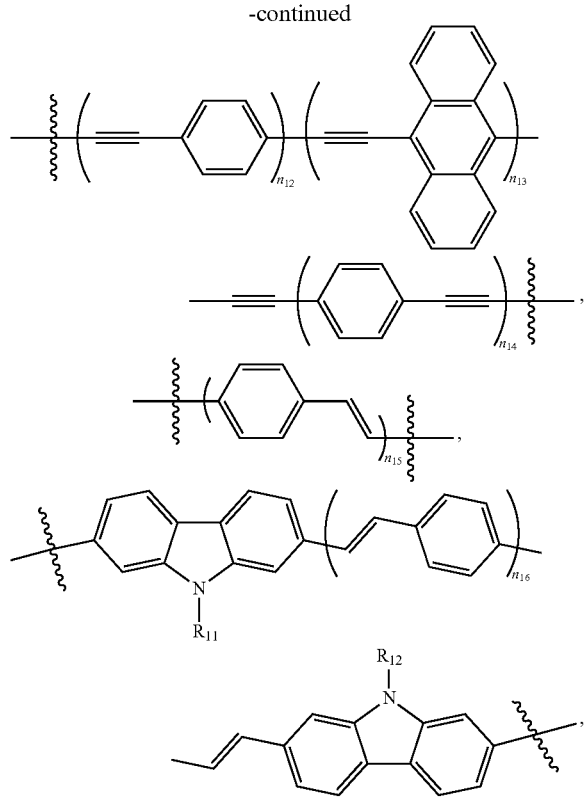

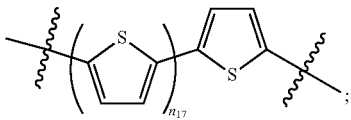

$R_1$, $R_2$, $R_3$, $R_4$, $R_5$, $R_6$, $R_7$, $R_8$, $R_9$, $R_{10}$, $R_{11}$ and $R_{12}$ are respectively any one of hydrogen, halogen, hydroxyl, amino, cyano, nitro, carboxyl, $C_{1-12}$ alkyl, $C_{1-12}$ alkoxy, halogenated $C_{1-12}$ alkyl, halogenated $C_{1-12}$ alkoxy, hydroxyl $C_{1-12}$ alkyl, hydroxyl $C_{1-12}$ alkoxy, and $C_{1-12}$ alkyl amino;

$x_1$ and $x_2$ are 0 or a positive integer respectively;

$y_1$ and $y_2$ are 0 or a positive integer respectively;

$M_1$, $M_2$, $M_3$, $M_4$, $M_5$ and $M_6$ are respectively a central atom or central ion of the complex;

$n_1$, $n_2$, $n_3$, $n_4$, $n_5$, $n_6$, $n_7$, $n_8$, $n_9$, $n_{10}$, $n_{11}$, $n_{12}$, $n_{13}$, $n_{14}$, $n_{15}$, $n_{16}$ and $n_{17}$ are respectively a positive integer.

2. The strongly-polarized molecule according to claim 1, having any one of the following general formulae:

general formula (II)

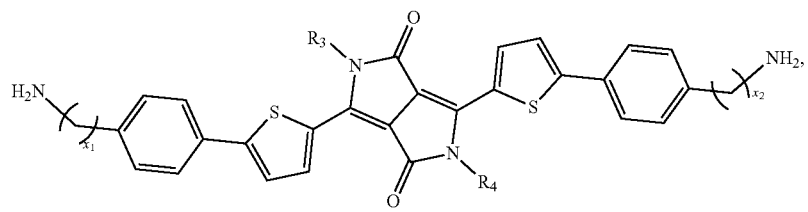

general formula (III)

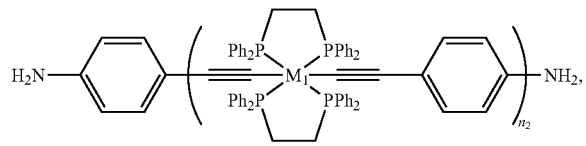

general formula (IV)

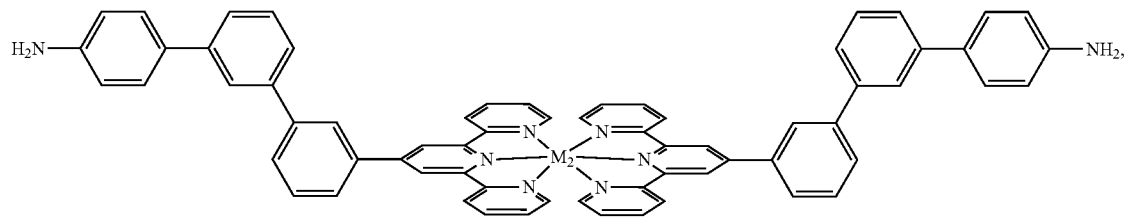

general formula (V)
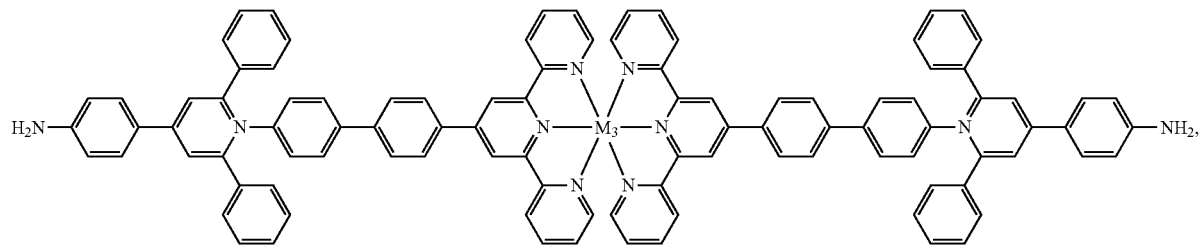
general formula (VI)
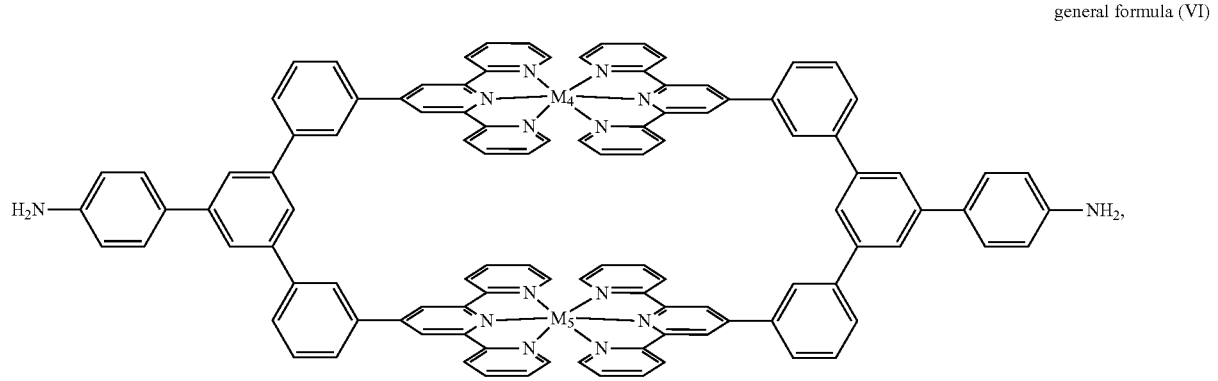
general formula (VII)
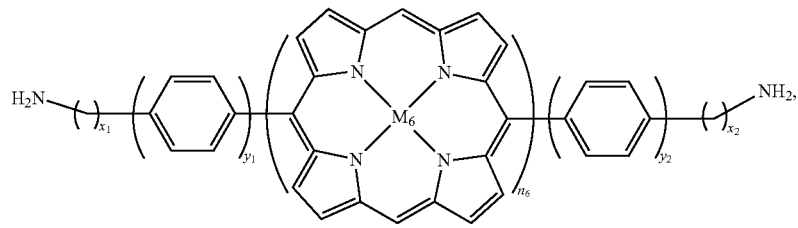
general formula (VIII)
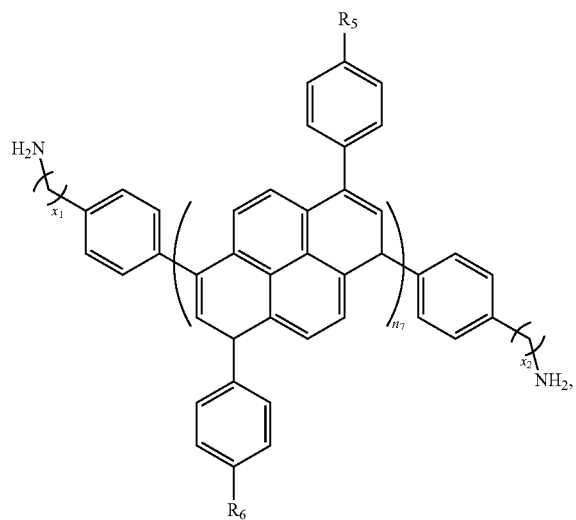

-continued
general formula (IX)
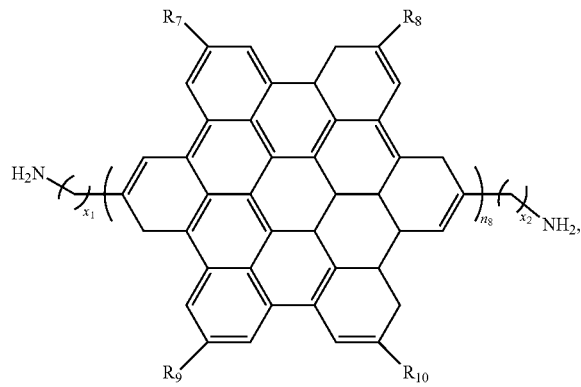
generla formula (X)
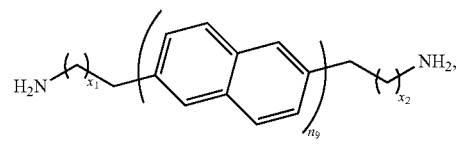
generla formula (XI)
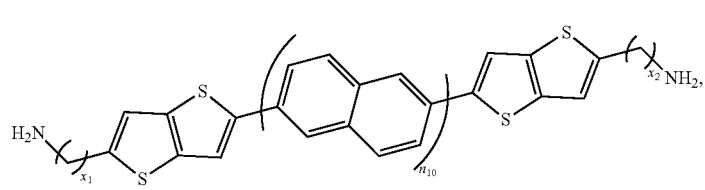
generla formula (XII)
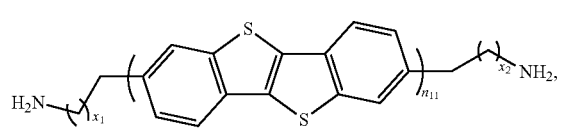
generla formula (XIII)
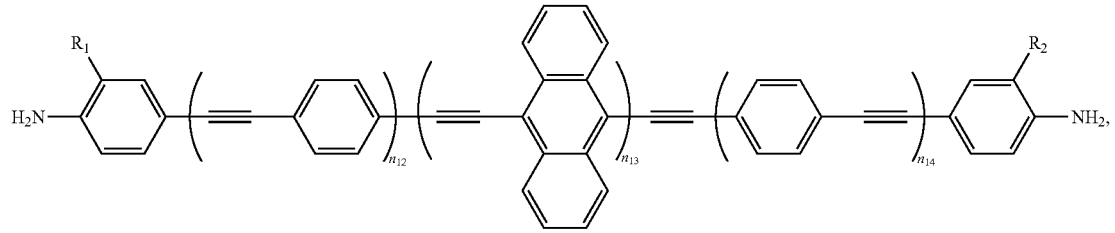
generla formula (XIV)
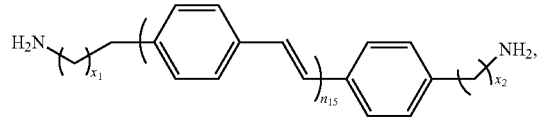
generla formula (XV)
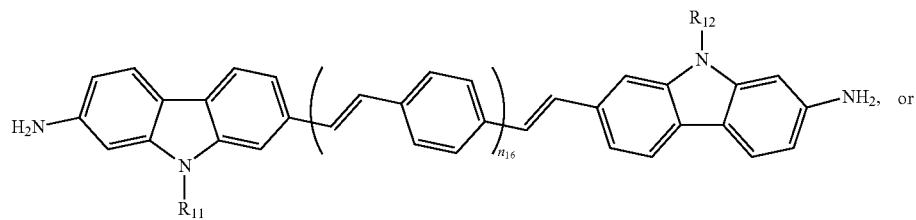
or
generla formula (XVI)
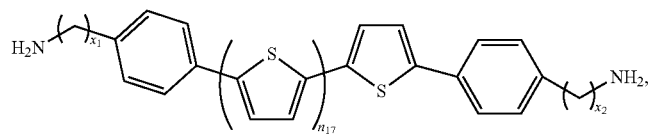

wherein, $R_1, R_2, R_3, R_4, R_5, R_6, R_7, R_8, R_9, R_{10}, R_{11}, R_{12}, M_1, M_2, M_3, M_4, M_5, M_6, n_2, n_6, n_7, n_8, n_9, n_{10}, n_{11}, n_{12}, n_{13}, n_{14}, n_{15}, n_{16}, n_{17}, x_1, x_2, y_1$, and $y_2$ are as defined in claim 1.
3. The strongly-polarized molecule according to claim 1, having any one of the following structural formulae:
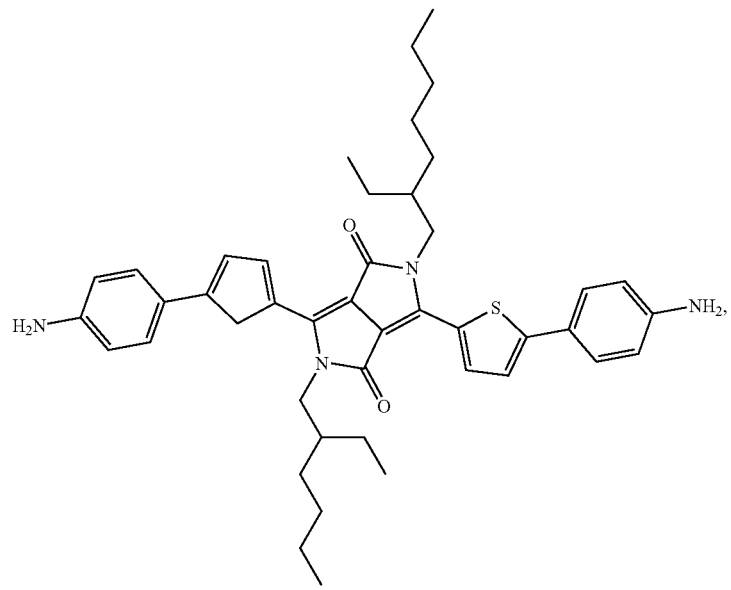
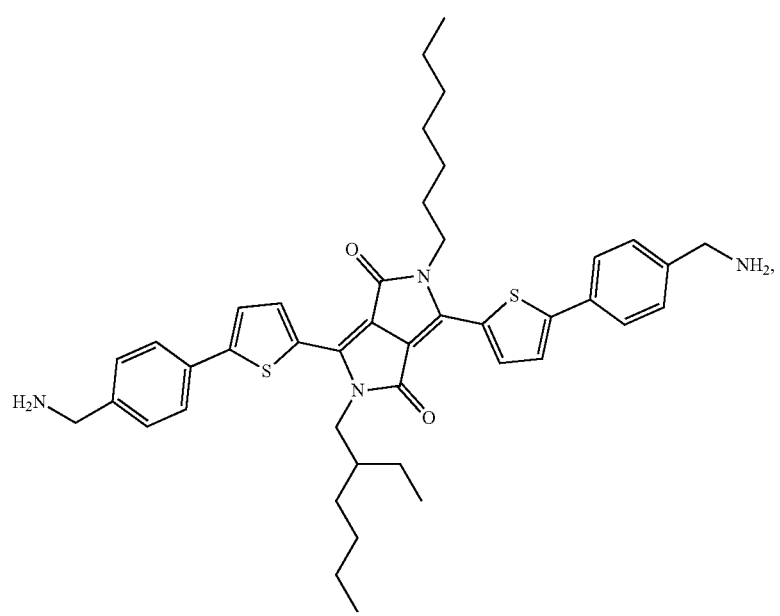

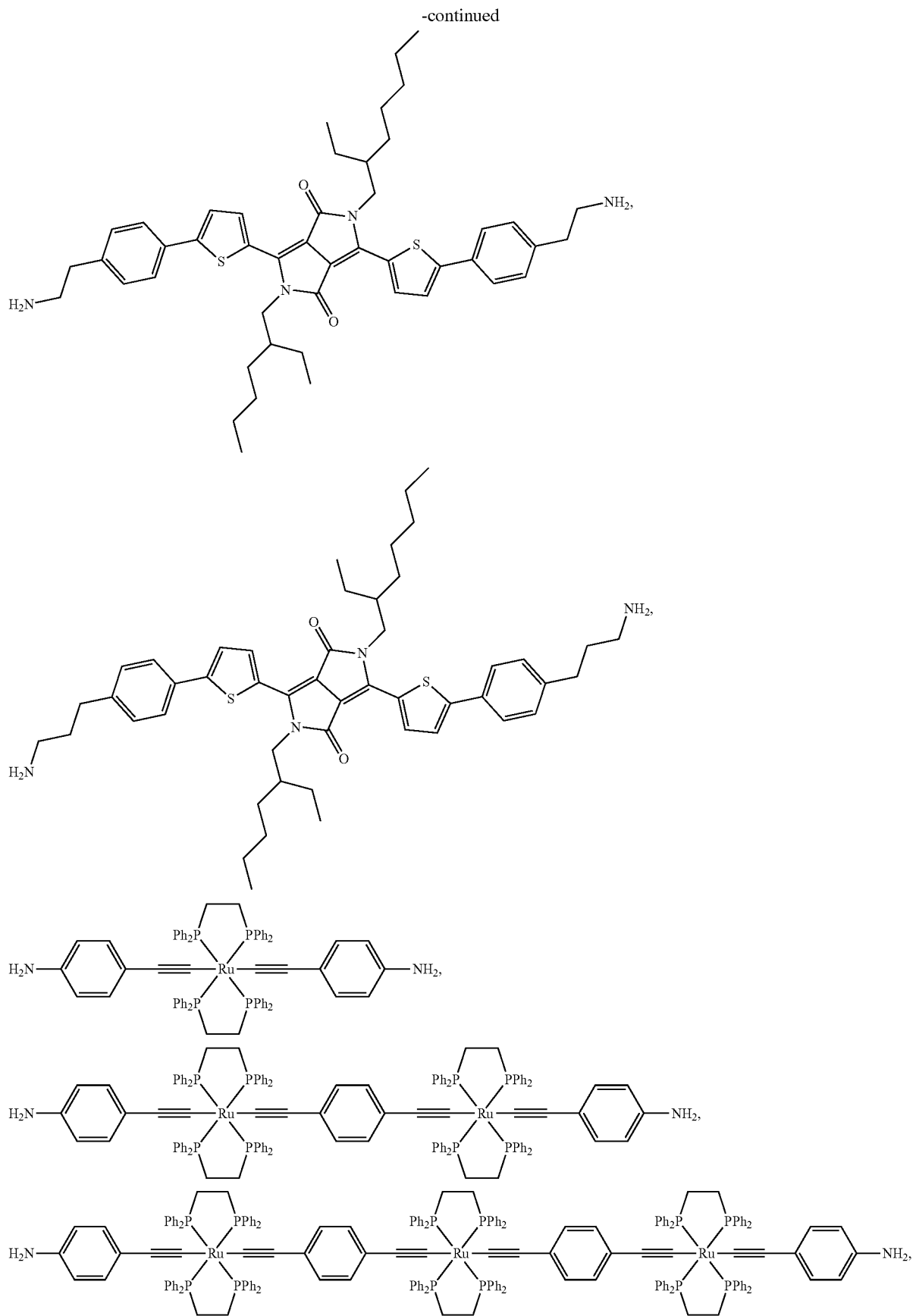

-continued
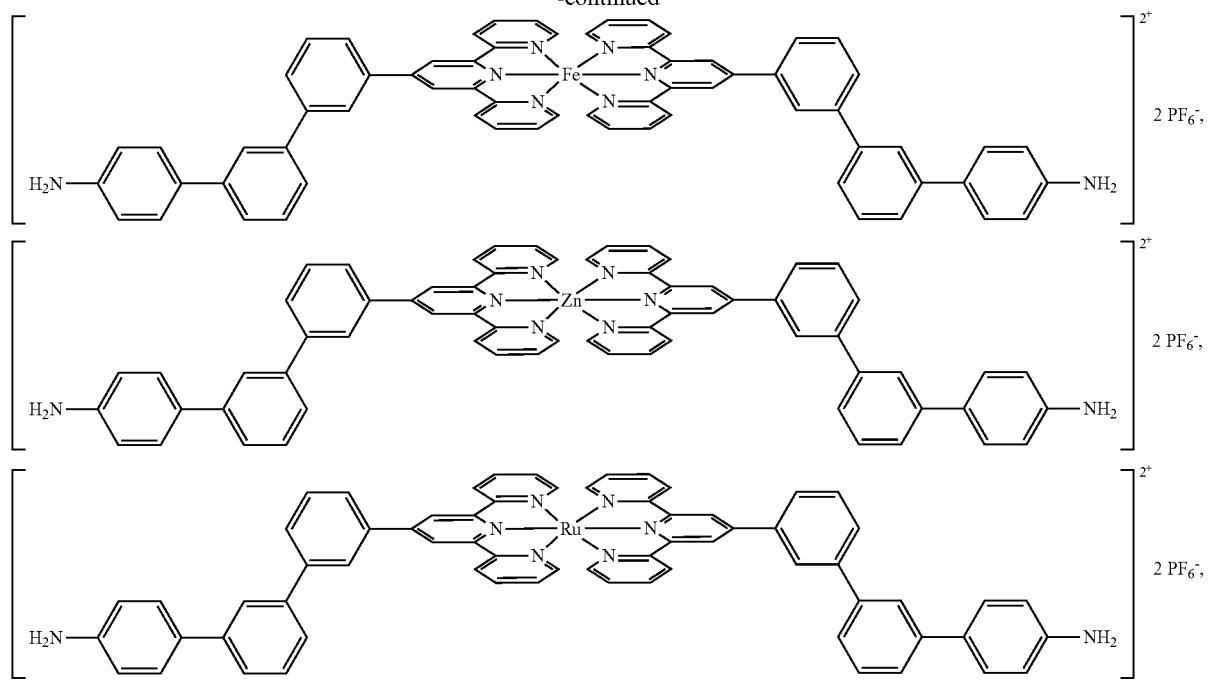
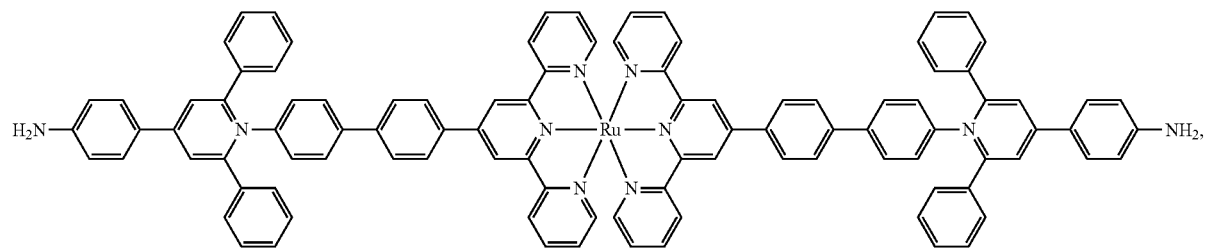
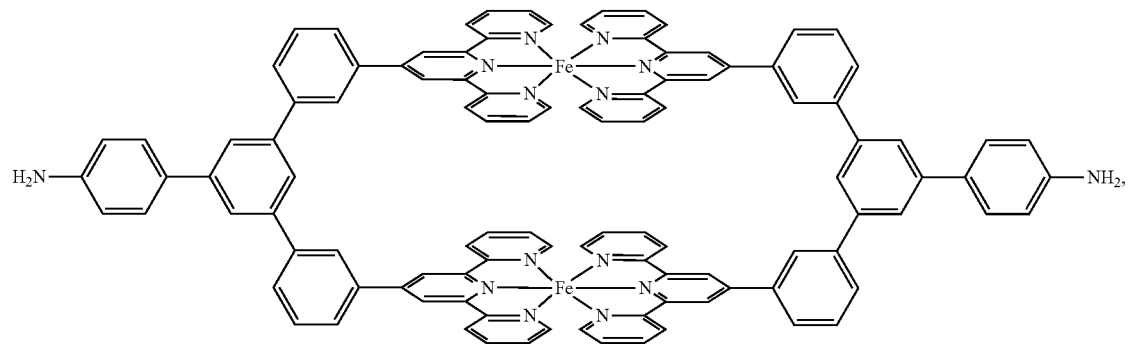
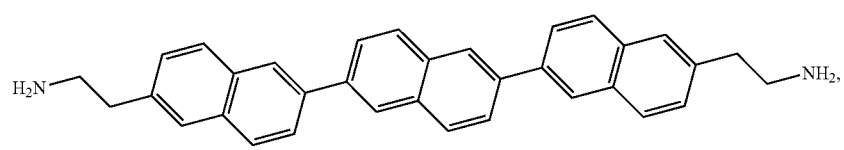

-continued

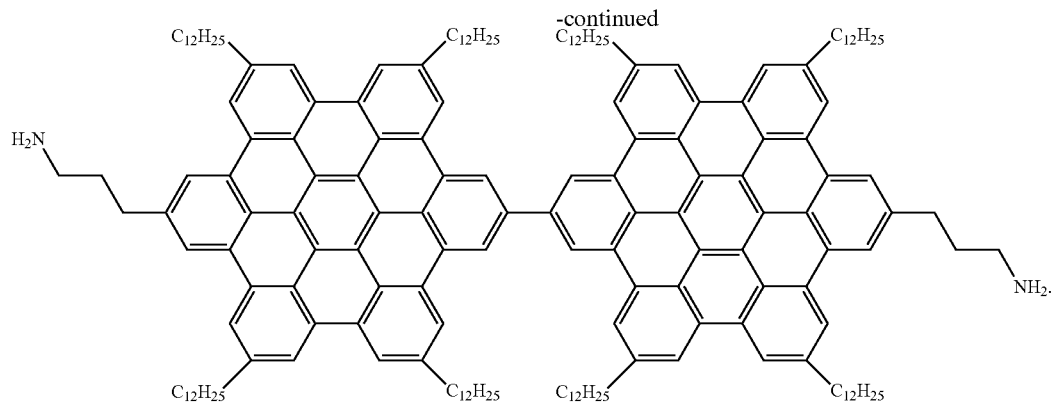

4. A strongly-polarized molecule-graphene molecule heterojunction, wherein the molecule heterojunction comprises the strongly-polarized molecule according to claim 1 bridging between layers of two-dimensional single-layer graphene with a nanogap via amide covalent bonds.

5. A single molecule field effect transistor, comprising a substrate, a gate, a dielectric layer, and the strongly-polarized molecule-graphene molecule heterojunction according to claim 4, wherein the dielectric layer is located between the gate and the strongly-polarized molecule-graphene molecular heterojunction.

6. The single molecule field effect transistor according to claim 5, wherein the material of the gate is one of graphene or metal aluminum.

7. The single molecule field effect transistor according claim 5, wherein the material of the dielectric layer is one of hafnium oxide, zirconium oxide, titanium oxide, and aluminum oxide, or any combinations thereof.

8. The single molecule field effect transistor according to claim 5, wherein:
the dielectric layer is a hafnium oxide layer, and the gate is a graphene layer; or
the dielectric layer is a zirconium oxide layer, and the gate is a graphene layer; or
the dielectric layer is a titanium oxide layer, and the gate is a graphene layer; or
the dielectric layer is an aluminium oxide layer, and the gate is a metal aluminum layer; or
the dielectric layer is a composite layer of aluminium oxide and hafnium oxide, and the gate is a metal aluminum layer.

9. The single molecule field effect transistor according to claim 5, wherein the substrate is a silicon wafer having a silicon oxide layer.

10. The single molecule field effect transistor according to claim 5, wherein the thickness of the dielectric layer is 3-10 nm.

11. The single molecule field effect transistor according to claim 5, wherein the gate is located on the substrate, the dielectric layer is located on the gate, and the strongly-polarized molecule-graphene molecule heterojunction is located on the dielectric layer; or
the strongly-polarized molecule-graphene molecule heterojunction is located on the substrate, the dielectric layer is located on the strongly-polarized molecule-graphene molecule heterojunction, and the gate is located on the dielectric layer.

12. A molecular switch comprising the single molecule field effect transistor according to claim 5.

13. A semiconductor chip comprising the single molecule field effect transistor according to claim 5.

14. The strongly-polarized molecule according to claim 1, wherein $0 \leq x_1 \leq 3$; $0 \leq x_2 \leq 3$.

15. The strongly-polarized molecule according to claim 1, wherein $0 \leq y_1 \leq 2$, $0 \leq y_2 \leq 2$.

16. The strongly-polarized molecule according to claim 1, wherein $M_1$, $M_2$, $M_3$, $M_4$, $M_5$ and $M_6$ are respectively selected from the group consisting of Ru, Fe, Zn, Mn, Co, Ni and cation thereof.

17. The strongly-polarized molecule according to claim 1, wherein $n_1$, $n_2$, $n_3$, $n_4$, $n_5$, $n_6$, $n_7$, $n_8$, $n_9$, $n_{10}$, $n_{11}$, $n_{12}$, $n_{13}$, $n_{14}$, $n_{15}$, $n_{16}$ and $n_{17}$ are smaller than or equal to 3.

18. The strongly-polarized molecule-graphene molecule heterojunction according to claim 4, wherein the two-dimensional single-layer graphene with a nanogap is a two-dimensional single-layer graphene with a nanogap array.

19. The single molecule field effect transistor according to claim 9, wherein the thickness of the silicon oxide layer is 200-400 nm.

* * * * *